(12) United States Patent
Adam et al.

(10) Patent No.: US 6,218,385 B1
(45) Date of Patent: Apr. 17, 2001

(54) 1,2,4,5-TETRAHYDRO-BENZO[D]AZEPIN DERIVATIVES

(75) Inventors: Geo Adam, Schopfheim (DE); Alfred Binggeli, Binningen; Hans-Peter Märki, Basle, both of (CH); Vincent Mutel, Mulhouse; Maurice Wilhelm, Morschwiller le Bas, both of (FR); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/630,702

(22) Filed: Aug. 1, 2000

(30) Foreign Application Priority Data

Aug. 6, 1999 (EP) .................................................. 99115557

(51) Int. Cl.[7] .......................... A61K 31/55; C07D 223/16
(52) U.S. Cl. ...................................... 514/217.01; 540/594
(58) Field of Search ........................ 540/594; 514/217.01

(56) References Cited

U.S. PATENT DOCUMENTS 4,206,210 * 6/1980 Holden ................................. 424/244
5,241,065 * 8/1993 Berger et al. ......................... 540/523
5,444,062 * 8/1995 Coe et al. ............................. 514/260

* cited by examiner

*Primary Examiner*—Bruck Kifle
(74) *Attorney, Agent, or Firm*—George W. Johnston; Dennis P. Tramaloni

(57) ABSTRACT

The present invention is concerned with 1,2,4,5-tetrahydro-benzo[d]azepin derivatives as well as with their pharmaceutically acceptable salts in their racemic and optically active form, which compounds are antagonists at metabotropic glutamate receptors and therefore useful for the treatment of diseases related to these receptors.

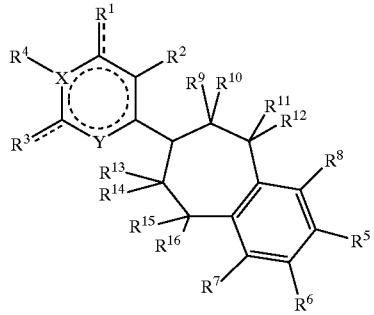

20 Claims, No Drawings

1,2,4,5-TETRAHYDRO-BENZO[D]AZEPIN DERIVATIVES

BACKGROUND OF THE INVENTION

In the central nervous system (CNS) the transmission of stimuli takes place by the interaction of a neurotransmitter sent out by a neuron, with another neuroreceptor. L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) belong to the second main group and, furthermore, belong to the family of G-protein-coupled receptors.

At present, eight different members of these mGluRs are known and some of these even have sub-types. On the basis of structural parameters, the different second messenger signaling pathways and their different affinity to low-molecular weight chemical compounds, these eight receptors can be sub-divided into three sub-groups: mGluR1 and mGluR5 belong to group I, mGluR2 and mGluR3 belong to group III and mGluR4, mGluR6, mGluR7 and mGluR8 belong to group III.

Ligands of metabotropic glutamate receptors belonging to the first group can be used for the treatment or prevention of acute and/or chronic neurological disorders such as epilepsy, stroke, chronic and acute pain, psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depression.

SUMMARY OF THE INVENTION

It has surprisingly been found that the compounds of formula I, below, are antagonists at metabotropic glutamate receptors. Therefore, the compounds of formula I are useful for treating conditions related to stimulation of these glutamate receptors, particularly acute or chronic neurological disorders. In addition, the compounds of this invention are useful in assays for glutamate receptor inhibition.

Thus the present invention is concerned with 1,2,4,5-tetrahydro-benzo[d]azepin derivatives of the formula

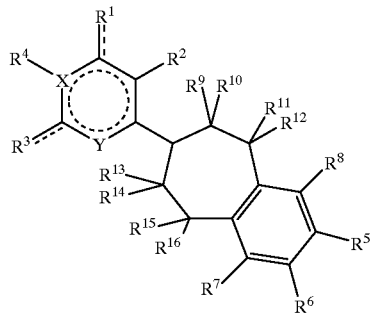

wherein
$R^1$ signifies hydrogen, hydroxy, lower alkyl, oxygen, halogen, or
—OR, —O($C_3$–$C_6$)cycloalkyl, —O(CHR)$_n$—($C_3$–$C_6$) cycloalkyl, —O(CHR)$_n$CN, —O(CHR)$_n$CF$_3$, —O(CHR)(CHR)$_n$NR$_2$, —O(CHR)(CHR)$_n$OR, —O(CHR)$_n$-lower alkenyl, —OCF$_3$, —OCF$_2$—R, —OCF$_2$-lower alkenyl, —OCHRF, —OCHF-lower alkenyl, —OCF$_2$CRF$_2$, —OCF$_2$Br, —O(CHR)$_n$CF$_2$Br, —O(CHR)$_n$-phenyl, wherein the phenyl group may be optionally substituted independently from each other by one to three lower alkyl, lower alkoxy, halogen, nitro or cyano groups,
—O(CHR)(CHR)$_n$-morpholino, —O(CHR)(CHR)$_n$-pyrrolidino, —O(CHR)(CHR)$_n$-piperidino, —O(CHR)(CHR)$_n$-imidazolo, —O(CHR)(CHR)$_n$-triazolo, —O(CHR)$_n$-pyridino, —O(CHR)(CHR)$_n$—OSi-lower alkyl, —O(CHR)(CHR)$_n$OS(O)$_2$-lower alkyl, —(CH$_2$)$_n$CH=CF$_2$, —O(CHR)$_n$-2,2-dimethyl-[1.3]dioxolane, —O(CHR)$_n$—CHOR—CH$_2$OR, —O(CHR)$_n$—CHOR—(CHR)$_n$—CH$_2$OR or
—SR or —S(CHR)$_n$COOR, or
—NR$_2$, —N(R)(CHR)(CHR)$_n$OR, —N(R)(CHR)$_n$CF$_3$, —N(R)(CHR)(CHR)$_n$-morpholino, —N(R)(CHR)(CHR)$_n$-imidazolo, —N(R)(CHR)(CHR)$_n$-pyrrolidino, —N(R)(CHR)(CHR)$_n$-pyrrolidin-2-one, —N(R)(CHR)(CHR)$_n$-piperidino, —N(R)(CHR)(CHR)$_n$-triazolo, —N(R)(CHR)$_n$-pyridino, or
$R^1$ and $R^4$ are interconnected to the groups —(CH$_2$)$_{3-5}$—, —(CH$_2$)$_2$—N=, —CH=N—N=—, —CH=CH—N=, —NH—CH=CH— or
—NR—CH$_2$—CH$_2$— and form together with any N or C atoms to which they are attached an additional ring;
n is 1–6;
R signifies hydrogen, lower alkyl or lower alkenyl, independently from each other, if more than one R is present;
$R^2$ signifies nitro or cyano;
$R^3$ signifies hydrogen, lower alkyl, =O, —S, —SR, —S(O)$_2$-lower alkyl, —($C_3$–$C_6$)cycloalky or piperazino, optionally substituted by lower alkyl, or
—CONR$_2$, —(CHR)$_n$CONR$_2$, —(CHR)$_n$OR, —(CH$_2$)$_n$—CF$_3$, —CF$_3$, —(CHR)$_n$OC(O)CF$_3$, —(CHR)$_n$COOR, —(CHR)$_n$SC$_6$H$_5$, wherein the phenyl group may be optionally substituted independently from each other by one to three lower alkyl, lower alkoxy, halogen, nitro or cyano groups,
—(CHR)$_n$-1,3-dioxo-1,3-dihydro-isoindol, —(CHR)$_n$-tetrahydro-pyran-2-yloxy or —(CHR)$_n$—S-lower alkyl, or
—NR$_2$, —NRCO-lower alkyl, —NRCHO, —N(R)(CHR)$_n$CN, —N(R)(CHR)$_n$CF$_3$, —N(R)(CHR)(CHR)$_n$—OR, —N(R)C(O)(CHR)$_n$O-lower alkyl, —NR(CHR)$_n$-lower alkyl, —NR(CHR)(CHR)$_n$—OR, —N(R)(CHR)

(CHR)$_n$—O-phenyl, wherein the phenyl group may be optionally substituted independently from each other by one to three lower alkyl, lower alkoxy, halogen, nitro or cyano groups,
—N(R)(CHR)$_n$-lower alkenyl, —N(R)(CHR)(CHR)$_n$—O—(CHR)$_n$OR, —N(R)(CHR)$_n$C(O)O-lower alkyl, —N(R)(CHR)$_n$C(O)NR-lower alkyl, —N(R)(CH$_2$)$_n$-2,2-dimethyl-[1.3]dioxolane, —N(R)(CHR)(CHR)$_n$ morpholino, —N(R)(CHR)$_n$-pyridino, —N(R)(CHR)(CHR)$_n$-piperidino, —N(R)(CHR)(CHR)$_n$-pyrrolidino, —N(R)(CHR)(CHR)$_n$—O-pyridino, —N(R)(CHR)(CHR)$_n$imidazolo, —N(R)(CHR)$_n$—CR$_2$—(CHR)$_n$—OR, —N(R)(CHR)$_n$—CR$_2$—OR, —N(R)(CHR)$_n$—CHOR—CH$_2$OR, —N(R)(CHR)$_n$—CHOR—(CHR)$_n$—CH$_2$OR, or
—OR, —O(CHR)$_n$CF$_3$, —OCF$_3$, —O(CHR)(CHR)$_n$—O-phenyl, wherein the phenyl group maybe optionally substituted independently from each other by one to three lower alkyl, lower alkoxy, halogen, nitro or cyano groups, —O(CHR)(CHR)$_n$—O-lower alkyl, —O(CHR)$_n$-pyridino or
—O(CHR)(CHR)$_n$-morpholino;
or R$^3$ and R$^4$ are interconnected to the groups —(CH$_2$)$_{3-5}$—, —(CH$_2$)$_2$—N=, —CH=N—N=—, —CH=CH—N=, —NH—CH=CH— or NR—CH$_2$—CH$_2$— and form together with any N or C atoms to which they are attached an additional ring; and
R$^4$ signifies hydrogen, lower alkyl, lower alkenyl or nitro, or —OR, —OCF$_3$, —OCF$_2$—R, —OCF$_2$-lower alkenyl, —OCHRF, —OCHF-lower alkenyl, —O(CHR)$_n$CF$_3$, or —(CHR)$_n$CHRF, —(CHR)$_n$CF$_2$R, —(CHR)$_n$CF$_3$, —(C$_3$–C$_6$)cycloalkyl, —(CHR)$_n$(C$_3$–C$_6$)cycloalkyl, —(CHR)$_n$CN, —(CHR)$_n$-phenyl, wherein the phenyl group may be optionally substituted independently from each other by one, to three lower alkyl, lower alkoxy, halogen, nitro or cyano groups,
—(CHR)(CHR)$_n$OR, —(CHR)$_n$CHORCH$_2$OR; —(CHR)(CHR)$_n$NR$_2$, —(CHR)$_n$COOR, —(CHR)(CHR)$_n$OSi-lower alkyl, —(CHR)(CHR)$_n$—OS(O)$_2$-lower alkyl, —(CH$_2$)$_n$—CH=CF$_2$, —CF$_3$, —CF$_2$—R, —CF$_2$-lower alkenyl, —CHRF, —CHF-lower alkenyl, —(CHR)$_n$-2,2-dimethyl-[1.3]dioxolane, —(CH$_2$)$_n$-2-oxo-azepan-1-yl, —(CHR)(CHR)$_n$-morpholino, —(CHR)$_n$-pyridino, —(CHR)(CHR)$_n$-imidazolo, —(CHR)(CHR)$_n$-triazolo, —(CHR)(CHR)$_n$-pyrrolidino, optionally substituted by —(CH$_2$)$_n$OH, —(CHR)(CHR)$_n$-3-hydroxy-pyrrolidino or —(CHR)(CHR)$_n$-piperidino, or
—NR$_2$, —N(R)(CHR)$_n$-pyridino, —N(R)C(O)O-lower alkyl, —N(CH$_2$CF$_3$)C(O)O-lower alkyl, —N[C(O)O-lower alkyl]$_2$, —NR—NR—C(O)O-lower alkyl or —N(R)(CHR)$_n$CF$_3$, —NRCF$_3$, —NRCF$_2$—R, —NRCF$_2$-lower alkenyl, —NRCHRF, —NRCHP-lower alkenyl;
or is absent if X is —N= or =N—;
R$^5$, R$^6$ signify hydrogen, lower alkyl, lower alkoxy, amino, nitro, —SO$_2$NH$_2$ or halogen; or
R$^5$ and R$^6$ are interconnected to the group —O—CH$_2$—O— and form together with the C atoms to which they are attached an additional 5-membered ring;
R$^7$, R$^8$ signify hydrogen, lower alkyl, lower alkoxy, amino, nitro or halogen;
R$^9$, R$^{10}$ signify hydrogen or lower alkyl;
R$^{11}$, R$^{12}$ signifies hydrogen, lower alkyl, hydroxy, lower alkoxy, lower alkoxycarbonyloxy or lower alkanoyloxy;
R$^{13}$, R$^{14}$ signify hydrogen, tritium or lower alkyl;
R$^{15}$, R$^{16}$ signifies hydrogen, tritium, lower alkyl, hydroxy, lower alkoxy or are together an oxo group; or x signifies —N=, =N—, —N<, >C=or =C<;
Y signifies —N=, =N—, —NH—, —CH= or =CH—; and
the dotted line may be a bond when R$^1$, R$^3$ or R$^4$ represent a bivalent atom,
as well as with the pharmaceutically acceptable salts of each compound of formula I and the racemic and optically active forms of each compound of formula I.

Objects of the present invention are compounds of formula I and their pharmaceutically acceptable salts per se and as pharmaceutically active substances, their manufacture, medicaments based on a compound in accordance with the invention and their production as well as the use of the compounds in accordance with the invention in the control or prevention of illnesses of the aforementioned kind, and, respectively, for the production of corresponding medicaments. Furthermore, the use of radiolabeled mGluR1 receptor antagonists of formula I in a binding assay is also an object of the present invention.

DETAILED DESCRIPTION OF THE INVENTION

Preferred compounds of formula I include those compounds where R$^5$, R$^6$, R$^7$, R$^8$, R$^9$, R$^{10}$, R$^{11}$, R$^{12}$, R$^{13}$, R$^{14}$, R$^{15}$ and R$^{16}$ are all hydrogen, and such compounds where X and Y are both nitrogen. Also preferred are compounds of formula I where R$^1$ is =O, OR, NR$_2$, or lower alkyl (A). Further preferred compounds are compounds of formula I wherein R$^3$ is hydrogen, lower alkyl, or NR$_2$(B). Also preferred are compounds of formula I where R$^1$ is =O, hydroxy, —O(CHR)$_n$CF$_3$, or —O(CHR)(CHR)$_n$-triazolo (C). In addition, compounds where R$^3$ and R$^4$ are interconnected to the groups —(CH$_2$)$_{3-5}$— to form together with any N or C atoms to which they are attached an additional ring are preferred(D). In any of the compounds of groups A, B, C, or D, R$^5$, R$^6$, R$^7$, R$^8$, R$^9$, R$^{10}$, R$^{11}$, R$^{12}$, R$^{13}$, R$^{14}$, R$^{15}$ and R$^{16}$ may in addition be hydrogen, and/or X and Y may both be nitrogen. Also, in any compound of formula I, one or more of R$^{13}$, R$^{14}$, R$^{15}$, and R$^{16}$ maybe tritium. An example of such a compound is 1-ethyl-2-methyl-6-oxo-4-(1,1,2-tritritio-1,2,4,5-tetrahydro-benzo[d]azepin-3-yl)-1,6-dihydro-pyrimidine-5-carbonitrile.

Preferred compounds of formula I (and group C) in the scope of the present invention are those, in which R$^1$ is =O or hydroxy and R$^2$ is NO$_2$.

The following are examples of such compounds:
3-Ethyl-2-methyl-5-nitro-6-(1,2,4,5-tetrahydro-benzo[d] azepin-3-yl)-3H-pyrimidin-4-one
3-(2-fluoro-ethyl)-2-methyl-5-nitro-6-(1,2,4,5-tetrahydro-benzo[d]azepin-3-yl)-3H-pyrimidin-4-one,
2-methyl-5-nitro-6-(1,2,4,5-tetrahydro-benzo[d]azepin-3-yl)-3-(2,2,2-trifluoro-ethyl)-3H-pyrimidin-4-one or
2-methyl-5-nitro-6-(1,2,4,5-tetrahydro-benzo[d]azepin-3-yl)-pyrimidin-4-ol.

Compounds of formula I, in which R$^1$ is =O and R$^2$ is —CN are also preferred.

The following are examples of such compounds:
2-Amino-6-oxo-4-(1,2,4,5-tetrahydro-benzo[d]azepin-3-yl)-1,6-dihydro-pyrimidine-5-carbonitrile,
6-oxo-4-(1,2,4,5-tetrahydro-benzo[d]azepin-3-yl)-1,6-dihydro-pyrimidine-5-carbonitrile,
2-ethylamino-6-oxo-4-(1,2,4,5-tetrahydro-benzo[d]azepin-3-yl)-1,6-dihydro-pyrimidine-5-carbonitrile,
1,2-dimethyl-6-oxo-4-(1,2,4,5-tetrahydro-benzo[d]azepin-3-yl)-1,6-dihydro-pyrimidine-5-carbonitrile,
1-ethyl-2-methyl-6-oxo-4-(1,2,4,5-tetrahydro-benzo[d] azepin-3-yl)-1,6-dihydro-pyrimidine-5-carbonitrile, 2-amino-1-ethyl-6-oxo-4-(1,2,4,5-tetrahydro-benzo[d]
azepin-3-yl)-1,6-dihydro-pyrimidine-5-carbonitrile,
1-cyclopropylmethyl-2-methyl-6-oxo-4-(1,2,4,5-
tetrahydro-benzo[d]azepin-3-yl)-1,6-dihydro-pyrimidine-
5-carbonitrile,
1-allyl-2-methyl-6-oxo-4-(1,2,4,5-tetrahydro-benzo[d]
azepin-3-yl)-1,6-dihydro-pyrimidine-5-carbonitrile,
1-cyanomethyl-2-methyl-6-oxo-4-(1,2,4,5-tetrahydro-
benzo[d]azepin-3-yl)-1,6-dihydro-pyrimidine-5-
carbonitrile,
1-(2-dimethylamino-ethyl)-2-methyl-6-oxo-4-(1,2,4,5-
tetrahydro-benzo[d]azepin-3-yl)-1,6-dihydro-pyrimidine-
5-carbonitrile,
1-isopropyl-6-oxo-4-(1,2,4,5-tetrahydro-benzo[d]azepin-3-
yl)-1,6-dihydro-pyrimidine-5-carbonitrile,
1-(2-hydroxy-ethyl)-6-oxo-4-(1,2,4,5-tetrahydro-benzo[d]
azepin-3-yl)-1,6 dihydro-pyrimidine-5-carbonitrile,
2-(2-hydroxy-ethyl)-6-oxo-4-(1,2,4,5-tetrahydro-benzo[d]
azepin-3-yl)-1,6 dihydro-pyrimidine-5-carbonitrile,
2-methyl-6-oxo-4-(1,2,4,5-tetrahydro-benzo[d]azepin-3-
yl)-1-(2,2,2-trifluoro-ethoxy)-1,6-dihydro-pyrimidine-5-
carbonitrile,
2-methyl-1-methylamino-6-oxo-4-(1,2,4,5-tetrahydro-
benzo[d]azepin-3-yl)-1,6-dihydro-pyrimidine-5-
carbonitrile or
1-amino-2-methyl-6-oxo-4-(1,2,4,5-tetrahydro-benzo[d]
azepin-3-yl)-1,6-dihydro-pyrimidine-5-carbonitrile.

Preferred compounds of formula I (and group C) in the scope of the present invention are those, in which $R^1$ is 2,2,2-trifluoroethoxy and $R^2$ is —CN.

The following are examples of such compounds:
2-(2-Morpholin-4-yl-ethylamino)-4-(1,2,4,5-tetrahydro-
benzo[d]azepin-3-yl)-6-(2,2,2-trifluoro-ethoxy)-
pyrimidine-5-carbonitrile,
2-(3-morpholin-4-yl-propylamino)-4-(1,2,4,5-tetrahydro-
benzo[d]azepin-3-yl)-6-(2,2,2-trifluoro-ethoxy)-
pyrimidine-5-carbonitrile,
2-(2-hydroxy-ethylamino)-4-(1,2,4,5-tetrahydro-benzo[d]
azepin-3-yl)-6-(2,2,2-trifluoro-ethoxy)-pyrimidine-5-
carbonitrile or
(3-imidazol-1-yl-propylamino)-4-(1,2,4,5-tetrahydro-benzo
[d]azepin-3-yl)-6-(2,2,2-trifluoro-ethoxy)-pyrimidine-5-
carbonitrile.

Preferred compounds of formula I (and group C) in the scope of the present invention are those, in which $R^1$ is 3-[1,2,4]triazol1-yl-propoxy and $R^2$ is —$NO_2$ or —CN.

The following example represents such a compound:
3-[2-Methyl-5-nitro-6-(3-[1,2,4]triazol-1-yl-propoxy)-
pyrimidin-4-yl]-2,3,4,5-tetrahydro-1H-benzo[d]azepine.

Preferred compounds of formula I (and group D) in the scope of the present invention are those, in which $R^3$ and $R^4$ are interconnected to the group —$(CH_2)_5$— and form together with the N or C atoms to which they are attached an additional 7 membered ring and $R^2$ is —$NO_2$ or —CN.

The following example represents such a compound:
4-Oxo-2-(1,2,4,5-tetrahydro-benzo[d]azepin-3-yl)-4,6,7,8,
9,10-hexahydro-pyrimido[1,2-a]azepine-3-carbonitrile.

As shown above, the $R^1$, $R^3$, and $R^4$ positions may be substituted with individual atoms, groups, or unsubstituted or substituted rings including cycloalkyl, or phenyl, or aromatic/nonaromatic 5 to 7-membered heterocycles with 1 to 3 heteroatoms selected from oxygen and nitrogen. Or $R^1$ with $R^4$ or $R^3$ with $R^4$ may form cycloalkyl or a nitrogen heterocycle. Among the $R^1$ variables are hydrogen, halogen, or =O, or a group such as hydroxy, lower alkoxy,alcohol, or substituted amino. $R^1$ variables also include cycloalkyl, phenyl, and heterocycles as described above. Various groups and most rings may be linked to the ring depicted in formula I by variously substituted ether and amine linkages. Similarly, $R^3$ includes hydrogen,=O, =S, and groups such as lower alkyl, amino, lower alkoxy, lower alkyl thio or sulfoxide, various substituted amines, or rings such as cycloalkyl, phenyl, or above-described heterocyclic ring directly or indirectly linked (by linkers such as ethers, thioethers, and amines) to the ring of formula I, which ring may be fused with phenyl. Similarly for the $R^4$ position, some variables are hydrogen, groups such as nitro, hydroxy, lower alkyl, lower alkenyl, amino, alcohols, lower alkoxy, lower alkyl substituted with cyano or perfluorolower alkyl, substituted amino, cycloalkyl, lower alkyl ethers, N-linked carboxylic acid esters, and heterocyclic rings as described above linked by lower alkyl. Thus the $R^1$, $R^3$, and $R^4$ positions present different combinations of cyclic and non-cyclic variables. Compounds of this invention may have rings at one, two, or three positions (steric considerations permitting), or an atom at one position, a ring at another, and a group at a third, in any combination. The rings selected may be oxygen heterocycles, or nitrogen heterocycles, or mixed heterocycles.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like.

The term "lower alkenyl" used in the present description denotes straight-chain or branched unsaturated hydrocarbon residues with 2–7 carbon atoms, preferably with 2–4 carbon atoms.

The term "lower alkoxy" denotes a lower alkyl residue in the sense of the foregoing definition bonded via an oxygen atom.

The term "halogen" embraces fluorine, chlorine, bromine and iodine.

The compounds of formula I and their pharmaceutically acceptable salts can be manufactured by a) reacting a compound of the formula

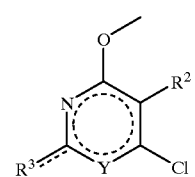

II with a compound of formula

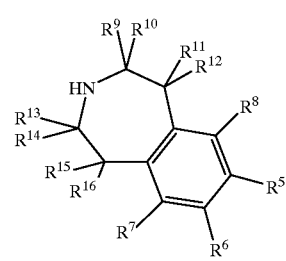

III to a compound of formula

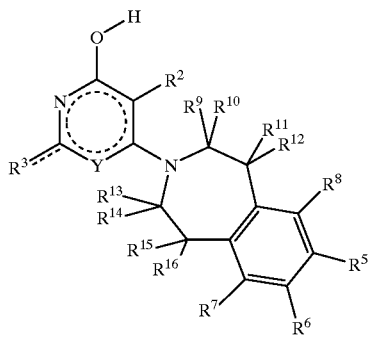

I-1 wherein the substituents are described above, or
b) reacting a compound of the formula

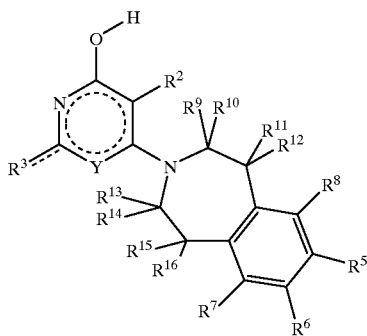

to a compound of formula

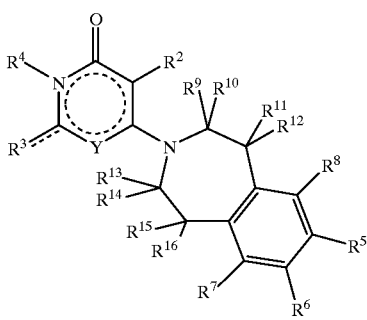

I-2 or to a compound of formula

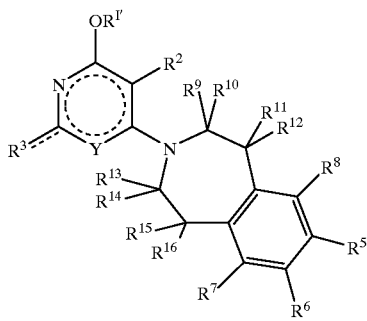

I-3 wherein $R^2$ to $R^{16}$ have the significances given above and $R^1$ is lower alkyl, $-(C_3-C_6)$cycloalkyl, $-(CHR)_n(C_3-C_6)$ cycloalkyl, $-(CHR)_nCN$, $-(CHR)_nCF_3$, $-(CHR)(CHR)_n$ $NR_2$, $-(CHR)(CHR)_nOR$, $-(CHR)_n$-lower alkenyl, $-CF_3$, $-CF_2-R$, $-CF_2$-lower alkenyl, $-CHRF$, $-CHF$-lower alkenyl, $-CF_2CRF_2$, $-CF_2Br$, $-(CHR)_nCF_2Br$, $-(CHR)_n$-phenyl, wherein the phenyl group may be optionally substituted independently from each other by one to three lower alkyl, lower alkoxy, halogen, nitro or cyano groups, $-(CHR)(CHR)_n$-morpholino, $-(CHR)(CHR)_n$-pyrrolidino, $-(CHR)(CHR)_n$-piperidino, $-(CHR)(CHR)_n$-imidazolo, $-(CHR)(CHR)_n$-triazolo, $(CHR)_n$-pyridino, $-(CHR)(CHR)_n-OSi$-lower alkyl, $(CHR)(CHR)_nOS(O)_2$-lower alkyl, $-(CH_2)_nCH=CF_2$, $-(CHR)_n$-2,2-dimethyl-[1.3]dioxolane, $-(CHR)_nCHOR-CH_2OR$ or $-(CHR)_n-$ $CHOR-(CHR)_n-CH_2OR$.

c) reacting a compound of formula

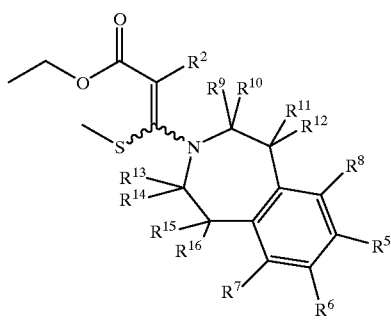

IV, Z and/or E with a compound of formula

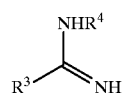

V to a compound of formula

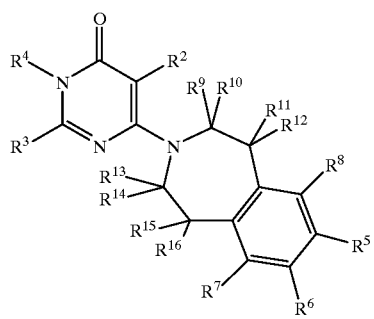

I-2a wherein the substituents are described above, or d) reacting a compound of formula

VI

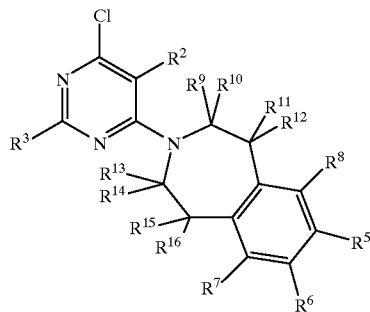

with a an alcohol, thiol, a primary or secondary amine to a compound of formula

I-4

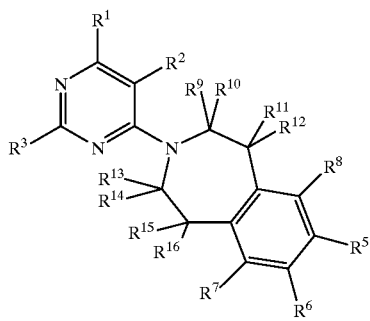

wherein the substituents are given above, or e) reacting a compound of formula

VII

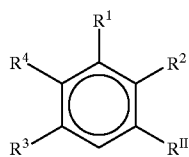

wherein $R^{II}$ in formula VII is fluoro, chloro, bromo or a trifluoro-methansulfonyloxy group, with a compound of formula

III

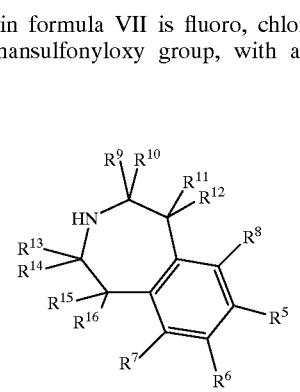

to a compound of formula

I-5

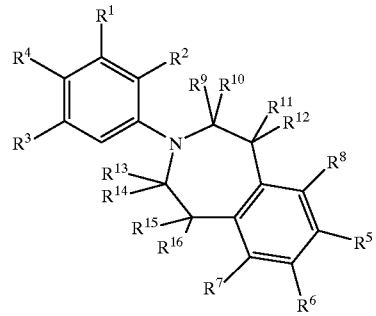

wherein the substituents are described above, f) reacting a compound of formula

VIIIb

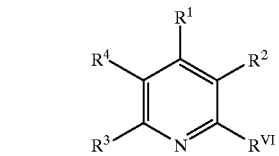

wherein, $R^{VI}$ is a fluoro, chloro, bromo or a trifluoro-methansulfonyloxy group, with a compound of formula

III

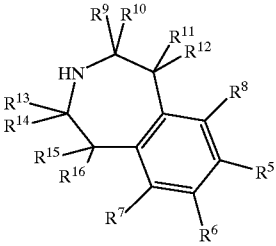

to a compound of formula I-5,

I-6

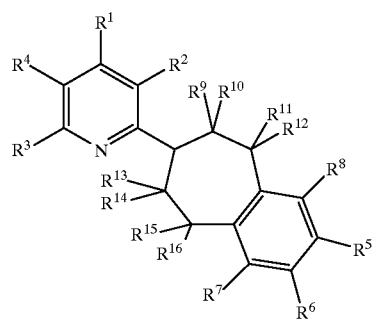

wherein the substituents are described above,
and, if desired, introducing and removing protective groups in compounds of formula I, alkylating of OH or NH functions in compounds of formula I, cleaving ether functions, converting a functional group in a compound of formula I into another functional group directly or via a suitable activating group and, if desired,
converting a compound of formula I into a pharmaceutically acceptable salt or into its optically active form.
In the following schemes I–VIII and in Examples 1–273 the reaction steps and reaction variants a)–f) are described in more detail.
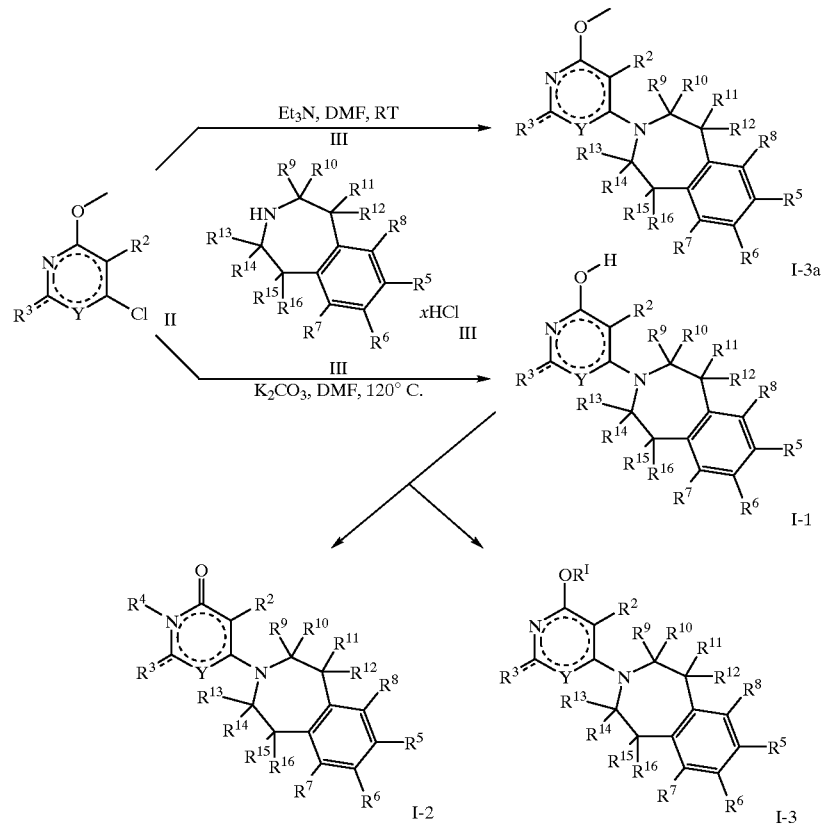
Scheme I
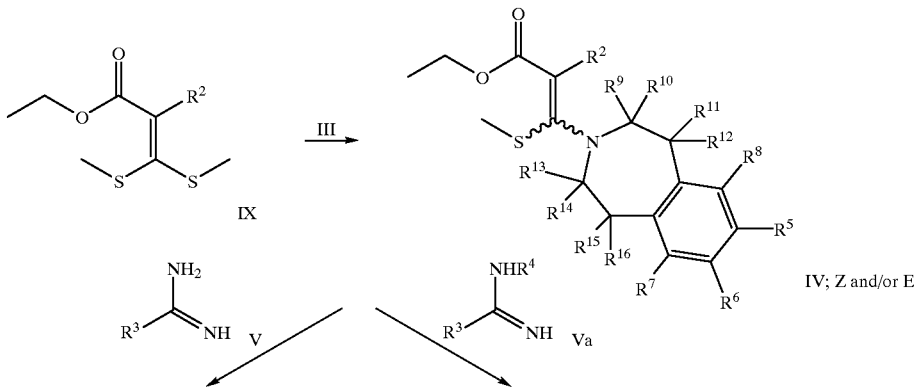
Scheme II

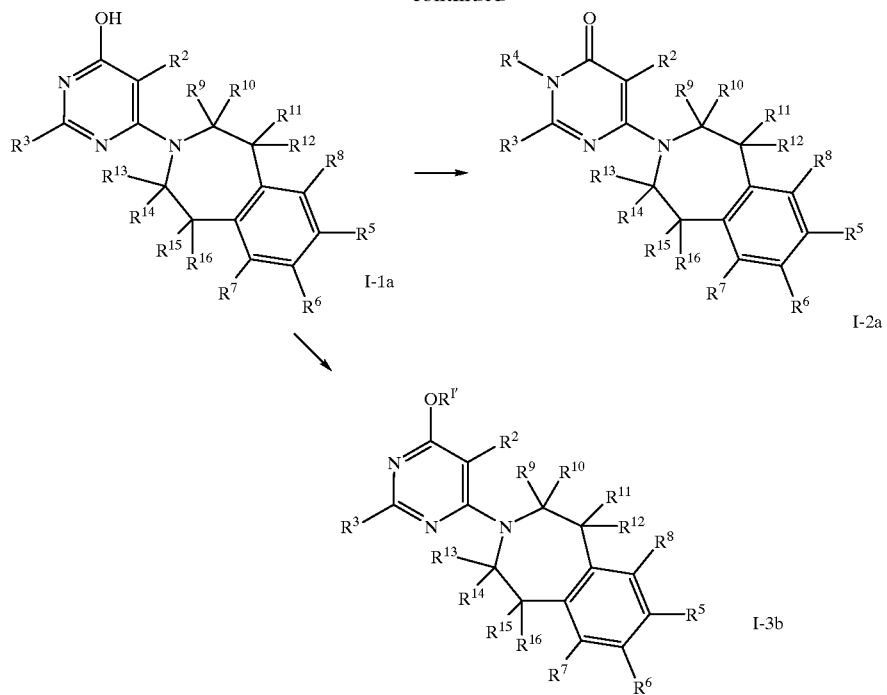
Scheme III
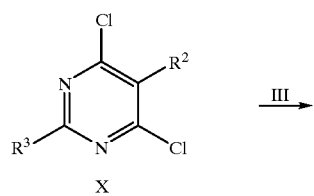
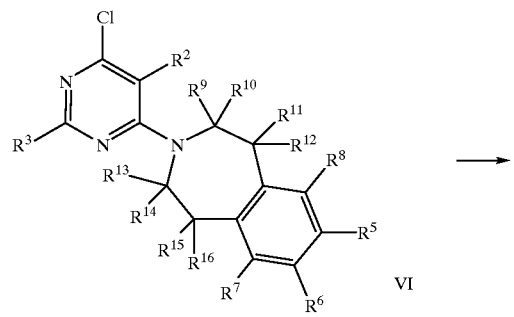
Scheme IV
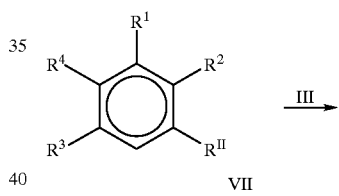
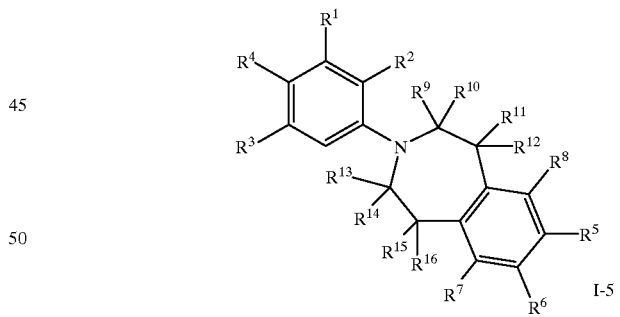
Scheme V
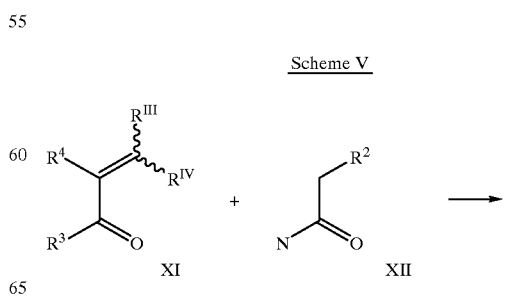

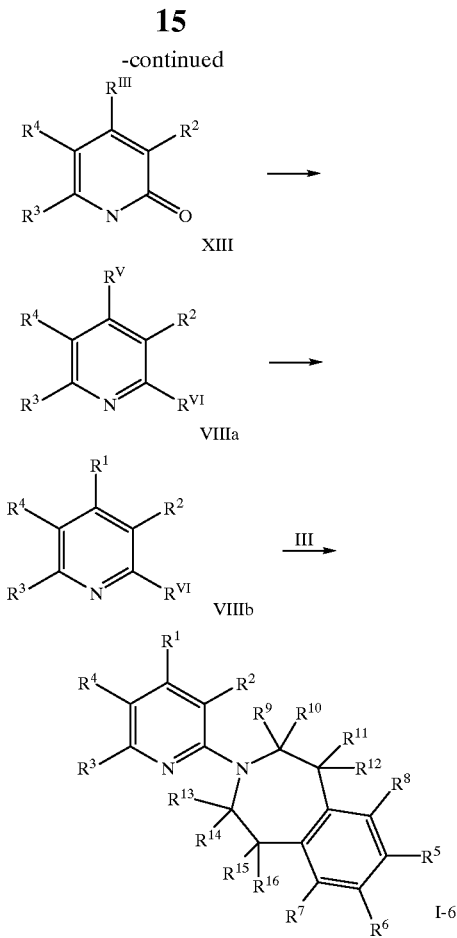

Chloro-methoxy-nitro or cyano pyrimidines II (Scheme I) are known [e.g. 6-chloro-4-methoxy-2-methyl-5-nitro-pyrimidine: Helv. (1958), 41, 1806] or can be prepared in analogy to procedures described for known compounds, e.g. from 4,6-dichloro-5-cyano-pyrimidine [Monatshefte Chemie (1965), 96, 1573–1578] and sodium methoxide in methanol at low temperature, preferably between −20° C. and +20° C. They react with optionally substituted secondary amines III in the presence of a base like triethylamine in solvents like N,N-dimethylformamide, dimethylsulfoxide, acetone, methyl-ethylketone or tetrahydrofuran at temperatures between 0° C. and 100° C. to the tertiary amines I-3a; at elevated temperatures however, preferentially 100° C. to 150° C. in the presence of potassium carbonate in solvents like N,N-dimethylformamide or N-methylpyrrolidone the tertiary amines I-1 are formed where simultaneously the methoxy group is transformed into a hydroxy group. Known analogues of II bearing a carbonyl function instead of the methoxy moiety, e.g. 2-amino-6-chloro-5-nitro-4(2H)-pyrimidinone [J. Chem. Soc. 1964, 4769–4774] react with optionally substituted secondary amines III preferentially at elevated temperatures, preferentially 100° C. to 150° C. in the presence of potassium carbonate, triethylamine or ethyl-diisopropylamine in solvents like N,N-dimethylformamide or N-methylpyrrolidone to adducts I-1. Alkylation of adducts I-1 using optionally substituted alkyl halides, tosylates, mesylates or trifluoro-methansulfonates in solvents like ethanol, methanol, dichloromethane, chloroform, N,N-dimethylformamide, dimethylsulfoxide, acetone, methyl-ethylketone or tetrahydrofuran in the presence of base like alkali carbonates, e.g. sodium, potassium or cesium carbonate, tertiary amines like triethylamine or ethyl-diisopropylamine, alkali methyl hydrides, like sodium or potassium hydride, or phase transfer catalysts like benzyl-trimethylammonium chloride in the presence of solid or concentrated aqueous sodium hydroxide gives variable mixtures of N- and/or O-alkylated products I-2 and I-3. The products I-2 and I-3 may contain in the N- or O-alkyl function functional groups in protected form which allow further structural modifications after removal of the protective functions.

The introduction of an $R^4$ substituent equal OH or $NH_2$ into pyrimidinoles I-1 (Scheme I) can be achieved using suitable oxygen or nitrogen transfer reagents. Chloramine or preferentially the more stable mesitylenesulfonylhydroxy-lamine [Synthesis 1972, 140] are suitable agents for the introduction of an $NH_2$ group. Both are used in solvents as ethers like tetrahydrofuran or dimethoxyethane or in N,N-dimethylformamide or dimethylsulfoxide in the presence of a base like sodium hydride or potassium carbonate at temperatures between room temperature and 60° C. Conversion of pyrimidinoles I-1 into their O-silylated analogues by treatment with suitable silylating agents like hexamethyldisilazane and trimethylchlorosilane followed by treatment with the oxodiperoxymolybdenum (pyridine) (HMPA) complex [J. Org. Chem. 43 (1978), 188–1961 in solvents like dichloromethane or chloroform at temperatures between room temperature and 60° C. gives pyrimidinones I-2 with $R^4$ equal OH. Compounds I-2 with $R^4$ equal OH can be further derivatized by known methods as alkylation with a suitable alkyl halide, tosylate or triflate in the presence of a base like potassium carbonate or sodium hydride in solvents like tetrahydrofuran, acetonitril or N,N-dimethylformamide at temperatures between room temperature and 100° C. Compounds I-2 with $R^4$ equal $NH_2$ are preferentially converted into a mono Boc derivative (preparation of the di-Boc derivative with di-tert. butyl dicarbonate, 4-dimethylamino pyridine in dichloromethane at room temperature followed by removal of one Boc group by stirring in dichloromethane in the presence of silica gel) and then alkylated under similar conditions as described for compounds I-2 with $R^4$ equal OH. The Boc group can then easily be removed by known methods.

Bis(methylthio)-acrylates IX react with optionally substituted secondary amines III in the presence of bases like potassium carbonate and/or triethylamine in solvents like ethanol, methanol, acetone or methyl-ethylketone at temperatures between room temperature and 100° C. to adducts IV, which can be formed as Z-isomer, as mixture of E and Z isomers or as E isomer (Scheme II). Adducts IV can be reacted with amidines, urea or thiourea derivatives V either in the presence of 1,8-diazabicyclo[5.4.0]undec-7-ene in N,N-dimethylformamide or dimethylsulfoxide at temperatures between 70° C. and 140° C. or in the presence of sodium ethylate in ethanol preferentially at reflux thus yielding pyrimidineoles I-1a or pyrimidinones I-2a. Pyrimidinoles I-1a can then be alkylated as described for the sequence I-1 =>I-2 and I-3 in Scheme I. If an allyl moiety is introduced as $R^4$, then, it can also serve as protective function. Thus, it allows modification at other parts of the molecules, e.g. in $R^3$ and a later removal of the N-allyl function by lithium borohydride in the presence of palladium(II)acetate and triphenylphosphin in an inert solvent like tetrahydrofuran or 1,2-dimethoxyethane at temperatures between room temperature and 60° C. Alternativeley, adducts IV can be reacted with substituted amidine derivatives Va in which $R^3$ and $R^4$ are optionally connected to form a 5, 6 or 7 membered ring either in the presence of 1,8-diazabicyclo[5.4.0]undec-7-ene in N,N- dimethylformamide or dimethylsulfoxide at temperatures between 70° C. and 140° C. or in the presence of sodium ethylate in ethanol preferentially at reflux yielding pyrimidinones I-2a.

Selective monosubstituion of di-chloro pyrimidines X (Scheme III) with optionally substituted secondary amines III can be performed in solvents like N,N-dimethylformamide or dimethylsulfoxide in presence of a base like triethylamine at temperatures between –10° C. and room temperature producing mono-chloro pyrimidines VI. The remaining chloro atom in compounds VI can then be replaced by i) alkoxy functions by treatment with an alcoholate in the corresponding alcohol as solvent or in an inert solvent like tetrahydrofuran, N,N-dimethylformamide or dimethylsulfoxide at temperatures between room temperature and 100° C.; by ii) amino functions by treatment with an amine in an inert solvent like tetrahydrofuran, N,N-dimethylformamide or dimethylsulfoxide at temperatures between room temperature and 100° C.; by iii) thio functions by treatment with a thiol in the presence of a base like triethylamine or sodium hydride in an alcohol, N,N-dimethylformamide or dimethylsulfoxide at temperatures between room temperature and 100° C. The replacement of the chloro-group by a hydroxy function is preferentially performed in a two step procedure: a 4-methoxy-benzyloxy function is introduced first by reacting VI with the corresponding alcoholate as described above followed by treatment with methanolic hydrogen chloride at temperatures between 0° C. and 50° C.

Compounds of formula X (Scheme III) where $R^3$ is methylthio and $R^2$ is cyano [J.Heterocycl.Chem. (1971), 8(3), 445] or $R^2$ is nitro [Aust.J.Chem. (1990), 43(1), 55] are known. Selective monosubstitution with optionally substituted secondary amines of formula III giving compounds VI and, thereupon, substitution of the remaining chloro atom can be performed as described above to yield compounds of formula I-4. After conversion of the 2-methylthio derivatives, already appropriately substituted in the 6-position of the pyrimidines, into the 2-methylsulphonyl derivatives according to known oxidative methods, the corresponding O—, N— or S— substituted pyrimidine derivatives can be obtained by treatment with alcoholates, amines and thiolates in tetrahydrofuran, 1,2-dimethoxyethane, dimethylformamide or dimethyl sulphoxide at temperatures between room temperature and about 150° C.

Compounds of formula I-4, where $R^2$ is cyano, $R^1$ is methylthio and $R^3$ is amino, also can be synthesized by reacting 2-amino-4-bromo-6-methylsulfanyl-pyrimidine-5-carbonitrile, prepared in an analogous manner to the 4-chloro derivative described in J.Chem.Soc. Chem.Commun. 1974, 9, 350, with optionally substituted secondary amines of formula III. Furthermore, compounds of formula I-4, where $R^2$ is cyano, $R^1$ is alkylthio can be synthesized starting from compounds of formula VI, where $R^3$ is methylthio, by its transformation into the 2-methylsulphonyl derivatives according to known oxidative methods, followed by the treatment with alcoholates, amines and thiolates in tetrahydroftiran, 1,2-dimethoxyethane, dimethylformamide or dimethylsulfoxide at temperatures between room temperature and about 150° C. Thereupon, substitution of the remaining chloro atom by alkylthiolates in tetrahydrofurane, 1,2-dimethoxyethane, dimethylformamide or dimethylsulfoxide at temperatures between room temperature and about 150° C. yields the O—, N— or S— substituted 6-alkylthio pyrimidin derivatives.

Alpha amino substituted nitro or cyano benzene compounds I-5 (Scheme IV) are prepared from the corresponding known benzene derivatives VII with $R^{II}$ being a fluoro, chloro, bromo or a trifluoro-methansulfonyloxy function by treatment with secondary amines III at temperatures preferentially between room temperature and 100° C. in the presence of a base like potassium carbonate or triethylamine in solvents like methanol, ethanol, acetonitrile, tetrahydrofuran, acetone, methyl-ethylketone, N,N-dimethylformamide or dimethylsulfoxide. Cyano or nitro pyridones XIII are known or can be prepared from unsaturated ketones XI (Scheme V) bearing a leaving group $R^{III}$ or $R^{IV}$ being an ONa or an S-alkyl function together with a second functionality $R^{III}$ or $R^{IV}$ being a hydrogen or an alkoxy function. Such unsaturated ketones XI can be condensed with cyano or nitro acetamide either with mixed acid base catalysis using a mixture of a base like piperidine or pyrrolidine with acetic or formic acid in solvents water, ethanol and tetrahydrofuran or in the presence of a base like sodium hydride or a sodium or potassium alkoholate in solvents like ethanol, methanol, tert.-butanol, N,N-dimethylformamide or dimethylsulfoxide at temperatures between room temperature and 120° C. leading to pyridones XIII with $R^{III}$ being a hydrogen or an alkoxy function. $R^{III}$ equal alkoxy in compounds XIII can optionally be transformed into $R^{III}$ equal OH by known methods as boron tribromide in dichloromethane. The transformation of pyridones XIII into pyridines VIIIa bearing a chloro group $R^{VI}$ and optionally a second chloro group $R^V$ can be performed by known methods as by phosphorous pentachloride neat, by mixtures of phosphorous pentachloride and phosphorous oxychloride with and without additional bases and solvents like ethyl-diisopropyl amine and acetonitrile at temperatures between 80° C. and 140° C. Alternatively pyridines VIIIa bearing two trifluoro-methanesulfonyloxy groups $R^V$ and $R^{VI}$ [known for $R^2=NO_2$: U.S. Pat. No. 5352784 A(1994)], can be prepared form pyridones XIII ($R^{III}$ equal OH) and trifluoro-methanesulfonic acid anhydride and a base like triethylamine in an inert solvent like dichloromethane at temperatures between –40° C. and 60° C. Compounds VIIIa with two identical leaving groups $R^V$ and $R^{VI}$ equal to chloro or trifluoro-methanesulfonyloxy groups react with nucleophiles such as primary and secondary alcoholates in solvents like tetrahydrofuran or N,N-dimethylformamide, water (pH 8 to 14) in the presence of a water miscible solvent like tetrahydrofuran or with primary or secondary amines in solvents like dichloromethane, tetrahydrofuran or N,N-dimethylformamide preferentially at room temperature by first substituting $R^V$ by an alkoxy, hydroxy or an amino substituent $R^1$ thus producing compounds VIIIb. Compounds VIIIb with only the $R^{VI}$ leaving group left can then be reacted with secondary amines III at temperatures preferentially between room temperature and 100° C. in the presence of a base like potassium carbonate or triethylamine in solvents like methanol, ethanol, acetonitrile, tetrahydrofuran, acetone, methyl-ethylketone, N,N-dimethylformamide or dimethylsulfoxide leading to derivatives I6.

Scheme VI
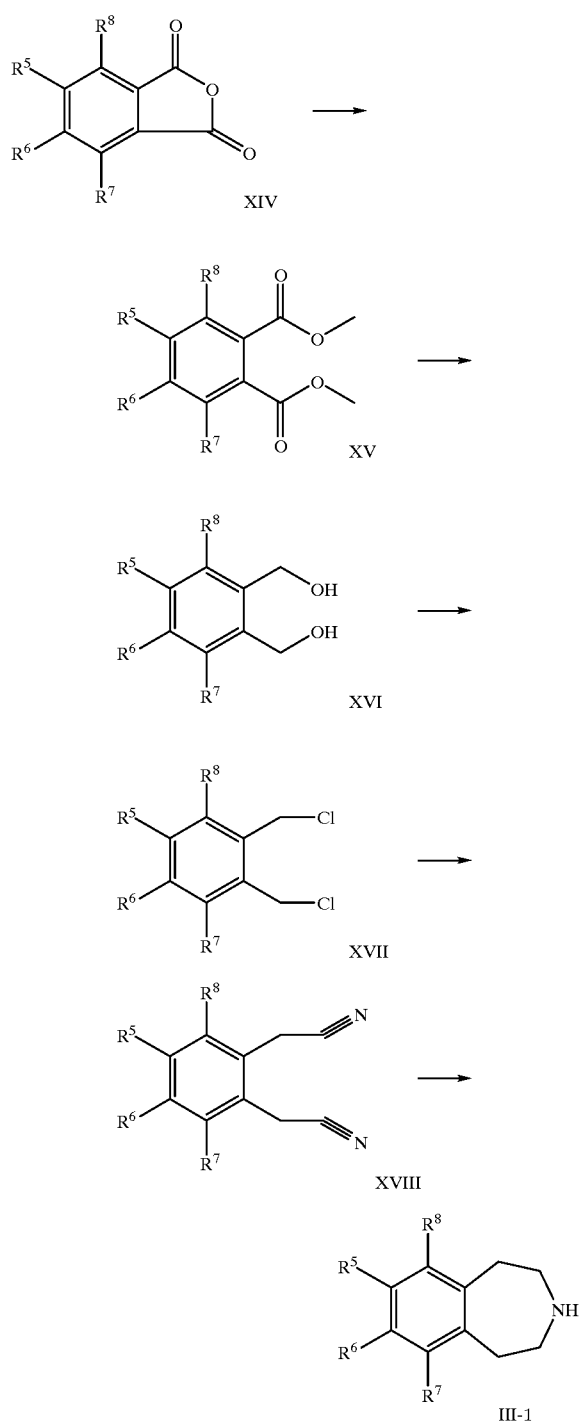
Scheme VII
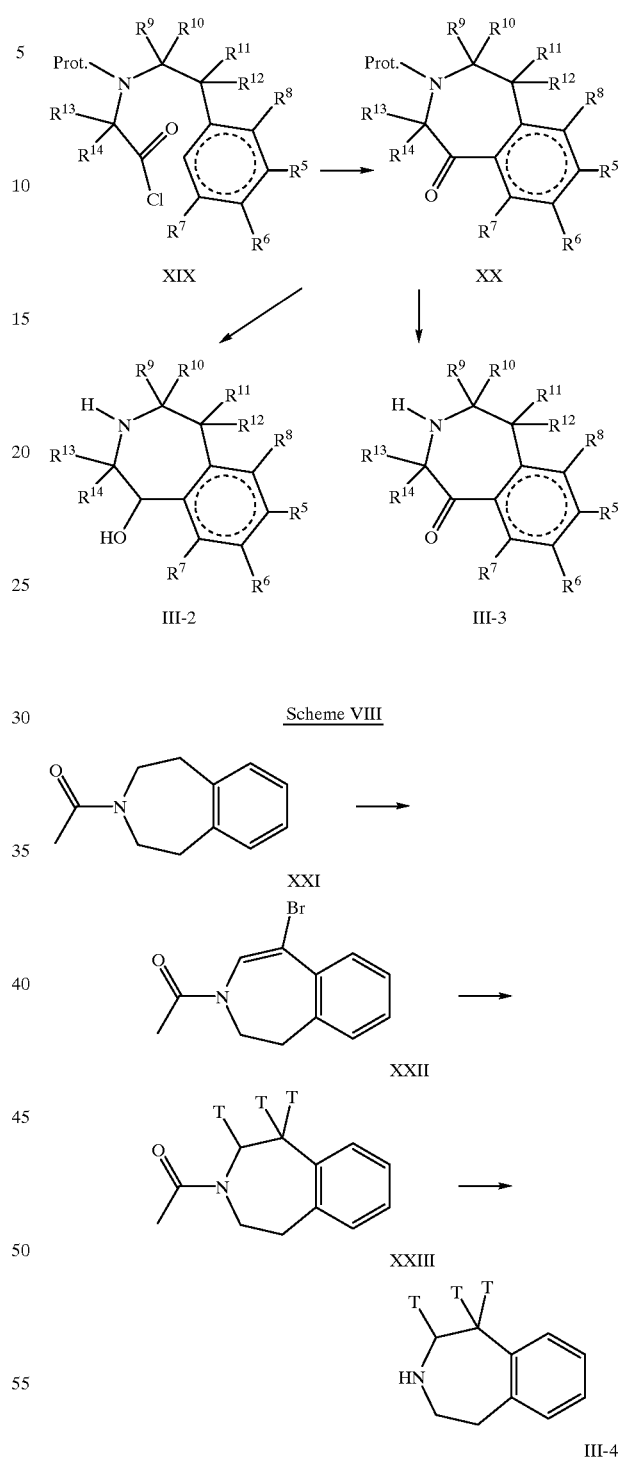
Scheme VIII

Benzazepines III-1 with various substitution patterns in the benzene part optionally bearing additional alkyl substituents in the azepine ring (e.g. 1,1,5,5-tetramethyl-2,3,4,5-tetrahydro-1H-3-benzazepine [Ger. Offen., DE 1921861 691120; CAS 72:31646]) are known [see e.g.: J. Heterocycl. Chem. (1971), 8(5), 779–83]. Alternatively they can be prepared as outlined in Scheme VI [compare J. Med. Chem. (1984) 27, 918–921 describing a similar reaction sequence]: Transformation of optionally substituted phthalic anhydrides XIV into the corresponding dimethylesters using sulfuric acid in methanol at reflux, followed by reduction of the diester with lithiumaluminium hydride in ether or tetrahydrofuran between room temperature and 60° C. and transformation of the so formed diols XVI using thionylchloride in a solvent like toluene or dichloromethane in the presence of a base like pyridine between room temperature and 60° C. yields dichlorides XVII. The further transformation of dichlorides XVII into dinitriles XVIII can be performed using sodium or potassium cyanide in solvents like dimethylsulfoxide or N,N-dimethylformamide between room temperature and 80° C. Reductive cyclisation of dinitriles XVIII into benzazepines III-1 can then be performed with raney nickel in a mixture of conc. aq. ammonia and ethanol at temperatures around 100° C. as described in J. Heterocycl. Chem. (1971), 8(5), 779–83.

Benzazepines III-2 and III-3 bearing a keto respectively hydroxy function at the benzylic position of the azepine ring can be prepared in close analogy to the procedure described for thieno[2,3-d]azepines [J. Heterocyclic Chemistry 22, 1011 (1985)] (Scheme VII): precursor acid chlorides XIX bearing preferentially a tosyloxy protective function at the secondary nitrogen function are cyclized in an inert solvent like 1,2-dichloroethane, dichloromethane or nitrobenzene in the presence of a Lewis acid catalyst like aluminium trichloride, tin tetrachloride or phosphorous pentachloride at temperatures between –40° C. and 80° C. to yield the protected ketones XX. Keto benzazepines III-3 are then prepared by cleavage of N-tosyl function with hydrobromic acid in the presence of a scavenger reagent like phenol in a solvent like ethyl acetate at room temperature, whereas hydroxy benzazepines III-2 can be obtained by simultaneous reduction of the keton function and removal of the N-tosyl protective function by treatment with sodium bis(methoxyethoxy)aluminium-hydride in toluene at reflux.

A labeled amine as the 1,1,2-tritritio-2,3,4,5-tetrahydro-1H-benzo[d]azepine III-4 usable as precursor for the preparation of a labeled compound I according to synthesis schemes I–V can be prepared as outlined in Scheme VIII. The 1-(5-bromo-1,2-dihydro-benzo[d]azepin-3-yl)-ethanone XXII can be prepared by reaction of the 1-(1,2,4,5-tetrahydro-benzo[d]azepin-3-yl)-ethanone XXI [J. Heterocycl. Chem. (1971), 8(5), 779–83] with N-bromosuccinimide in carbon tetrachloride in the presence of a radical initiator like dibenzoylperoxide or 1,1'-azobis-(cyclohexanecarbonitrile) preferentially at reflux. Hydrogenation of the 1-(5-bromo-1,2-dihydro-benzo[d]azepin-3-yl)-ethanone XXII with tritium gas using a palladium or platinum catalyst in solvents methanol, ethanol or an ether like tetrahydrofuran preferentially in the presence of a base like triethylamine gives the 1-(1,1,2-tritritio-1,2,4,5-tetrahydro-benzo[d]azepin-3-yl)-ethanone XXIII which can be converted into the 1-(1,1,2-tritritio-1,2,4,5-tetrahydro-benzo[d]azepin-3-yl)-ethanone III-4 with conc. aq. hydrochloric acid in methanol.

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation or pharmaceutically acceptable salts of acidic compounds of formula I.

The compounds of formula I and their pharmaceutically acceptable salts are, as already mentioned above, metabotropic glutamate receptor antagonists and can be used for the treatment or prevention of acute and/or chronic neurological disorders, such as epilepsy, stroke, chronic and acute pain, psychosis, schizophrenia, Alzheimer's disease, cognitive disorders, memory deficits and psychosis. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression. Thus, this invention includes a method for preventing acute and chronic neurological disorders which comprises administering to the affected patient an amount of the compound of formula I effective to prevent the disorder, and a method for treating acute and chronic neurological disorders which comprises administering to the affected patient an amount of the compound of formula I effective to treat the disorder.

The compounds of the present invention are group I mGluR antagonists, as is demonstrated by the assays below.

a) Functional Assay for the Characterization of mGluR 1 Antagonistic Properties cDNA encoding rat mGluR1a receptor obtained from Prof. S. Nakanishi (Kyoto, Japan) was transiently transfected into HEK-EBNA cells using a procedure described by Schlaeger et. al., New Dev. New Appl. Anim. Cell Techn., Proc. ESACT Meet., 15$^{th}$ (1998), 105–112 and 117–120. [$Ca^{2+}$]i measurements were performed on mGluR1a transfected HEK-EBNA cells after incubation of the cells with Fluo-3 AM (0.5 $\mu$M final concentration) for 1 hour at 37° C. followed by 4 washes with assay buffer (DMEM supplemented with Hank's salt and 20 mM HEPES. [$Ca^{2+}$]i measurements were done using a fluorometric imaging plate reader (FLIPR, Molecular Devices Corporation, La Jolla, Calif., USA). 10 $\mu$M glutamate as agonist was used to evaluate the potency of the antagonists.

Increasing concentrations of antagonists were applied to the cells 5 minutes prior to the application of the agonist. The inhibition (antagonists) curves were fitted with a four parameter logistic equation giving $IC_{50}$, and Hill coefficient using the iterative nonlinear curve fitting software Origin (Microcal Software Inc., Northampton, Mass., USA). The preferred compounds ave an $IC_{50}$ range of 0.001–1.00 $\mu$M (F-$IC_{50}$).

In the table below are shown some specific activity data of preferred compounds determined using functional assay a) (F-$IC_{50}$) above and binding assay b) (B-$IC_{50}$) below:

| Example | F-IC$_{50}$ ($\mu$M) | B-IC$_{50}$ ($\mu$M) |
|---|---|---|
| 220 | 0.038 | 0.002 |
| 30 | 0.009 | 0.003 |
| 190 | 0.20 | 0.007 |
| 154 | 0.21 | 0.01 |
| 78 | 0.026 | 0.011 |
| 249 | 0.023 | 0.011 |
| 25 | 0.005 | 0.015 |
| 11 | 0.008 | 0.018 |
| 214 | 0.12 | 0.020 |
| 132 | 0.014 | 0.080 |
| 174 | 0.97 | 0.088 |
| 17 | 0.088 | 0.33 |
| 126 | 0.10 | 0.72. | b) Binding Assay for the Characterization of mGluR 1 Antagonistic Properties

Binding assay with tritiated 1-ethyl-2-methyl-6-oxo-4-(1,1,2-tritritio-1,2,4,5-tetrahydro-benzo[d]azepin-3-yl)-1,6-dihydro-pyrimidine-5-carbonitrile: HEK 293 cells were transiently transfected with the rat mGluR1a receptor. The cells were collected and washed 3 times with PBS. The cell pellets were frozen at −80° C. Membranes were prepared from HEK 293 cells transfected with the rat mGluR1a receptor and used in the binding experiments at 10 $\mu$g proteins per assay after resuspension in a HEPES NaOH 20 mM, pH=7.4 binding buffer. 1-Ethyl-2-methyl-6-oxo-4-(1,1,2-tritritio-1,2,4,5-tetrahydro-benzo[d]azepin-3-yl)-1,6-dihydo-pyrimidine-5-carbonitrile (S.A 33.4Ci/mmol) was used at 3 nM final concentration. The incubation with variable concentrations of potential inhibitors was performed for 1 hour at room temperature, the incubate was then filtered onto GF/B glass fiber filter preincubated 1 hour in PEI 0,1% and washed 3 times with 1 ml of cold binding buffer. The radioactivity retained on the unifilter 96 was counted using a Topcount $\beta$ counter. After correction for non specific binding the data were normalized and the IC$_{50}$ value calculated using a 4 parameters logistic equation which was fitted to the inhibition curve. The preferred compounds have an IC$_{50}$ range of 0.001–1.00 $\mu$M (B-IC$_{50}$).

Accordingly, this invention includes a method for detecting binding to the metabotropic glutamate receptor by performing a binding assay using a compound of formula I where one or more of $R^{13}$, $R^{14}$, $R^{15}$, and $R^{16}$ is tritium for competitive binding, preferably the compound of formula I is 1-ethyl-2-methyl-6-oxo-4-(1,1,2-tritritio-1,2,4,5-tetrahydro-benzo[d]azepin-3-yl)-1,6-dihydro-pyrimidine-5-carbonitrile.

Also part of this invention is a kit for performing a binding assay which includes a compound of formula I where one or more of $R^{13}$, $R^{14}$, $R^{15}$, and $R^{16}$ is tritium, metabotropic glutamate receptor, and buffers, and any other relevant kit components for this type of assay.

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Accordingly, this invention includes a pharmaceutical composition comprising a compound of formula I as well as pharmaceutically acceptable salts in their racemic and optically active form and pharmaceutically acceptable excipients.

As mentioned earlier, medicaments containing a compound of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

Finally, as mentioned earlier, the use of compounds of formula I and of pharmaceutically acceptable salts thereof for the production of medicaments, especially for the control or prevention of acute and/or chronic neurological disorders of the aforementioned kind, is also an object of the invention.

This invention will be better understood from the following examples, which are for purposes of illustration and are not intended to limit the invention defined in the claims that follow thereafter.

EXAMPLE 1

2-Methyl-5-nitro-6-(1,2,4,5-tetrahydro-benzo[d]azepin-3-yl)-pyrimidin-4-ol

A suspension of 2.0 g (9.8 mmol) of 2-methyl-4-methoxy-5-nitro-6-chloro-pyrimidine [Helv. (1958), 41, 1806], 1.98 g (10.8 mmol) 2,3,4,5-tetrahydro-1H-benzo[d]azepine hydrochloride [J. Heterocycl. Chem. (1971), 8(5), 779–83] and 4.08 g (29.5 mmol) potassium carbonate in 40 ml N,N-dimethylformamide was stirred at 120° C. for 2 hours. The reaction mixture was then allowed to cool to room temperature, poured into 150 ml of an ice/water mixture and extracted three times with 200 ml of dichloromethane. The combined organic phases were washed twice with 100 ml of water, dried over magnesium sulphate, evaporated under reduced pressure and dried in a high vacuum. Crystallization from ethyl acetate/methanol gave 1.95 g (6.5 mmol), 66.1%, 2-methyl-5-nitro-6-(1,2,4,5-tetrahydro-benzo[d]azepin-3-yl)-pyrimidin-4-ol as a yellow solid; m.p. >200° C.; MS: [M+H]$^+$=301.

EXAMPLE 2

3-Ethyl-2-methyl-5-nitro-6-(1,2,4,5-tetrahydro-benzo[d]azepin-3-yl)-3H-pyrimidin-4-one From 2-methyl-5-nitro-6-(1,2,4,5-tetrahydro-benzo[d]azepin-3-yl)-pyrimidin-4-ol and iodoethane, potassium carbonate in N,N-dimethylformamide (r.t.), yellow solid; m.p. 145–147° C.; MS: [M+H]$^+$=329; see example 3.

EXAMPLE 3

3-(6-Ethoxy-2-methyl-5-nitro-pyrimidin-4-yl)-2,3,4,5-tetrahydro-1H-benzo[d]azepine A suspension of 0.30 g (1.0 mmol) of 2-methyl-5-nitro-6-(1,2,4,5-tetrahydro-benzo[d]azepin-3-yl)-pyrimidin-4-ol (example 1), 0.24 g (1.5 mmol) ethyl iodide and 0.28 g (2.0 mmol) potassium carbonate in 10.0 ml N,N-dimethylformamide was stirred at room temperature for 24 h. The reaction mixture was then poured into 50 ml of an ice/water mixture and extracted three times with 100 ml of dichloromethane. The combined organic phases were washed twice with 50 ml of water, dried over magnesium sulphate, evaporated under reduced pressure and dried in a high vacuum. The thus obtained crude product was purified by chromatography on silica gel using a 9:1 to 1:1 v/v mixture of hexane and ethyl acetate as eluent to yield 0.245 g (0.746 mmol), 74.6 %, of 3-ethyl-2-methyl-5-nitro-6-(1,2,4,5-tetrahydro-benzo[d]azepin-3-yl)-3H-pyrimidin-4-one as yellow solid; m.p. 145–147° C.; MS: [M+H]$^+$=329; and 0.070 g (0.213 mmol), 21.3%, of 3-(6-ethoxy-2-methyl-5-nitro-pyrimidin-4-yl)-2,3,4,5-tetrahydro-1H-benzo[d]azepine as yellow oil; MS: [M+H]$^+$=329.

EXAMPLE 4

3-(6-Methoxy-2-methyl-5-nitro-pyrimidin-4-yl)-2,3,4,5-tetrahydro-1H-benzo[d]azepine A solution of 0.204 g (1.0 mmol) of 2-methyl-4-methoxy-5-nitro-6-chloro-pyrimidine [Helv. (1958), 41, 1806], 0.20 g (1.1 mmol) 2,3,4,5-tetrahydro-1H-benzo[d]azepine hydrochloride [J. Heterocycl. Chem. (1971), 8(5), 779–83] and 0.30 g (3.0 mmol) triethylamine in 10.0 ml N,N-dimethylformamide was stirred at room temperature for 60 h. The reaction mixture was then poured into 50 ml of an ice/water mixture and extracted three times with 60 ml of dichloromethane. The combined organic phases were washed twice with 50 ml of water, dried over magnesium sulphate, evaporated under reduced pressure and dried in a high vacuum. The residue obtained was then crystallized from dichloromethane/hexane to yield 0.28 g (0.9 mmol), 90%,3-(6-methoxy-2-methyl-5-nitro-pyrimidin-4-yl)-2,3,4,5-tetrahydro-1H-benzo[d]azepine as a yellow solid; m.p. 123–128° C.

EXAMPLE 5

2,3-Dimethyl-5-nitro-6-(1,2,4,5-tetrahydro-benzo[d]azepin-3-yl)-3H-pyrimidin-4-one In analogy to the procedure described in example 3, the 2-methyl-5-nitro-6-(1,2,4,5-tetrahydro-benzo[d]azepin-3-yl)-pyrimidin-4-ol was treated with methyl iodide in N,N-dimethylformamide in the presence of potassium carbonate to yield the 2,3-dimethyl-5-nitro-6-(1,2,4,5-tetrahydro-benzo[d]azepin-3-yl)-3H-pyrimidin-4-one as yellow foam; MS: [M+H]$^+$=315.

EXAMPLE 6

3-Butyl-2-methyl-5-nitro-6-(1,2,4,5-tetrahydro-benzo[d]azepin-3-yl)-3H-pyrimidin-4-one From 2-methyl-5-nitro-6-(1,2,4,5-tetrahydro-benzo[d]azepin-3-yl)-pyrimidin-4-ol and 1-iodobutane, potassium carbonate in DMF (r.t.) yellow solid; m.p. 158–161° C.; MS: [M+H]$^+$=357; see example 7.

EXAMPLE 7

3-(6-Butoxy-2-methyl-5-nitro-pyrimidin-4-yl)-2,3,4,5-tetrahydro-1H-benzo[d]azepine In analogy to the procedure described in example 3 the 2-methyl-5-nitro-6-(1,2,4,5-tetrahydro-benzo[d]azepin-3-yl)-pyrimidin-4-ol was treated with 1-iodobutane in N,N-dimethylformamide in the presence of potassium carbonate to yield the 3-butyl-2-methyl-5-nitro-6-(1,2,4,5-tetrahydro-benzo[d]azepin-3-yl)-3H-pyrimidin-4-one as yellow solid; m.p. 158–161° C.; MS: [M+H]$^+$=357; and the 3-(6-butoxy-2-methyl-5-nitro-pyrimidin-4-yl)-2,3,4,5-tetrahydro-1H-benzo[d]azepine as yellow oil; MS: [M+H]$^+$=357.

EXAMPLE 8

3-Isobutyl-2-methyl-5-nitro-6-(1,2,4,5-tetrahydro-benzo[d]azepin-3-yl)-3H-pyrimidin-4-one In analogy to the procedure described in example 3 the 2-methyl-5-nitro-6-(1,2,4,5-tetrahydro-benzo[d]azepin-3-yl)-pyrimidin-4-ol was treated with 1-iodo-2-methyl-propane in N,N-dimethylformamide at 80° C. in the presence of potassium carbonate to yield the 3-isobutyl-2-methyl-5-nitro-6-(1,2,4,5-tetrahydro-benzo[d]azepin-3-yl)-3H-pyrimidin-4-one as light brown oil; MS: [M+H]$^+$=357.

EXAMPLE 9

3-Isopropyl-2-methyl-5-nitro-6-(1,2,4,5-tetrahydro-benzo[d]azepin-3-yl)-3H-pyrimidin-4-one In analogy to the procedure described in example 3 the 2-methyl-5-nitro-6-(1,2,4,5-tetrahydro-benzo[d]azepin-3-yl)-pyrimidin-4-ol was treated with 2-iodopropane in N,N-dimethylformamide in the presence of potassium carbonate to yield the 3-isopropyl-2-methyl-5-nitro-6-(1,2,4,5-tetrahydro-benzo[d]azepin-3-yl)-3H-pyrimidin-4-one as yellow oil; MS: [M+H]$^+$=343.

EXAMPLE 10

3-(2-Fluoro-etbyl)-2-methyl-5-nitro-6-(1,2,4,5-tetrahydro-benzo[d]azepin-3-yl)-3H-pyrimidin-4-one In analogy to the procedure described in example 3 the 2-methyl-5-nitro-6-(1,2,4,5-tetrahydro-benzo[d]azepin-3-yl)-pyrimidin-4-ol was treated with 1-bromo-2-fluoroethane in N,N-dimethylformamide in the presence of potassium carbonate at 50° C. to yield the 3-(2-fluoro-ethyl)-2-methyl-5-nitro-6-(1,2,4,5-tetrahydro-benzo[d]azepin-3-yl)-3H-pyrimidin one as yellow oil; MS: [M+H]$^+$=347.

EXAMPLE 11

2-Methyl-5-nitro-6-(1,2,4,5-tetrahydro-benzo[d]azepin-3-y)-3-(2,2,2-trifluoro-ethyl)-3H-pyrimidin-4-one In analogy to the procedure described in example 3 the 2-methyl-5-nitro-6-(1,2,4,5-tetrahydro-benzo[d]azepin-3- yl)-pyrimidin-4-ol was treated with 2,2,2-trifluoroethyl iodide in N,N-dimethylformamide in the presence of potassium carbonate at 80° C. to yield the 2-methyl-5-nitro-6-(1, 2,4,5-tetrahydro-benzo[d]azepin-3-yl)-3-(2,2,2-trifluoroethyl)-3H-pyrimidin-4-one as light brown oil; MS: [M+H]$^+$=383.

EXAMPLE 12

2-Methyl-5-nitro-3-propyl-6-(1,2,4,5-tetrahydro-benzo[d]azepin-3-yl)-3H-pyrimidin-4-one In analogy to the procedure described in example 3 the 2-methyl-5-nitro-6-(1,2,4,5-tetrahydro-benzo[d]azepin-3-yl)-pyrimidin-4-ol was treated with 1-chloropropane in N,N-dimethylformamide in the presence of potassium carbonate at 50° C. to yield 2-methyl-5-nitro-3-propyl-6-(1,2,4,5-tetrahydro-benzo[d]azepin-3-yl)-3H-pyrimidin-4-one as yellow solid; m.p. 164–170° C.; MS: [M+H]$^+$=343.

EXAMPLE 13

2-Amino-6-oxo-4-(1,2,4,5-tetrahydro-benzo[d]azepin-3-yl)-1,6-dihydro-pyrimidine-5-carbonitrile a) A solution of 2.13 g (9.80 mmol) of ethyl 2-cyano-3,3-bis(methylthio)acrylate and 1.80 g (9.80 mmol) 2,3,4,5-tetrahydro-1H-benzo[d]azepine hydrochloride [J. Heterocycl. Chem. (1971), 8(5), 779–83], 1.19 g (11.8 mmol) triethylamine and 0.5 g (3.6 mmol) potassium carbonate in 15 ml of ethanol was heated at reflux for 8 h. The reaction mixture was then evaporated and the residue chormatographed on silica gel using a 97:3 v/v mixture of dichloromethane and ether as eluent. Thus, 2.0 g (6.3 mmol), 64 %, of E and/or Z 2-cyano-3-methylsulfanyl-3-(1,2,4,5-tetrahydro-benzo[d]azepin-3-yl)-acrylic acid ethyl ester were obtained as a yellowish solid; m.p. 88–93° C.; MS: [M]$^+$=316.

b) A solution of 0.253 g (0.80 mmol) of E and/or Z 2-cyano-3-methylsulfanyl-3-(1,2,4,5-tetrahydro-benzo[d]azepin-3-yl)-acrylic acid ethyl ester, 0.199 g (1.60 mmol) guanidine nitrate and 0.376 g (2.40 mmol) 1,8-diazabicyclo[5.4.0]undec-7-ene in 1.0 ml of N,N-dimethylformamide was heated at 100° C. for 2 h. Then, the reaction mixture was poured into 10 ml of ice-water, acidified with 1N hydrogen chloride and the precipitate formed filtered off and washed with water followed by ether. There were thus obtained 0.180 g (0.64 mmol), 80%, of 2-amino-6-oxo-4-(1,2,4,5-tetrahydro-benzo[d]azepin-3-yl)-1,6-dihydro-pyrimidine-5-carbonitrile as a colorless solid; m.p. >200° C.; MS: [M]$^+$=281.

EXAMPLE 14

2,4-Dioxo-6-(1,2,4,5-tetrahydro-benzo[d]azepin-3-yl)-1,2,3,4-tetrahydro-pyrimidine-5-carbonitrile A solution of 0.158 g (0.50 mmol) of Z and/or E 2-cyano-3-methylsulfanyl-3-(1,2,4,5-tetrahydro-benzo[d]azepin-3-yl)-acrylic acid ethyl ester [example 13 a)], 0.142 g (0.50 mmol) of S-methylthiourea sulfate and 0.228 g (1.50 mmol) 1,8-diazabicyclo[5.4.0]undec-7-en in 1.0 ml N,N-dimethylformamide was stirred at 100° C. for 3 hours. The reaction mixture was then poured into 50 ml of ice-water and filtered off, the filtrate was acidified with 1N hydrogen chloride and filtered again. The combined residues were chromatographed on silica gel using a 2:1 v/v mixture of dichloromethane and ethyl acetate as eluent. There were thus obtained 0.063 g (0.192 mmol), 38%, of Z and/or E 2-cyano-3-(1,2,4,5-tetrahydro-benzo[d]azepin-3-yl)-3-ureido-acrylic acid ethyl ester as colorless solid; m.p.183–186° C.; MS: [M]$^+$=328; and 0.0087 g (0.031 mmol), 6.1%, of 2,4-dioxo-6-(1,2,4,5-tetrahydro-benzo[d]azepin-3-yl)-1,2,3,4-tetrahydro-pyrimidine-5-carbonitrile as colorless solid; m.p. >200° C.; MS: [M+H]$^+$=283.

EXAMPLE 15

6-Oxo-4-(1,2,4,5-tetrahydro-benzo[d]azepin-3-yl)-1 6-dihydro-pyrimidine-5-carbonitrile 0.070 g (3.0 mmol) sodium were dissolved in 8.0 ml of ethanol, then 0.316 g (1.0 mmol) of Z and/or E 2-cyano-3-methylsulfanyl-3-(1,2,4,5-tetrahydro-benzo[d]azepin-3-yl)-acrylic acid ethyl ester [example 13 a)] and 0.164 g (2.0 mmol) of formamidine hydrochloride were added and the reaction mixture heated under reflux for 4 h. After evaporation of the solvent, the residue was treated with 30 ml of ice-water followed by 1N hydrogen chloride and extracted three times with 50 ml of a 95:5 v/v mixture of dichloromethane and methanol. The combined organic extracts were dried over magnesium sulfate and evaporated again. The residue formed was then chromatographed on silica gel using a 98:2 v/v mixture of dichloromethane and methanol as eluent. Thus yielding 0.144 g (0.054 mmol), 54%, of 6-oxo-4-(1,2,4,5-tetrahydro-benzo[d]azepin-3-yl)-1,6-dihydro-pyrimidine-5-carbonitrile as colorless solid; m.p. >200° C.; MS: [M]$^+$=266.

EXAMPLE 16

4-Oxo-6-(1,2,4,5-tetrahydro-benzo[d]azepin-3-yl)-2-thioxo-1,2,3,4-tetrahydro-pyrimidine-5-carbonitrile In analogy to the procedure described in example 15 the Z and/or E 2-cyano-3-methylsulfanyl-3-(1,2,4,5-tetrahydro-benzo[d]azepin-3-yl)-acrylic acid ethyl ester [example 13 a)] and thiourea dissolved in ethanol where heated at reflux in the presence of sodium ethylate to yield the 4-oxo-6-(1, 2,4,5-tetrahydro-benzo[d]azepin-3-yl)-2-thioxo-1,2,3,4-tetrahydro-pyrimidine-5-carbonitrile as colorless solid; m.p. >200° C.; MS: [M]$^+$=299.

EXAMPLE 17

2-Methyl-6-oxo-4-(1,2,4,5-tetrahydro-benzo[d]azepin-3-yl)-1,6-dihydro-pyrimidine-5-carbonitrile A solution of 0.158 g (0.50 mmol) of Z and/or E 2-cyano-3-methylsulfanyl-3-(1,2,4,5-tetrahydro-benzo[d]azepin-3-yl)-acrylic acid ethyl ester [example 13 a)], 0.0975 g (1.0 mmol) acetamidine hydrochloride and 0.235 g (1.5 mmol) 1,8-diazabicyclo[5.4.0]undec-7-en in 1.0 ml N,N-dimethylformamide was stirred at 100° C. for 2 hours. The reaction mixture was then poured into 30 ml of ice-water and acidified with 1N hydrogen chloride. The residue formed was filtered off and then chromatographed on silica gel using a 95:5 v/v mixture of dichloromethane and methanol as eluent. There was thus obtained 0.0965 g (0.34 mmol), 69%, of 2-methyl-6-oxo-4-(1,2,4,5-tetrahydro-benzo[d]azepin-3-yl)-1,6-dihydro-pyrimidine-5-carbonitrile as colorless solid; m.p. >200° C.; MS: [M]$^+$=281.

EXAMPLE 18

2-Cyclopropyl-6-oxo-4-(1,2,4,5-tetrahydro-benzo[d]azepin-3-yl)-1,6-dihydro-pyrimidine-5-carbonitrile In analogy to the procedure described in example 15 the Z and/or E 2-cyano-3-methylsulfanyl-3-(1,2,4,5-tetrahydrobenzo[d]azepin-3-yl)-acrylic acid ethyl ester [example 13 a)] was treated with cyclopropylcarbamidine hydrochloride in ethanol in the presence of sodium ethylate at reflux to yield the 2-cyclopropyl-6-oxo-4-(1,2,4,5-tetrahydro-benzo[d]azepin-3-yl)-1,6-dihydro-pyrimidine-5-carbonitrile as colorless solid; m.p. >200° C.; MS: [M]$^+$=307.

EXAMPLE 19

2-[5-Cyano-6-oxo-4-(1,2,4,5-tetrahydro-benzo[d]azepin-3-yl)-1,6-dihydro-pyrimidin-2-yl]-acetamide In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with malonamamidine hydrochloride and 1,8-diazabicyclo[5.4.0]undec-7-en in N,N-dimethylformamide at 100° C. to yield the 2-[5-cyano-6-oxo-4-(1,2,4,5-tetrahydro-benzo[d]azepin-3-yl)-1,6-dihydro-pyrimidin-2-yl]-acetamide as light yellow solid; m.p. >200° C.; MS: [M]$^+$=324.

EXAMPLE 20

6-Oxo-2-phenylsulfanylmethyl-4-(1,2,4,5-tetrahydro-benzo[d]azepin-3-yl)-1,6-dihydro-pyrimidine-5-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with 2-(phenylthio)acetamidine hydrochloride and 1,8-diazabicyclo[5.4.0]undec-7-en in N,N-dimethylformamide at 100° C. to yield the 6-oxo-2-phenylsulfanylmethyl-4-(1,2,4,5-tetrahydro-benzo[d]azepin-3-yl)-1,6-dihydro-pyrimidine-5-carbonitrile as colorless solid; m.p. 189–194° C.; MS: [M+H]$^+$=389.

EXAMPLE 21

2-Dimethylamino-6-oxo-4-(1,2,4,5-tetrahydro-benzo[d]azepin-3-yl)-1,6-dihydro-pyrimidine-5-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 -a)] was treated with 1,1-dimethyl-guanidine-sulfate and 1,8-diazabicyclo[5.4.0]undec-7-en in N,N-dimethylformamide at 100° C. to yield the 2-dimetbylamino-6-oxo-4-(1,2,4,5-tetrahydro-benzo[d]azepin-3-yl)-1,6-dihydro-pyrimidine-5-carbonitrile as colorless solid; m.p. >200° C.; MS: [M+H]$^+$=310.

EXAMPLE 22

2-[2-(1,3-Dioxo-1,3-dihydro-isoindol-2-yl)-ethyl]-6-oxo-4-(1,2,4,5-tetrahydro-benzo[d]azepin-3-yl)-1,6-dihydro-pyrimidine-5-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with 3-(1,3-dioxo-1,3-dihydro-isoindol-2-yl)-propionamidine hydrochloride [PCT Int. Appl. WO 9503305 A1 950202; CA 123:256545] and 1,8-diazabicyclot5.4.0]undec-7-en in N,N-dimethylformamide at 100° C. to yield the 2–12-(l,3-dioxo-1,3-dihydro-isoindol-2-yl)-ethyl]-6-oxo-4-(1,2,4,5-tetrahydro-benzo[d]azepin-3-yl)-1,6-dihydro-pyrimidine-5-carbonitrile as colorless solid; m.p. >200° C.; MS: [M+H]$^+$=440.

EXAMPLE 23

6-Oxo-2-propyl-4-(1,2,4,5-tetrahydro-benzo[d]azepin-3-yl)-1,6-dihydro-pyrimidine-5-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with butyramidine hydrochloride and 1,8-diazabicyclo[5.4.0]undec-7-en in N,N-dimethylformamide at 100° C. to yield 6-oxo-2-propyl-4-(1,2,4,5-tetrahydro-benzo[d]azepin-3-yl)-1,6-dihydro-pyrimidine-5-carbonitrile as colorless solid; m.p. 191–193° C.; MS: [M+H]$^+$=309.

EXAMPLE 24

2-(2-Hydroxy-ethyl)-6-oxo-4-(1,2,4,5-tetrahydro-benzo[d]azepin-3-yl)-1,6-dihydro-pyrimidine-5-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with 3-hydroxy-propionamidine hydrochloride (1:1) [Tetrahedron Lett. (1990), 31(14), 1969–72] and 1,8-diazabicyclo[5.4.0]undec-7-en in N,N-dimethylformamid at 100° C. to yield the 2-(2-hydroxy-ethyl)-6-oxo-4-(1,2,4,5-tetrahydro-benzo[d]azepin-3-yl)-1,6-dihydro-pyrimidine-5-carbonitrile as light yellow solid; m.p. 183.5–188° C.; MS: [M+H]$^+$=311.

EXAMPLE 25

2-Ethylamino-6-oxo-4-(1,2,4,5-tetrahydro-benzo[d]azepin-3-yl)-1,6-dihydro-pyrimidine-5-carbonitrile In analogy to the procedure described in example 15 the Z and/or E 2-cyano-3-methylsulfanyl-3-(1,2,4,5-tetrahydro-benzo[d]azepin-3-yl)-acrylic acid ethyl ester [example 13 a)] and 1-ethylguanidine sulfate dissolved in ethanol where heated at reflux in the presence of sodium ethylate to yield the 2-ethylamino-6-oxo-4-(1,2,4,5-tetrahydro-benzo[d]azepin-3-yl)-1,6-dihydro-pyrimidine-5-carbonitrile as colorless amorphous solid; MS: [M]$^+$=310.

EXAMPLE 26

1,2-Dimethyl-6-oxo-4-(1,2,4,5-tetrahydro-benzo[d]azepin-3-yl)-1,6-dihydro-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with methyl iodide in N,N-dimethylformamide in the presence of potassium carbonate to yield the 1,2-dimethyl-6-oxo-4-(1,2,4,5-tetrahydro-benzo[d]azepin-3-yl)-1,6-dihydro-pyrimidine-5-carbonitrile as pink solid; m.p. 155–158° C.; MS: [M]$^+$=295.

EXAMPLE 27

1-Ethyl-2-methyl-6-oxo-4-(1,2,4,5-tetrahydro-benzo[d]azepin-3-yl)-1,6-dihydro-pyrimidine-5-carbonitrile From 2-methyl-6-oxo-4-(1,2,4,5-tetrahydro-benzo[d]azepin-3-yl)-1,6-dihydro-pyrimidine-5-carbonitrile, iodoethane, N,N-dimethylformamide, potassium carbonate as colorless solid; m.p. 154.5–158° C.; see example 28.

EXAMPLE 28

4-Ethoxy-2-methyl-6-(1,2,4,5-tetrahydro-benzo[d]azepin-3-yl)-pyrimidine-5-carbonitrile In analogy to the procedure described in example 3 the 2-methyl-6-oxo-4-(1,2,4,5-tetrahydro-benzo[d]azepin-3- yl)-1,6-dihydro-pyrimidine-5-carbonitrile (example 17) was treated with iodoethane in N,N-dimethylformamide in the presence of potassium carbonate to yield the 4-ethoxy-2-methyl-6-(1,2,4,5-tetrahydro-benzo[d]azepin-3-yl)-pyrimidine-5-carbonitrile as colorless solid; m.p. 106–109° C.; MS: [M+H]$^+$=309; and the 1-ethyl-2-methyl-6-oxo-4-(1,2,4,5-tetrahydro-benzo[d]azepin-3-yl)-1,6-dihydro-pyrimidine-5-carbonitrile as colorless solid; m.p. 154.5–158° C.

EXAMPLE 29

2-Amino-4-ethoxy-6-(1,2,4,5-tetrahydro-benzo[d]azepin-3-yl)-pyrimidine-5-carbonitrile From 2-amino-6-oxo-4-(1,2,4,5-tetrahydro-benzo[d]azepin-3-yl)-1,6-dihydro-pyrimidine-5-carbonitrile, potassium carbonate, iodoethane, N,N-dimethylformamide, colorless amorphous solid; MS: [M+H]$^+$=310; see example 31.

EXAMPLE 30

2-Amino-1-ethyl-6-oxo-4-(1,2,4,5-tetrahydro-benzo[d]azepin-3-yl)-1,6-dihydro-pyrimidine-5-carbonitrile From 2-amino -6-oxo-4-(1,2,4,5-tetrahydro-benzo[d]azepin-3-yl)-1,6-dihydro-pyrimidine-5-carbonitrile, potassium carbonate, iodoethane, N,N-dimethylformamide, colorless solid; m.p. 195–203° C.; MS: [M+H]$^+$=310; see example 31.

EXAMPLE 31

1-Ethyl-2-ethylamino-6-oxo-4-(1,2,4,5-tetrahydro-benzo[d]azepin-3-yl)-1,6-dihydro-pyrimidine-5-carbonitrile In analogy to the procedure described in example 3 the 2-amino-6-oxo-4-(1,2,4,5-tetrahydro-benzo[d]azepin-3-yl)-1,6-dihydro-pyrimidine-5-carbonitrile [example 13 b)] was treated with iodoethane in N,N-dimethylformamide in the presence of potassium carbonate to yield the 2-amino-4-ethoxy-6-(1,2,4,5-tetrahydro-benzo[d]azepin-3-yl)-pyrimidine-5-carbonitrile as colorless amorphous solid; MS: [M+H]$^+$=310; the 2-amino-1-ethyl-6-oxo-4-(1,2,4,5-tetrahydro-benzo[d]azepin-3-yl)-1,6-dihydro-pyrimidine-5-carbonitrile as colorless solid; m.p. 195–203° C.; MS: [M+H]$^+$=310; and the 1-ethyl-2-ethylamino-6-oxo-4-(1,2,4,5-tetrahydro-benzo[d]azepin-3-yl)-1,6-dihydro-pyrimidine-5-carbonitrile as colorless amorphous solid; MS: [M+H]$^+$=338.

EXAMPLE 32

1-Cyclopropylmethyl-2-methyl-6-oxo-4-(1,2,4,5-tetrahydro-benzo[d]azepin-3-yl)-1,6-dihydro-pyrimidine-5-carbonitrile From 2-methyl-6-oxo-4-(1,2,4,5-tetrahydro-benzo[d]azepin-3-yl)-1,6-dihydro-pyrimidine-5-carbonitrile, bromomethylcyclopropane, potassium carbonate, N,N-dimethylformamide as colorless solid; m.p. 157–161° C.; MS: [M+H]$^+$=335; see example 33.

EXAMPLE 33

4-Cyclopropylmethoxy-2-methyl-6-(1,2,4,5-tetrahydro-benzo[d]azepin-3-yl)- pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with bromomethylcyclopropane in N,N-dimethylformamide in the presence of potassium carbonate to yield the 1-cyclopropylmethyl-2-methyl-6-oxo-4-(1,2,4,5-tetrahydro-benzo[d]azepin-3-yl)-1,6-dihydro-pyrimidine-5-carbonitrile as colorless solid; m.p. 157–161° C.; MS: [M+H]$^+$=335; and the 4-cyclopropylmethoxy-2-methyl-6-(1,2,4,5-tetrahydro-benzo[d]azepin-3-yl)- pyrimidine-5-carbonitrile as colorless solid; m.p. 119–122° C.; MS: [M+H]$^+$=335.

EXAMPLE 34

1-Allyl-2-methyl-6-oxo-4-(1,2,4,5-tetrahydro-benzo[d]azepin-3-yl)-1,6-dihydro-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with allylbromide in N,N-dimethylformamide in the presence of potassium carbonate to yield the 1-allyl-2-methyl-6-oxo-4-(1,2,4,5-tetrahydro-benzo[d]azepin-3-yl)-1,6-dihydro-pyrimidine-5-carbonitrile as colorless solid; m.p. 141–144° C.; MS: [M+H]$^+$=321.

EXAMPLE 35

1-Cyanomethyl-2-methyl-6-oxo-4-(1,2,4,5-tetrahydro-benzo[d]azepin-3-yl)-1,6-dihydro-pyrimidine-5-carbonitrile From 2-methyl-6-oxo-4-(1,2,4,5-tetrahydro-benzo[d]azepin-3-yl)-1,6-dihydro-pyrimidine-5-carbonitrile, bromoacetonitrile, potassium carbonate, N,N-dimethylformamide, as colorless solid; m.p. >200° C.; MS: [M+H]$^+$=320; see example 36.

EXAMPLE 36

2(4-Cyanomethoxy-2-methyl-6-(1,2,4,5-tetrahydro-benzo[d]azepin-3-yl)-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with bromoacetonitrile in N,N-dimethylformamide in the presence of potassium carbonate to yield the 1-cyanomethyl-2-methyl-6-oxo-4-(1,2,4,5-tetrahydro-benzo[d]azepin-3-yl)-1,6-dihydro-pyrimidine-5-carbonitrile as colorless solid; m.p. >200° C.; MS: [M+H]$^+$=320; and the 4-cyanomethoxy-2-methyl-6-(1,2,4,5-tetrahydro-benzo[d]azepin-3-yl)-pyrimidine-5-carbonitrile as colorless amorphous solid; MS: [M+H]$^+$=320.

EXAMPLE 37

1-(2-Dimethylamino-ethyl)-2-methyl-6-oxo-4-(1,2,4,5-tetrahydro-benzo[d]azepin-3-yl)-1,6-dihydro-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with 1-chloro-2-dimethylaminoethane hydrochloride in N,N-dimethylformamide in the presence of potassium carbonate to yield the 1-(2-dimethylamino-ethyl)-2-methyl-6-oxo-4-(1,2,4,5-tetrahydro-benzo[d]azepin-3-yl)-1,6-dihydro-pyrimidine-5-carbonitrile as colorless solid; m.p. 134–139° C.; MS: [M+H]$^+$=352.

EXAMPLE 38

1-Ethyl-6-oxo-4-(1,2,4,5-tetrahydro-benzo[d]azepin-3-yl)-1,6-dihydro-pyrimidine-5-carbonitrile From 6-oxo-4-(1,2,4,5-tetrahydro-benzo[d]azepin-3-yl)-1,6-dihydro-pyrimidine-5-carbonitrile, iodoethane, potassium carbonate, N,N-dimethylformamide, as yellowish solid; m.p. 138–140° C.; MS: [M+H]$^+$=295; see example 39.

EXAMPLE 39

4-Ethoxy-6-(1,2,4,5-tetrahydro-benzo[d]azepin-3-yl)-pyrimidine-5-carbonitrile

In analogy to the procedure described in example 3 the 6-oxo-4-(1,2,4,5-tetrahydro-benzo[d]azepin-3-yl)-1,6-dihydro-pyrimidine-5-carbonitrile (example 15) was treated with iodoethane in N,N-dimethylformamide in the presence of potassium carbonate to yield the 1-ethyl-6-oxo-4-(1,2,4,5-tetrahydro-benzo[d]azepin-3-yl)-1,6-dihydro-pyrimidine-5-carbonitrile as yellowish solid; m.p. 138–140° C.; MS: [M+H]$^+$=295; and the 4-ethoxy-6-(1,2,4,5-tetrahydro-benzo[d]azepin-3-yl)-pyrimidine-5-carbonitrile as colorless amorphous solid; MS: [M+H]$^+$=295.

EXAMPLE 40

1-Isopropyl-6-oxo-4-(1,2,4,5-tetrahydro-benzo[d]azepin-3-yl)-1,6-dihydro-pyrimidine-5-carbonitrile In analogy to the procedure described in example 3 the 6-oxo-4-(1,2,4,5-tetrahydro-benzo[d]azepin-3-yl)-1,6-dihydro-pyrimidine-5-carbonitrile (example 15) was treated with 2-iodopropane in N,N-dimethylformamide in the presence of potassium carbonate to yield the 1-isopropyl-6-oxo-4-(1,2,4,5-tetrahydro-benzo[d]azepin-3-yl)-1,6-dihydro-pyrimidine-5-carbonitrile as colorless solid; m.p. 152–154° C.; MS: [M+H]$^+$=309.

EXAMPLE 41

1-(2-Hydroxy-ethyl)-6-oxo-4-(1,2,4,5-tetrahydro-benzo[d]azepin-3-yl)-1,6 dihydro-pyrimidine-5-carbonitrile In analogy to the procedure described in example 3 the 6-oxo-4-(1,2,4,5-tetrahydro-benzo[d]azepin-3-yl)-1,6-dihydro-pyrimidine-5-carbonitrile (example 15) was treated with 2-bromoethanol in N,N-dimethylformamide in the presence of potassium carbonate to yield the 1-(2-hydroxy-ethyl)-6-oxo-4-(1,2,4,5-tetrahydro-benzo[d]azepin-3-yl)-1,6dihydro-pyrimidine-5-carbonitrile as light rose solid; m.p. 167–171° C.; MS: [M+H]$^+$=311.

EXAMPLE 42

5-Cyano-6-oxo-4-(1,2,4,5-tetrahydro-benzo[d]azepin-3-yl)-6H1-pyrimidin-1-yl]-acetic acid methyl ester In analogy to the procedure described in example 3 the 6-oxo-4-(1,2,4,5-tetrahydro-benzo[d]azepin-3-yl)-1,6-dihydro-pyrimidine-5-carbonitrile (example 15) was treated with methylbromoacetate in N,N-dimethylformamide in the presence of potassium carbonate to yield the [5-cyano-6-oxo-4-(1,2,4,5-tetrahydro-benzo[d]azepin-3-yl)-6H-pyrimidin-1-yl]-acetic acid methyl ester as light yellow solid; m.p. 156–160° C.; MS: [M+H]$^+$=339.

EXAMPLE 43

1-Methyl-6-oxo-4-(1,2,4,5-tetrahydro-benzo[d]azepin-3-yl)-1,6-dihydro-pyrimidine-5-carbonitrile In analogy to the procedure described in example 3 the 6-oxo-4-(1,2,4,5-tetrahydro-benzo[d]azepin-3-yl)-1,6-dihydro-pyrimidine-5-carbonitrile (example 15) was treated with methyliodide in N,N-dimethylformamide in the presence of potassium carbonate to yield the 1-methyl-6-oxo-4-(1,2,4,5-tetrahydro-benzo[d]azepin-3-yl)-1,6-dihydro-pyrimidine-5-carbonitrile as colorless solid; m.p. 197–203° C.; MS: [M+H]$^+$=281.

EXAMPLE 44

2-Amino-5-nitro-6-(1,2,4,5-tetrahydro-benzo[d]azepin-3-yl)-3H-pyrimidin-4-one

In analogy to the procedure described in example 1 the 2-amino-6-chloro-5-nitro-pyrimidin-4-ol [J. Chem. Soc. 1964, 4769–4774] was treated with the 2,3,4,5-tetrahydro-1H-benzo[d]azepine hydrochloride [J. Heterocycl. Chem. (1971), 8(5), 779–83]in N,N-dimethylformamide/potassiumcarbonate at 140° C. to yield the 2-amino-5-nitro-6-(1,2,4,5-tetrahydro-benzo[d]azepin-3-yl)-3H-pyrimidin-4-one as a yellow solid; m.p. 275° C. (decomposition).

EXAMPLE 45

N-[5-Nitro-6-oxo-4-(1,2,4,5-tetrahydro-benzo[d]azepin-3-yl)-1,6-dihydro-pyrimidin-2-yl]-acetamide A solution of 0.30 g (1.0 mmol) of 2-amino-5-nitro-6-(1,2,4,5-tetrahydro-benzo[d]azepin-3-yl)-3H-pyrimidin-4-one (example 44) in 1.0 ml acetic acid anhydride and 1.0 ml pyridine was stirred for 2 h at 60° C. The reaction mixture was the poured into 25 ml of ice-water and acidified with 1N hydrogen chloride solution. The residue formed was filtered off and washed with water and ether. There was thus obtained 0.302 g (0.88 mmol), 88%, of N-[5-nitro-6-oxo-4-(1,2,4,5-tetrahydro-benzo[d]azepin-3-yl)-1,6-dihydro-pyrimidin-2-yl]-acetamide as yellow solid; m.p. >200° C.; MS: [M]$^+$=344.

EXAMPLE 46

3-(6-Methoxy-5-nitro-pyrimidin-4-yl)-2,3,4,5-tetrahydro-1H-benzo[d]azepine a) A solution of 0.396 g (2.0 mmol) of 4,6-dichloro-5-nitro-pyrimidine and of 0.367 g (2.0 mmol) 2,3,4,5-tetrahydro-1H-benzo[d]azepine hydrochloride [j. Heterocycl. Chem. (1971), 8(5), 779–83] in 30 ml N,N-dimethylformamide was treated slowly at 0° C. to 5° C. with 0.70 ml (5.0 mmol) of triethylamine and the reaction mixture stirred at the same temperature for 2 hours. It was then poured into 50 ml of an ice/water mixture and extracted three times with 100 ml of dichloromethane. The combined organic phases were washed twice with 50 ml of water, dried over magnesium sulphate, evaporated under reduced pressure and dried in a high vacuum. The thus obtained crude product was purified by chromatography on silica gel using a 99:1 v/v mixture of dichloromethane and methanol as eluent to yield 0.54 g (1.78 mmol), 88.9%, of 3-(6-chloro-5-nitro-pyrimidin-4-yl)-2,3,4,5-tetrahydro-1H-benzo[d]azepine as yellow solid; m.p. 165–171° C.; MS: [M+H]$^+$=305.

(b) 0.305 g (1.0 mmol) of 3-(6-chloro-5-nitro-pyrimidin-4-yl)-2,3,4,5-tetrahydro-1H-benzo[d]azepine were suspended in 15 ml of methanol and treated with 0.93 ml (5 mmol) of a solution of sodium methylate in methanol (30%). The reaction mixture was then heated to 60° C. for 20 minutes and stirred at room temperature for 4 hours, then filtered. The crystals obtained were washed with hexane and dried in a high vacuum. There were thus obtained 0.260 g (0.866 mmol), 86.6%, of 3-(6-methoxy-5-nitro-pyrimidin-4-yl)-2,3,4,5-tetrahydro-1H-benzo[d]azepine as yellow solid; m.p. 147–150° C.; MS: [M+H]$^+$=301.

EXAMPLE 47

5-Nitro-6-(1 2,4,5-tetrahydro-benzo[d]azepin-3-yl)-pyrimidin-4-ol a) 0.183 g (1.3 mmol) 4-methoxy-benzylalcohol were dissolved in 10 ml of tetrahydrofuran, then 0.048 g (1.1 mmol) sodium hydride dispersion (55% in mineral oil) added followed by 0.305 g (1.0 mmol) of 3-(6-chloro-5-nitro-pyrimidin-4-yl)-2,3,4,5-tetrahydro-1H-benzo[d]azepine [example 46 (a)] dissolved in 5 ml of tetrahydrofuran. The reaction mixture was then stirred at room temperature for 2 hours, poured into 50 ml of an ice/water mixture and extracted three times with 50 ml of ethyl acetate. The combined organic phases were washed twice with 50 ml of water, dried over magnesium sulphate, evaporated under reduced pressure and dried in a high vacuum. The thus obtained crude product was purified by chromatography on silica gel using dichloromethane as eluent to yield 0.41 g (1.3 mmol), 100%, of 3-[6-(4-methoxy-benzyloxy)-5-nitro-pyrimidin-4-yl]-2,3,4,5-tetrahydro-1H-benzo[d]azepine as yellow solid; m.p. 105–109° C.; MS: [M+H]$^+$=407.

b) 0.10 g (0.25 mmol) of 3-[6-(4-methoxy-benzyloxy)-5-nitro-pyrimidin-4-yl]-2,3,4,5-tetrahydro-1H-benzo[d]azepine were dissolved in 5.0 ml of methanol and treated with 0.63 ml 1.5M hydrogen chloride solution in methanol and the reaction mixture was stirred at room temperature for 2 hours. The crystals formed were filtered off, washed with hexane and dried in a high vacuum to yield 0.069 g (0.241 mmol), 98%, of 5-nitro-6-(1,2,4,5-tetrahydro-benzo[d]azepin-3-yl)-pyrimidin-4-ol as yellow solid; m.p. >200° C.; MS: [M−H]$^-$=285.

EXAMPLE 48

5-Nitro-6-(1,2,4,5-tetrahydro-benzo[d]azepin-3-yl)-pyrimidin-4-ylamine 0.305 g (1.0 mmol) of 3-(6-chloro-5-nitro-pyrimidin-4-yl)-2,3,4,5-tetrahydro-1H-benzo[d]azepine [example 46 (a)] were dissolved in 15 ml of tetrahydrofuran and treated with 0.22 ml of a 25% aqueous ammonia solution and stirred at room temperature for 60 hours. The reaction mixture was then evaporated to dryness and the thus obtained crude product was purified by chromatography on silica gel using a 98:2 v/v mixture of dichloromethane and methanol as eluent to yield 0.219 g (0.768 mmol), 76.8%, of 5-nitro-6-(1,2,4,5-tetrahydro-benzo[d]azepin-3-yl)-pyrimidin-4-ylamine as yellow solid; m.p. >200° C.; MS: [M+H]$^+$=286.

EXAMPLE 49

Methyl-[5-nitro-6-(1,2,4,5-tetrahydro-benzo[d]azepin-3-yl)-pyrimidin-4-yl]-amine In analogy to example 48 the 3-(6-chloro-5-nitro-pyrimidin-4-yl)-2,3,4,5-tetrahydro-1-H-benzo[d]azepine [example 46 (a)] was treated with methylamine solution (40% in H$_2$O) in tetrahydrofuran at room temperature to yield the methyl-[5-nitro-6-(1,2,4,5-tetrahydro-benzo[d]azepin-3-yl)-pyrimidin-4-yl]-amine as yellow solid; m.p. 144–146° C.; MS: [M+H]$^+$=300.

EXAMPLE 50

Cyclopropyl-[5-nitro-6-(1,2,4,5-tetrahydro-benzo[d]azepin-3-yl)-pyrimidin-4-yl]-amine In analogy to example 48 the 3-(6-chloro-5-nitro-pyrimidin-4-yl)-2,3,4,5-tetrahydro-1H-benzo[d]azepine [example 46 (a)] was treated with cyclopropylamine in tetrahydrofuran at room temperature to yield the cyclopropyl-[5-nitro-6-(1,2,4,5-tetrahydro-benzo[d]azepin-3-yl)-pyrimidin-4-yl]-amine as light yellow solid; m.p. 135–138° C.; MS: [M+H]$^+$=326.

EXAMPLE 51

[5-Nitro-6-(1,2,4,5-tetrahydro-benzo[d]azepin-3-yl)-pyrimidin-4-ylsulfanyl]-acetic acid methyl ester In analogy to example 48 the 3-(6-chloro-5-nitro-pyrimidin-4-yl)-2,3,4,5-tetrahydro-1H-benzo[d]azepine [example 46 (a)] was treated with methyl thioglycolate and triethylamine in methanol at reflux to yield the [5-nitro-6-(1,2,4,5-tetrahydro-benzo[d]azepin-3-yl)-pyrimidin-4-ylsulfanyl]-acetic acid methyl ester as yellow sblid; m.p. 113–115° C.; MS: [M+H]$^+$=375.

EXAMPLE 52

6-Methyl-2-(1,2,4,5-tetrahydro-benzo[d]azepin-3-yl)-nicotinonitrile 0.509 g (3.3 mmol) of 2-chloro-3-cyano-6-methylpyridin, 0.551 g (3.0 mmol) of 2,3,4,5-tetrahydro-1H-benzo[d]azepine hydrochloride [J. Heterocycl. Chem. (1971), 8(5), 779–83] and 0.92 g (6.6 mmol) of potassium carbonate were dissolved in 3.0 ml of acetonitrile and heated at reflux for 16 hours. The reaction mixture was then allowed to cool to room temperature, poured into 30 ml of an ice/water mixture and extracted three times with 50 ml of dichloromethane. The combined organic phases were washed twice with 50 ml of water, dried over magnesium sulphate evaporated under reduced pressure and dried in a high vacuum. The thus obtained crude product was purified by chromatography on silica gel using a 4:1 v/v mixture of hexane and ethyl acetate as eluent to yield 0.724 g (2.75 mmol), 91.6%, of 6-methyl-2-(1,2,4,5-tetrahydro-benzo[d]azepin-3-yl)-nicotinonitrile as colorless solid; m.p. 78.5–80.7° C.; MS: [M]$^+$=263.

EXAMPLE 53

2-(1,2,4,5-Tetrahydro-benzo[d]azepin-3-yl)-benzonitrile

In analogy to example 52 the trifluoro-methanesulfonic acid 2-cyano-phenyl ester [J. Org. Chem. (1992), 57(5), 1481–6] and the 2,3,4,5-tetrahydro-1H-benzo[d]azepine hydrochloride [J. Heterocycl. Chem. (1971), 8(5), 779–83] were treated with potassium carbonate in acetonitrile at reflux to yield the 2-(1,2,4,5-tetrahydro-benzo[d]azepin-3-yl)-2(benzonitrile as yellowish solid; m.p. 68–74° C.; MS: [M]$^+$=248.

EXAMPLE 54

3-(3-Nitro-pyridin-2-yl)-2,3,4,5-tetrahydro-1H-benzo[d]azepine

In analogy to example 52 the 2-chlor-3-nitropyridine and the 2,3,4,5-tetrahydro-1H-benzo[d]azepine hydrochloride [J. Heterocycl. Chem. (1971), 8(5), 779–83] were treated with potassium carbonate in acetonitrile at reflux to yield the 3-(3-nitro-pyridin-2-yl)-2,3,4,5-tetrahydro-1H-benzo[d]azepine as yellow solid; m.p. 129–136° C.

EXAMPLE 55

2-(1,2,4,5-Tetrahydro-benzo[d]azepin-3-yl)-nicotinonitrile

In analogy to example 52 the chloronicotinonitrile and the 2,3,4,5-tetrahydro-1H-benzo[d]azepine hydrochloride [J.

Heterocycl. Chem. (1971), 8(5), 779–83] were treated with potassium carbonate in acetonitrile at reflux to yield the 2-(1,2,4,5-tetrahydro-benzo[d]azepin-3-yl)-nicotinonitrile as colorless solid; m.p. 110–112.5° C.; MS: [M]$^+$=249.

EXAMPLE 56

3-(2-Nitro-phenyl)-2,3,4,5-tetrahydro-1H-benzo[d]azepine

In analogy to example 52 the trifluoro-methanesulfonic acid 2-nitro-phenyl ester [J. Org. Chem. (1992), 57(5), 1481–6] and the 2,3,4,5-tetrahydro-1H-benzo[d]azepine hydrochloride [J. Heterocycl. Chem. (1971), 8(5), 779–83] were treated with potassium carbonate in acetonitrile at reflux to yield the 3-(2-nitro-phenyl)-2,3,4,5-tetrahydro-1H-benzo[d]azepine as 3orange oil; MS: [M+H]$^+$=269.

EXAMPLE 57

3-Methyl-2,4-dioxo-6-(1,2,4,5-tetrahydro-benzo[d]azepin-3-yl)-1,2,3,4-tetrahydro-pyrimidine-5-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with O-methylisourea hemisulfate and 1,8-diazabicyclo[5.4.0]undec-7-en in N,N-dimethylformamide at 100° C. to yield the 3-methyl-2,4-dioxo-6-(1,2,4,5-tetrahydro-benzo[d]azepin-3-yl)-1,2,3,4-tetrahydro-pyrimidine-5-carbonitrile as light yellow solid; m.p. >200° C.; MS: [M+H]$^+$=297.

EXAMPLE 58

3-(3,5-Dinitro-pyridin-2-yl)-2,3,4,5-tetrahydro-1H-benzo[d]azepine

In analogy to the procedure described in example 4 the 2-chloro-3,5-dinitro-pyridine and the 2,3,4,5-tetrahydro-1H-benzo[d]azepine hydrochloride [J. Heterocycl. Chem. (1971), 8(5), 779–83] were treated in N,N-dimethylformamide in the presence of triethylamine at room temperature to yield the 3-(3,5-dinitro-pyridin-2-yl)-2,3,4,5-tetrahydro-1H-benzo[d]azepine light yellow solid; m.p. 137–140° C.; MS: [M+H]$^+$=315.

EXAMPLE 59

1-Methoxymethyl-6-oxo-4-(1,2,4,5-tetrahydro-benzo[d]azepin-3-yl)-1,6-dihydro-pyrimidine-5-carbonitrile From 6-oxo-4-(1,2,4,5-tetrahydro-benzo[d]azepin-3-yl)-1,6-dihydro-pyrimidine-5-carbonitrile, chloromethyl-methylether, sodium hydride, N,N-dimethylformamide, as colorless solid; m.p. 160–162.5° C.; MS: [M]$^+$=310; see example 60.

EXAMPLE 60

4-Methoxy-6-(1,2,4,5-tetrahydro-benzo[d]azepin-3-yl)-pyrimidine-5-carbonitrile 0.085 g (0.320 mmol) of 6-oxo-4-(1,2,4,5-tetrahydro-benzo[d]azepin-3-yl)-1,6-dihydro-pyrimidine-5-carbonitrile (example 15) were dissolved in 0.8 ml of N,N-dimethylformamide and treated with 0.023 g (0.5 mmol) of sodium hydride dispersion (55% in mineral oil). Then, 0.041 g (0.5 mmol) chloromethyl-methyl-ether were added at once and the reaction mixture stirred at room temperature for 16 hours, poured into 30 ml of an ice/water mixture, acidified with 1N hydrogen chloride solution and extracted three times with 30 ml of ethyl acetate. The combined organic phases were washed twice with 30 ml of water, dried over magnesium sulphate, evaporated under reduced pressure and dried in a high vacuum. The thus obtained crude product was purified by chromatography on silica gel using a 9:1 v/v mixture of dichloromethane and ether as eluent to yield 0.043 g (0.138 mmol), 43%, 1-methoxymethyl-6-oxo-4-(1,2,4,5-tetrahydro-benzo[d]azepin-3-yl)-1,6-dihydro-pyrimidine-5-carbonitrile as colorless solid; m.p. 160–162.5° C.; MS: [M]$^+$=310; and 0.021 g (0.076 mmol), 24%, 4-methoxy-6-(1,2,4,5-tetrahydro-benzo[d]azepin-3-yl)-pyrimidine-5-carbonitrile colorless solid; m.p. 119–124.5° C.; MS: [M]$^+$=280.

EXAMPLE 61

6-Oxo-1-[3-(2-oxo-azepan-1-yl)-propyl]-4-(1,2,4,5-tetrahydro-benzo[d]azepin-3-yl)-1,6-dihydro-pyrimidine-5-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with formamidine hydrochloride and 1,8-diazabicyclo[5.4.0]undec-7-en in N,N-dimethylformamide at 100° C. to yield the 6-oxo-4-(1,2,4,5-tetrahydro-benzo[d]azepin-3 -yl)-1,6-dihydro-pyrimidine-5-carbonitrile (example 15) and the 6-oxo-1-[3-(2-oxo-azepan-1-yl)-propyl]-4-(1,2,4,5-tetrahydro-benzo[d]azepin-3-yl)-1,6-dihydro-pyrimidine-5-carbonitrile as colorless solid; m.p. 139–140° C.; MS: [M+H]$^+$=420.

EXAMPLE 62

6-(7,8-Dimethoxy-1,2,4,5-tetrahydro-benzo[d]azepin-3-yl)-2-methyl-5-nitro-3H-pyrimidin-4-one In analogy to the procedure described in example 1 the 2-methyl-4-methoxy-5-nitro-6-chloro-pyrimidine [Helv. (1958), 41, 1806] was treated with the 7,8-dimethoxy-2,3,4,5-tetrahydro-1H-benzo[d]azepine hydrochloride [Ann. Chim. (Paris) (1966), 1(5/6), 221–54] in N,N-dimethylformamide/potassium carbonate at 120° C. to yield the 6-(7,8-dimethoxy-1,2,4,5-tetrahydro-benzo[d]azepin-3-yl)-2-methyl-5-nitro-3H-pyrimidin-4-one as a yellow solid; m.p. 268–270° C. (decomposition); MS: [M+H]$^+$=361.

EXAMPLE 63

2-Methyl-5-nitro-6-(5,6,8,9-tetrahydro-1,3-dioxa-7-aza-cyclohepta[f]inden-7-yl)-3H-pyrimidin-4-one In analogy to the procedure described in example 1 the 2-methyl-4-methoxy-5-nitro-6-chloro-pyrimidine [Helv. (1958), 41, 1806] was treated with the 6,7,8,9-tetrahydro-5H-1,3-dioxa-7-aza-cyclohepta[f]indene hydrochloride [J. Heterocycl. Chem. (1972), 9(3), 617–21] in N,N-dimethylformamide/potassium carbonate at 120° C. to yield the 2-methyl-5-nitro-6-(5,6,8,9-tetrahydro-1,3-dioxa-7-aza-cyclohepta[f]inden-7-yl)-3H-pyrimidin-4-one as a light yellow solid; m.p. 258–262° C. (decomposition); MS: [M+H]$^+$=345.

EXAMPLE 64

2-Methyl-5-nitro-6-(7-nitro-1,2,4,5-tetrahydro-benzo[d]azepin-3-yl)-3H-pyrimidin-4-one In analogy to the procedure described in example 4 the 6-bromo-2-methyl-5-nitro-3H-pyrimidin-4-one (prepared from 2-methyl-4-methoxy-5-nitro-6-chloro-pyrimidine [Helv. (1958), 41, 1806] and hydrobromic acid (48% in water) in acetic acid at room temperature) was treated with the 7-nitro-2,3,4,5-tetrahydro-1H-benzo[d]azepine [J. Heterocycl. Chem. (1971), 8(5), 779–83]in N,N-dimethylformamide in the presence of N-ethyl-N,N-diisopropylamine at room temperature to yield the 2-methyl-5-nitro-6-(7-nitro-1,2,4,5 -tetrahydro-benzo[d]azepin-3-yl)-3H-pyrimidin-4-one as yellow solid; m.p. 237–238° C. (decomposition); MS: [M+H]$^+$=346.

EXAMPLE 65

3-(2-Methyl-5-nitro-6-oxo-1,6-dihydro-pyrimidin-4-yl)-2,3,4,5-tetrahydro-1H-benzo[d]azepine-7-sulfonic acid amide In analogy to the procedure described in example 4 the 6-bromo-2-methyl-5-nitro-3H-pyrimidin-4-one (prepared from 2-methyl-4-methoxy-5-nitro-6-chloro-pyrimidine [Helv. (1958), 41, 1806] and hydrobromic acid (48% in water) in acetic acid at room temperature) was treated with the 2,3,4,5-tetrahydro-1H-benzo[d]azepine-7-sulfonic acid amide [Ger. Offen. DE 1921737] in N,N-dimethylformamide in the presence of N-ethyl-N,N-diusopropylamine at room temperature to yield the 3-(2-methyl-5-nitro-6-oxo-1,6-dihydro-pyrimidin-4-yl)-2,3,4,5-tetrahydro-1H-benzo[d]azepine-7-sulfonic acid amide as light yellow solid; m.p. 268–270° C. (decomposition); MS: [M+H]$^+$=380.

EXAMPLE 66

6-(7-Amino-1,2,4,5-tetrahydro-benzo[d]azepin-3-yl)-2-methyl-5-nitro-3H-pyrimidin-4-one In analogy to the procedure described in example 4 the 6-bromo-2-methyl-5-nitro-3H-pyrimidin-4-one (prepared from 2-methyl-4-methoxy-5-nitro-6-chloro-pyrimidine [Helv. (1958), 41, 1806] and hydrobromic acid (48% in water) in acetic acid at room temperature) was treated with the 2,3,4,5-tetrahydro-1H-benzo[d]azepin-7-ylamine [J. Heterocycl. Chem. (1971), 8(5), 779–83] in N,N-dimethylformamide in the presence of N-ethyl-N,N-diisopropylamine at room temperature to yield the 6-(7-amino-1,2,4,5-tetrahydro-benzo[d]azepin-3-yl)-2-methyl-5-nitro-3H-pyrimidin-4-one as yellow solid; m.p. 218–220° C. (decomposition); MS: [M+H]$^+$=316.

EXAMPLE 67

6-Oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile 0.160 g (0.516 mmol) of 2-(2-hydroxy-ethyl)-6-oxo-4-(1,2,4,5-tetrahydro-benzo[d]azepin-3-yl)-1,6-dihydro-pyrimidine-5-carbonitrile (example 24), 0.084 g (1.0 mmol) 3,4-dihydro-2H-pyran and 0.130 g (0.516 mmol) of pyridinium-(toluene-4-sulfonate) were dissolved in 5.0 ml of dichloromethane and stirred for 18 hours at room temperature. Then, the reaction mixture was poured into 30 ml of an ice/dil. aq. sodium bicarbonate mixture and extracted three times with 20 ml of dichloromethane. The combined organic phases were washed twice with 1N HCl solution, twice with dil. aq. sodium bicarbonate solution, dried over magnesium sulphate and evaporated under reduced pressure. There were thus obtained 0.176 g (0.446 mmol), 87%, 6-oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile as colorless solid; m.p. 185–187° C.

EXAMPLE 68

4-Ethoxy-6-(1,2,4,5-tetrahydro-benzo[d]azepin-3-yl)-2-[2-(tetrahydro-pyran-2-yloxy)-ethyl]-pyrimidine-5-carbonitrile From 6-oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile, ethyliodide, potassium carbonate, N,N-dimethylformamide as colorless amorphous solid; MS: [M+H]$^+$=423; see example 69.

EXAMPLE 69

1-Ethyl-6-oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile In analogy to the procedure described in example 3 the 6-oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile (example 67) was treated with ethyliodide in N,N-dimethylformamide in the presence of potassium carbonate to yield the 1-ethyl-6-oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile as colorless amorphous solid; MS: [M+H]$^+$=423; and the 4-ethoxy-6-(1,2,4,5-tetrahydro-benzo[d]azepin-3-yl)-2-[2-(tetrahydro-pyran-2-yloxy)-ethyl]-pyrimidine-5-carbonitrile as colorless amorphous solid; MS: [M+H]$^+$=423.

EXAMPLE 70

1-Ethyl-2-(2-hydroxy-ethyl)-6-oxo-4-(1,2,4,5-tetrahydro-benzo[d]azepin-3-yl)-1,6-dihydro-pyrimidine-5-carbonitrile 0.144 g (0.341 mmol) of 1-ethyl-6-oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile (example 69) were dissolved in 2.5 ml of methanol and treated with 0.45 ml of an 1.5M solution of HCl in methanol. After stirring at room temperature for 30 minutes, 250 mg solid powdered sodium bicarbonate was added and the reaction mixture evaporated to dryness. The thus obtained crude product was purified by chromatography on silica gel using a 95:5 v/v mixture of dichloromethane and methanol as eluent to yield 0.115 g (0.341 mmol), 100%, of 1-ethyl-2-(2-hydroxy-ethyl)-6-oxo-4-(1,2,4,5-tetrahydro-benzo[d]azepin-3-yl)-1,6-dihydro-pyrimidine-5-carbonitrile as colorless solid; MS: [M+H]$^+$=339; m.p. 114–115° C.

EXAMPLE 71

4-Ethoxy-2-(2-hydroxy-ethyl)-6-(1,2,4,5-tetrahydro-benzo[d]azepin-3-yl)-pyrimidine-5-carbonitrile In analogy to the procedure described in example 70 the 4-ethoxy-6-(1,2,4,5-tetrahydro-benzo[d]azepin-3-yl)-2-[2-(tetrahydro-pyran-2-yloxy)-ethyl]-pyrimidine-5-carbonitrile (example 68) was treated with 1.5N HCl in methanol to yield the 4-ethoxy-2-(2-hydroxy-ethyl)-6-(1,2,4,5-tetrahydro-benzo[d]azepin-3-yl)-pyrimidine-5-carbonitrile as colorless solid; MS: [M+H]$^+$=339; m.p. 108–111° C.

EXAMPLE 72

4-(2-Hydroxy-ethoxy)-6-(1,2,4,5-tetrahydro-benzo[d]azepin-3-yl)-2-[2-(tetrahydro-pyran-2-yloxy)-ethyl]-pyrimidine-5-carbonitrile From 6-oxo-4-(1,2,4,5-tetrahydro-benzo[d]azepin-3-yl)-2-[2-(tetrahydro-pyran-2-yloxy)-ethyl]-1,6-dihydropyrimidine-5-carbonitrile, 2-bromoethanol, potassium carbonate, N,N-dimethylformamide, as colorless foam; MS: [M+H]$^+$=439; see example 73.

EXAMPLE 73

1-(2-Hydroxy-ethyl)-6-oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile In analogy to the procedure described in example 3 the 6-oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile (example 67) was treated with 2-bromo-ethanol in N,N-dimethylformamide in the presence of potassium carbonate to yield the 4-(2-hydroxy-ethoxy)-6-(1,2,4,5-tetrahydro-benzo[d]azepin-3-yl)-2-[2-(tetrahydro-pyran-2-yloxy)-ethyl]-pyrimidine-5-carbonitrile as colorless foam; MS: [M+H]$^+$=439; and the 1-(2-hydroxy-ethyl)-6-oxo-4-(1,2,4,5 -tetrahydro-benzo[d]azepin-3-yl)-2-[2-(tetrahydro-pyran-2-yloxy)-ethyl]-1,6-dihydro-pyrimidine-5-carbonitrile as yellow foam; MS: [M+H]$^+$=439.

EXAMPLE 74

1,2-Bis-(2-hydroxy-ethyl)-6-oxo-4-(1,2,4,5-tetrahydro-benzo[d]azepin-3-yl)-1,6-dihydro-pyrimidine-5-carbonitrile In analogy to the procedure described in example 70 the 1-(2-hydroxy-ethyl)-6-oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile (example 73) was treated with HCl in methanol to yield the 1,2-bis-(2-hydroxy-ethyl)-6-oxo-4-(1,2,4,5-tetrahydro-benzo[d]azepin-3-yl)-1,6-dihydro-pyrimidine-5-carbonitrile as colorless solid; MS: [M+H]$^+$=355; m.p. 164° C.

EXAMPLE 75

4-(2-Hydroxy-ethoxy)-2-(2-hydroxy-ethyl)-6-(1,2,4,5-tetrahydro-benzo[d]azepin-3-yl)-pyrimidine-5-carbonitrile In analogy to the procedure described in example 70 the 4-(2-hydroxy-ethoxy)-6-(1,2,4,5-tetrahydro-benzo[d]azepin-3-yl)-2-[2-(tetrahydro-pyran-2-yloxy)-ethyl]-pyrimidine-5-carbonitrile (example 72) was treated with HCl in methanol to yield the 4-(2-hydroxy-ethoxy)-2-(2-hydroxy-ethyl)-6-(1,2,4,5-tetrahydro-benzo[d]azepin-3-yl)-pyrimidine-5-carbonitrile as colorless solid; MS: [M+H]$^+$= 355; m.p. 118–120° C.

EXAMPLE 76

4-(1,2,4,5-Tetrahydro-benzo[d]azepin-3-yl)-pyrimidine-5-carbonitrile

In analogy to the procedure described in example 4 the 4-chloro-pyrimidine-5-carbonitrile (prepared from 4-hydroxy-5-pyrimidine-carbonitrile and phosphorus oxychloride, phosphorus pentachloride and N-ethyl-N,N-diisopropylamine in acetonitril at reflux) was treated with 2,3,4,5-tetrahydro-1H-benzo[d]azepine hydrochloride [J. Heterocycl. Chem. (1971), 8(5), 779–83] in N,N-dimethylformamide in the presence of N-ethyl-N,N-diisopropylamine at room temperature to yield the 4-(1,2,4,5-tetrahydro-benzo[d]azepin-3-yl)-pyrimidine-5-carbonitrile as off white solid; MS: [M+H]$^+$=251; m.p. 148–150° C.

EXAMPLE 77

6-(7-Chloro-1,2,4,5-tetrahydro-benzo[d]azepin-3-yl)-2-methyl-5-nitro-3H-pyrimidin-4-one In analogy to the procedure described in example 4 the 6-bromo-2-methyl-5-nitro-3H-pyrimidin-4-one (prepared from 2-methyl-4-methoxy-5-nitro-6-chloro-pyrimidine [Helv. (1958), 41, 1806] and hydrobromic acid (48% in water) in acetic acid at room temperature) was treated with the 7-chloro-2,3,4,5-tetrahydro-1H-benzo[d]azepine [J. Heterocycl. Chem. (1971), 8(5), 779–83] in N,N-dimethylformamide in the presence of N-ethyl-N,N-diisopropylamine at room temperature to yield the 6-(7-chloro-1,2,4,5-tetrahydro-benzo[d]azepin-3-yl)-2-methyl-5-nitro-3H-pyrimidin-4-one as yellow solid; m.p. 218° C. (decomposition); MS: [M+H]$^+$=335.

EXAMPLE 78

2-Methyl-6-oxo-4-(1,2,4,5-tetrahydro-benzo[d]azepin-3-yl)-1-(2,2,2-trifluoro-ethyl)-1,6-dihydro-pyrimidine-5-carbonitrile From 2-methyl-6-oxo-4-(1,2,4,5-tetrahydro-benzo[d]azepin-3-yl)-1,6-dihydro-pyrimidine-5-carbonitrile, 2,2,2-trifluoroethyl iodide, potassium carbonate, N,N-dimethylformamide, as yellowish solid; m.p. 186–188° C.; MS: [M+H]$^+$=363; see example 79.

EXAMPLE 79

2-Methyl-4-(1,2,4,5-tetrahydro-benzo[d]azepin-3-yl)-6-(2,2,2-trifluoro-ethoxy)-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with 2,2,2-trifluoroethyl iodide in N,N-dimethylformamide in the presence of potassium carbonate at 80° C. to yield the 2-methyl-6-oxo-4-(1,2,4,5-tetrahydro-benzo[d]azepin-3-yl)-1-(2,2,2-trifluoro-ethyl)-1,6-dihydro-pyrimidine-5-carbonitrile as yellowish solid; m.p. 186–188° C.; MS: [M+H]$^+$=363; and the 2-methyl-4-(1,2,4,5-tetrahydro-benzo[d]azepin-3-yl)-6-(2,2,2-trifluoro-ethoxy)-pyrimidine-5-carbonitrile as colorless solid; m.p. 108–110° C.; MS: [M+H]$^+$=363.

EXAMPLE 80

2-(2-Methylsulfanyl-ethyl)-6-oxo-4-(1,2,4,5-tetrahydro-benzo[d]azepin-3-yl)-1,6-dihydro-pyrimidine-5-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with 3-hydroxy-propionamidine hydrochloride (1:1) [Tetrahedron Lett. (1990), 31(14), 1969–72] and 1,8-diazabicyclo[5.4.0]undec-7-en in N,N-dimethylform at 100° C. to yield beside 2-(2-hydroxy-ethyl)-6-oxo-4-(1,2,4,5-tetrahydro-benzo[d]azepin-3-yl)-1,6-dihydro-pyrimidine-5-carbonitrile (example 24) the 2-(2-methylsulfanyl-ethyl)-6-oxo-4-(1,2,4,5-tetrahydro-benzo[d]azepin-3-yl)-1,6-dihydro-pyrimidine-5-carbonitrile as colorless solid; m.p. 215–218° C. (decomposition); MS: [M+H]$^+$=341.

EXAMPLE 81

1-Ethyl-2-(2-methylsulfanyl-ethyl)-6-oxo-4-(1,2,4,5-tetrahydro-benzo[d]azepin-3-yl)-1,6-dihydro-pyrimidine-5-carbonitrile From 2-(2-methylsulfanyl-ethyl)-6-oxo-4-(1,2,4,5-tetrahydro-benzo[d]azepin-3-yl)-1,6-dihydro-pyrimidine-5- carbonitrile, ethyliodide, potassium carbonate, N,N-dimethylformamide, as colorless solid; m.p. 154–159° C.; MS: [M+H]$^+$=369; see example 82.

EXAMPLE 82

4-Ethoxy-2-(2-methylsulfanyl-ethyl)-6-(1,2,4,5-tetrahydro-benzo[d]azepin-3-yl)-pyrimidine-5-carbonitrile In analogy to the procedure described in example 3 the 2-(2-methylsulfanyl-ethyl)-6-oxo-4-(1,2,4,5-tetrahydro-benzo[d]azepin-3-yl)-1,6-dihydro-pyrimidine-5-carbonitrile (example 80) was treated with ethyliodide in N,N-dimethylformamide in the presence of potassium carbonate to yield the 1-ethyl-2-(2-methylsulfanyl-ethyl)-6-oxo-4-(1,2,4,5-tetrahydro-benzo[d]azepin-3-yl)-1,6-dihydro-pyrimidine-5-carbonitrile as colorless solid; m.p. 154–159° C.; MS: [M+H]$^+$=369; and the 4-ethoxy-2-(2-methylsulfanyl-ethyl)-6-(1,2,4,5-tetrahydro-benzo[d]azepin-3-yl)-pyrimidine-5-carbonitrile as colorless solid; m.p. 102–104° C.; MS: [M+H]$^+$=369.

EXAMPLE 83

1-(2-Hydroxy-ethyl)-2-(2-methylsulfanyl-ethyl)-6-oxo-4-(1,2,4,5-tetrahydro-benzo[d]azepin-3-yl)-1,6-dihydro-pyrimidine-5-carbonitrile From 2-(2-methylsulfanyl-ethyl)-6-oxo-4-(1,2,4,5-tetrahydro-benzo[d]azepin-3-yl)-1,6-dihydro-pyrimidine-5-carbonitrile, potassium carbonate, N,N-dimethylformamide, bromoethanol, as yellowish amorphous solid; MS: [M+H]$^+$=385; see example 84.

EXAMPLE 84

4-(2-Hydroxy-ethoxy)-2-(2-methylsulfanyl-ethyl)-6-(1,2,4,5-tetrahydro-benzo[d]azepin-3-yl)-pyrimidine-5-carbonitrile In analogy to the procedure described in example 3 the 2-(2-methylsulfanyl-ethyl)-6-oxo-4-(1,2,4,5-tetrahydro-benzo[d]azepin-3-yl)-1,6-dihydro-pyrimidine-5-carbonitrile (example 80) was treated with 2-bromo-ethanol in N,N-dimethylformamide in the presence of potassium carbonate to yield the 1-(2-hydroxy-ethyl)-2-(2-methylsulfanyl-ethyl)-6-oxo-4-(1,2,4,5-tetrahydro-benzo[d]azepin-3-yl)-1,6-dihydro-pyrimidine-5-carbonitrile as yellowish amorphous solid; MS: [M+H]$^+$=385; and the 4-(2-hydroxy-ethoxy)-2-(2-methylsulfanyl-ethyl)-6-(1,2,4,5-tetrahydro-benzo[d]azepin-3-yl)-pyrimidine-5-carbonitrile as yellowish solid; m.p. 93–99° C.; MS: [M+H]$^+$=385.

EXAMPLE 85

3-(2-Hydroxy-ethyl)-2-methyl-5-nitro-6-(1,2,4,5-tetrahydro-benzo[d]azepin-3-yl)-3H-pyrimidin-4-one From 2-methyl-5-nitro-6-(1,2,4,5-tetrahydro-benzo[d]azepin-3-yl)-pyrimidin-4-ol and 2-bromoethanol, potassium carbonate in N,N- dimethylformamide, as yellow solid; m.p. 151–155° C.; MS: [M+H]$^+$=345; see example 86.

EXAMPLE 86

2-[2-Methyl-5-nitro-6-(1,2,4,5-tetrahydro-benzo[d]azepin-3-yl)-pyrimidin-4-yloxy]-ethanol In analogy to the procedure described in example 3 the 2-methyl-5-nitro-6-(1,2,4,5-tetrahydro-benzo[d]azepin-3-yl)-pyrimidin-4-ol (example 1) was treated with 2-bromo-ethanol in N,N-dimethylformamide in the presence of potassium carbonate to yield the 3-(2-hydroxy-ethyl)-2-methyl-5-nitro-6-(1,2,4,5-tetrahydro-benzo[d]azepin-3-yl)-3H-pyrimidin-4-one as yellow solid; m.p. 151–155° C.; MS: [M+H]$^+$=345; and 2-[2-methyl-5-nitro-6-(1,2,4,5-tetrahydro-benzo[d]azepin-3-yl)-pyrimidin-4-yloxy]-ethanol as light yellow solid; m.p. 113° C. (decomposition); MS: [M+H]$^+$=345.

EXAMPLE 87

3-(5-Methyl-3-nitro-pyridin-2-yl)-2,3,4,5-tetrahydro-1H-benzo[d]azepine

In analogy to the procedure described in example 4 the 2-chloro-5-methyl-3-nitro-pyridine [J. Organomet. Chem. (1996), 517(1–2), 25–36] was treated with 2,3,4,5-tetrahydro-1H-benzo[d]azepine hydrochloride [J. Heterocycl. Chem. (1971), 8(5), 779–83] in N,N-dimethylformamide in the presence of N-ethyl-N,N-diisopropylamine at room temperature to yield the 3-(5-methyl-3-nitro-pyridin-2-yl)-2,3,4,5-tetrahydro-1H-benzo[d]azepine as yellow solid; MS: [M+H]$^+$=284; m.p. 87–88° C.

EXAMPLE 88

2-(2-Methylsulfanyl-ethyl)-4-(1,2,4,5-tetrahydro-benzo[d]azepin-3-yl)-6-(2,2,2-trifluoro-ethoxy)-pyrimidine-5-carbonitrile In analogy to the procedure described in example 3 the 2-(2-methylsulfanyl-ethyl)-6-oxo-4-(1,2,4,5-tetrahydro-benzo[d]azepin-3-yl)-1,6-dihydro-pyrimidine-5-carbonitrile (example 80) was treated with 2,2,2-trifluoroethyl trifluoromethanesulfonate in N,N-dimethylformamide in the presence of potassium carbonate to yield the 2-(2-methylsulfanyl-ethyl)-4-(1,2,4,5-tetrahydro-benzo[d]azepin-3-yl)-6-(2,2,2-trifluoro-ethoxy)-pyrimidine-5-carbonitrile as colorless solid; m.p. 97–100° C.; MS: [M+H]$^+$=423.

EXAMPLE 89

2-Methylsulfanyl-6-oxo-4-(1,2,4,5-tetrahydro-benzo[d]azepin-3-yl)-1,6-dihydro-pyrimidine-5-carbonitrile a) 0.475 g (1.50 mmol) of E and/or Z 2-cyano-3-methylsulfanyl-3-(1,2,4,5-tetrahydro-benzo[d]azepin-3-yl)-acrylic acid ethyl ester [example 13 a)] were dissolved in 8.0 ml of dichloromethane and treated with 0.712 g (3.30 mmol) of m-chloroperbenzoic acid. After stirring at room temperature for 18 hours, the reaction mixture was poured into 30 ml of an ice/dil. aq. sodium carbonate mixture and extracted three times with 20 ml of dichloromethane. The combined organic phases were dried over magnesium sulphate and evaporated under reduced pressure. The thus obtained crude product was purified by chromatography on silica gel using a 1:1 v/v mixture of ethylacetate and hexane as eluent to yield after crystallization from ether 0.115 g (0.330 mmol), 22%, of E and/or Z 2-cyano-3-methanesulfonyl-3-(1,2,4,5-tetrahydro-benzo[d]azepin-3-yl)-acrylic acid ethyl ester as yellowish solid; MS: [M+H]$^+$=349; m.p. 80° C.

b) 0.100 g (0.287 mmol) of E and/or Z 2-cyano-3-methanesulfonyl-3-(1,2,4,5-tetrahydro-benzo[d]azepin-3-yl)-acrylic acid ethyl ester, 0.082 mg (0.287 mmol) S-methylisothiourea-sulfate and 0.107 mg (1.03 mmol) triethylamine were dissolved in 2.0 ml of ethanol and heated under reflux for 6 hours. After cooling to room temperature the reaction mixture was evaporated to dryness, poured into 1N HCl solution and extracted three times with 20 ml of dichloromethane. The combined organic phases were dried over magnesium sulphate and evaporated under reduced pressure. The thus obtained crude product was purified by chromatography on silica gel using a 95:5 v/v mixture of dichloromethane and methanol as eluent to yield after crystallization from ethyl acetate 0.012 g (0.039 mmol), 14%, of 2-methylsulfanyl-6-oxo-4-(1,2,4,5-tetrahydro-benzo[d]azepin-3-yl)-1,6-dihydro-pyrimidine-5-carbonitrile as colorless solid; MS: [M+H]$^+$=313; m.p. >250° C.

EXAMPLE 90

6-(7-Methoxy-1,2,4,5-tetrahydro-benzo[d]azepin-3-yl)-2-methyl-5-nitro-3H-pyrimidin-4-one In analogy to the procedure described in example 4 the 6-bromo-2-methyl-5-nitro-3H-pyrimidin-4-one (prepared from 2-methyl-4-methoxy-5-nitro-6-chloro-pyrimidine [Helv. (1958), 41, 1806] and hydrobromic acid (48% in water) in acetic acid at room temperature) was treated with the 7-methoxy-2,3,4,5-tetrahydro-1H-benzo[d]azepine [J. Heterocycl. Chem. (1971), 8(5), 779–83] in N,N-dimethylformamide in the presence of N-ethyl-N,N-diisopropylamine at room temperature to yield the 6-(7-methoxy-1,2,4,5-tetrahydro-benzo[d]azepin-3-yl)-2-methyl-5-nitro-3H-pyrimidin-4-one as yellow solid; m.p. 243° C. (decomposition); MS: [M+H]$^+$=331.

EXAMPLE 91

Dimethyl-{2-[2-methyl-5-nitro-6-(1,2,4,5-tetrahydro-benzo[d]azepin-3-yl)-pyrimidin-4-yloxy]-ethyl}-amine From 2-methyl-5-nitro-6-(1,2,4,5-tetrahydro-benzo[d]azepin-3-yl)-pyrimidin-4-ol with 1-chloro-2-dimethylamino-ethane hydrochloride, potassium carbonate, N,N-dimethylformamide, as yellow oil; MS: [M+H]$^+$=372; see example 92.

EXAMPLE 92

3-(2-Dimethylamino-ethyl)-2-methyl-5-nitro-6-(1,2,4,5-tetrahydro-benzo[d]azepin-3-yl)-3H-pyrimidin-4-one In analogy to the procedure described in example 3 the 2-methyl-5-nitro-6-(1,2,4,5-tetrahydro-benzo[d]azepin-3-yl)-pyrimidin-4-ol (example 1) was treated with 1-chloro-2-dimethylamino-ethane hydrochloride in N,N-dimethylformamide in the presence of potassium carbonate at 50° C. to yield the dimethyl-{2-[2-methyl-5-nitro-6-(1,2,4,5-tetrahydro-benzo[d]azepin-3-yl)-pyrimidin-4-yloxy-ethyl}-amine as yellow oil; MS: [M+H]$^+$=372; and the 3-(2-dimethylamino-ethyl)-2-methyl-5-nitro-6-(1,2,4,5-tetrahydro-benzo[d]azepin-3-yl)-3H-pyrimidin-4-one as yellow amorphous solid; MS: [M+H]$^+$=372.

EXAMPLE 93

3-[2-Methyl-6-(2-morpholin-4-yl-ethoxy)-5-nitro-pyrimidin-4-yl]-2,3,4,5-tetrahydro-1H-benzo[d]azepine From 2-methyl-5-nitro-6-(1,2,4,5-tetrahydro-benzo[d]azepin-3-yl)-pyrimidin-4-ol with 4-(2-chloroethyl)-morpholine hydrochloride, potassium carbonate, N,N-dimethylformamide, as yellow oil; MS: [M+H]$^+$=414; see example 94.

EXAMPLE 94

2-Methyl-3-(2-morpholin-4-yl-ethyl)-5-nitro-6-(1,2,4,5-tetrahydro-benzo[d]azepin-3-yl)-3H-pyrimidin-4-one In analogy to the procedure described in example 3 the 2-methyl-5-nitro-6-(1,2,4,5-tetrahydro-benzo[d]azepin-3-yl)-pyrimidin-4-ol (example 1) was treated with 4-(2-chloroethyl)-morpholine hydrochloride in N,N-dimethylformamide in the presence of potassium carbonate at 50° C. to yield the 3-[2-methyl-6-(2-morpholin-4-yl-ethoxy)-5-nitro-pyrimidin-4-yl]-2,3,4,5-tetrahydro-1H-benzo[d]azepine as yellow oil; MS: [M+H]$^+$=414; and the 2-methyl-3-(2-morpholin-4-yl-ethyl)-5-nitro-6-(1,2,4,5-tetrahydro-benzo[d]azepin-3-yl-3H-pyrimidin-4-one as yellow solid; m.p. 143–145° C.; MS: [M+H]$^+$=414.

EXAMPLE 95

4-(1,2,4,5-Tetrahydro-benzo[d]azepin-3-yl)-2-[2-(tetrahydro-pyran-2-yloxy)-ethyl]-6-(2,2,2-trifluoro-ethoxy)-pyrimidine-5-carbonitrile In analogy to the procedure described in example 3 the 6-oxo-4-(1,2,4,5-tetrahydro-benzo[d]azepin-3-yl)-2-[2-(tetrahydro-pyran-2-yloxy)-ethyl]-1,6-dihydro-pyrimidine-5-carbonitrile (example 67) was treated with 2,2,2-trifluoroethyl trifluoromethanesulfonate in N,N-dimethylformamide in the presence of potassium carbonate to yield the 4-(1,2,4,5 -tetrahydro-benzo[d]azepin-3-yl)-2-[2-(tetrahydro-pyran-2-yloxy)-ethyl]-6-(2,2,2-trifluoro-ethoxy)-pyrimidine-5-carbonitrile as yellow oil; MS: [M+H]$^+$=477.

EXAMPLE 96

2-(2-Hydroxy-ethyl)-4-(1,2,4,5-tetrahydro-benzo[d]azepin-3-yl)-6-(2,2,2-trifluoro-ethoxy)-pyrimidine-5-carbonitrile In analogy to the procedure described in example 70 the 4-(1,2,4,5-tetrahydro-benzo[d]azepin-3-yl)-2-[2-(tetrahydro-pyran-2-yloxy)-ethyl]-6-(2,2,2-trifluoro-ethoxy)-pyrimidine-5-carbonitrile (example 95) was treated with 1.5N HCl in methanol to yield the 2-(2-hydroxy-ethyl)-4-(1,2,4,5-tetrahydro-benzo[d]azepin-3-yl)-6-(2,2,2-trifluoro-ethoxy)-pyrimidine-5-carbonitrile as colorless solid; MS: [M+H]$^+$=393; m.p. 114–116° C.

EXAMPLE 97

2-Hydroxymethyl-6-oxo-4-(1,2,4,5-tetrahydro-benzo[d]azepin-3-yl)-1,6-dihydro-pyrimidine-5-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with glycolamidine hydrochloride [J. Amer. Chem. Soc. 68, 2393–2395 (1946)] and 1,8-diazabicyclo [5.4.0]undec-7-en in N,N-dimethylformamide at 110° C. to yield the 2-hydroxymethyl-6-oxo-4-(1,2,4,5-tetrahydro-benzo[d]azepin-3-yl)-1,6-dihydro-pyrimidine-5-carbonitrile as colorless solid; m.p. 196–198° C.; MS: [M]$^+$=296.

EXAMPLE 98

2,3-Diethyl-5-nitro-6-(1,2,4,5-tetrahydro-benzo[d]azepin-3-yl)-3H-pyrimidin-4-one From 3-ethyl-2-methyl-5-nitro-6-(1,2,4,5-tetrahydro-benzo[d]azepin-3-yl)-3H-pyrimidin-4-one and methyl iodide, lithium-bis-(trimethylsilyl) amide in tetrahydrofuran, as yellow oil; MS: [M+H]$^+$=343; see example 99.

EXAMPLE 99

3-Ethyl-2-isopropyl-5-nitro-6-(1,2,4,5-tetrahydro-benzo[d]azepin-3-yl)-3H-pyrimidin-4-one 0.328 g (1.0 mmol) of 3-ethyl-2-methyl-5-nitro-6-(1,2,4,5-tetrahydro-benzo[d]azepin-3-yl)-3H-pyrimidin-4-one (example 2) were dissolved in 10.0 ml of tetrahydrofuran, the solution cooled in an argon atmosphere to −70° C. and treated with 1.2 ml of an 1.0M solution of lithium-bis-(trimethylsilyl)amide in tetrahydrofuran, stirred at −70° C. for 120 minutes and treated with 0.095 ml (1.5 mmol) of methyliodide. The reaction mixture was then allowed to come to room temperature and stirring continued overnight, subsequently poured into 50 ml of an ice/water mixture and extracted three times with 100 ml of ethylacetate. The combined organic phases were washed twice with 50 ml of water, dried over magnesium sulphate, evaporated under reduced pressure and dried in a high vacuum. The thus obtained crude product was purified by chromatography on silica gel using a 9:1 to 1:1 v/v mixture of hexane and ethyl acetate as eluent to yield 0.055 g (0.161 mmol), 16.1%, of 2,3-diethyl-5-nitro-6-(1,2,4,5-tetrahydro-benzo[d]azepin-3-yl)-3H-pyrimidin-4-one as yellow oil; MS: [M+H]$^+$=343; and 0.012 g (0.034 mmol), 3.4%, of 3-ethyl-2-isopropyl-5-nitro-6-(1,2,4,5-tetrahydro-benzo[d]azepin-3-yl)-3H-pyrimidin-4-one as yellow oil; MS: [M+H]$^+$=357.

EXAMPLE 100

3-(4-Butyl-5-methyl-3-nitro-pyridin-2-yl)-2,3,4,5-tetrahydro-1H-benzo[d]azepine 0.283 g (1.0 mmol) of 3-(5-methyl-3-nitro-pyridin-2-yl)-2,3,4,5-tetrahydro-1H-benzo[d]azepine (example 87) were dissolved in 10.0 ml of tetrahydrofuran, the solution cooled in an argon atmosphere to −70° C. and treated with 0.94 ml of an 1.6M solution of n-butyllithium in n-hexane, stirred at −70° C. for 120 minutes, then allowed to come to room temperature and stirring continued overnight. Subsequently it was poured into 50 ml of an ice/water mixture and extracted three times with 100 ml of ethylacetate. The combined organic phases were washed twice with 50 ml of water, dried over magnesium sulphate, evaporated under reduced pressure and dried in a high vacuum. The thus obtained crude product was purified by chromatography on silica gel using a 98:2 to 9:1 v/v mixture of hexane and ethyl acetate as eluent to yield 0.071 g (0.21 mmol), 21%, of 3-(4-butyl-5-methyl-3-nitro-pyridin-2-yl)-2,3,4,5-tetrahydro-1H-benzo[d]azepine as yellow oil; MS: [M+H]$^+$=340.

EXAMPLE 101

6-(6-Methoxy-1,2,4,5-tetrahydro-benzo[d]azepin-3-yl)-2-methyl-5-nitro-3H-pyrimidin-4-one In analogy to the procedure described in example 4 the 6-bromo-2-methyl-5-nitro-3H-pyrimidin-4-one (see example 66) was treated with the 6-methoxy-2,3,4,5-tetrahydro-1H-benzo[d]azepine [J. Med. Chem. (1984),27 (7), 918–21] in N,N-dimethylformamide in the presence of N-ethyl-N,N-diisopropylamine at room temperature to yield the 6-(6-methoxy- 1,2,4,5-tetrahydro-benzo[d]azepin-3-yl)-2-methyl-5-nitro-3H-pyrimidin-4-one as yellow solid; m.p. >200° C.; MS: [M+H]$^+$=331.

EXAMPLE 102

2-[2-Methyl-5-nitro-6-(1,2,4,5-tetrahydro-benzo[d]azepin-3-yl)-pyrimidin-4-yloxy]-ethylamine a) 0.300 g (1.00 mmol) of the 2-methyl-5-nitro-6-(1,2,4,5-tetrahydro-benzo[d]azepin-3-yl)-pyrimidin-4-ol (example 1), 0.194 g (1.20 mmol) of N-tert-butoxycarbonyl-aminoethanol and 0.371 g (1.40 mmol) of triphenylphosphin were dissolved in 15.0 ml of tetrahydroftiran, the solution cooled to 2° C. and treated with 0.306 g (1.30 mmol) of di-tert-butyl azodicarboxylate. The reaction mixture was then allowed to come to room temperature and stirring continued for 22 hours. Subsequently it was poured into 50 ml of an ice/water mixture and extracted three times with 100 ml of ethylacetate. The combined organic phases were washed twice with 50 ml of water, dried over magnesium sulphate, evaporated under reduced pressure and dried in a high vacuum. The thus obtained crude product was purified by chromatography on silica gel using a 95:5 to 4:1 v/v mixture of hexane and ethyl acetate as eluent to yield impure {2-[2-methyl-5-nitro-6-(1,2,4,5-tetrahydro-benzo[d]azepin-3-yl)-pyrimidin-4-yloxy]-ethyl}-carbamic acid tert-butyl ester as yellow solid; MS: [M+H]$^+$=444.

b) The impure {2-[2-methyl-5-nitro-6-(1,2,4,5-tetrahydro-benzo[d]azepin-3-yl)-pyrimidin-4-yloxy]-ethyl}-carbamic acid tert-butyl ester prepared in a) was dissolved in 10.0 ml of methanol and treated with 5.96 ml of an 1.56M solution of hydrogen chloride in methanol and the reaction mixture stirred at room temperature for 72 hours. Subsequently it was poured into 50 ml of an ice/water mixture, neutralized with sodium hydrogen carbonate solution and extracted three times with 100 ml of diochloromethane. The combined organic phases were washed twice with 50 ml of water, dried over magnesium sulphate, evaporated under reduced pressure and dried in a high vacuum. The thus obtained crude product was purified by chromatography on silica gel using a 9:1 to 0:1 v/v mixture of hexane and ethyl acetate as eluent to yield 0.058 g (0.169 mmol), 16.9% over two steps, of the 2-[2-methyl-5-nitro-6-(1,2,4,5-tetrahydro-benzo[d]azepin-3-yl)-pyrimidin-4-yloxy]-ethylamine as light yellow oil; MS: [M+H]$^+$=344.

EXAMPLE 103

4-(Bromo-difluoro-methoxy)-6-(1,2,4,5-tetrahydro-benzo[d]azepin-3-yl)-pyrimidine-5-carbonitrile In analogy to the procedure described in example 60 the 6-oxo-4-(1,2,4,5-tetrahydro-benzo[d]azepin-3-yl)-1,6-dihydro-pyrimidine-5-carbonitrile (example 15) was treated with dibromo-difluoro-methane in N,N-dimethylformamide in the presence of sodium hydride at room temperature to yield the 4-(bromo-difluoro-methoxy)-6-(1,2,4,5-tetrahydro-benzo[d]azepin-3-yl)-pyrimidine-5-carbonitrile as colorless solid; m.p. 95–100° C.; MS: [M+H]$^+$=396.

EXAMPLE 104

6-Oxo-4-(1,2,4,5-tetrahydro-benzo[d]azepin-3-yl)-2-(tetrahydro-pyran-2-yloxymethyl)-1,6-dihydro-pyrimidine-5-carbonitrile In analogy to the procedure described in example 67 the 2-hydroxymethyl-6-oxo-4-(1,2,4,5-tetrahydro-benzo[d]azepin-3-yl)-1,6-dihydro-pyrimidine-5-carbonitrile (example 97) was treated with 3,4-dihydro-2H-pyran and pyridinium-(toluene-4-sulfonate) in dichloromethane at room temperature to yield the 6-oxo-4-(1,2,4,5-tetrahydrobenzo[d]azepin-3-yl)-2-(tetrahydro-pyran-2-yloxymethyl)-1,6-dihydro-pyrimidine-5-carbonitrile as colorless solid; m.p. 179.5–183° C.; MS: [M+H]$^+$=381.

EXAMPLE 105

4-(1,2,4,5-Tetrahydro-benzo[d]azepin-3-yl)-2-(tetrahydro-pyran-2-yloxymethyl)-6-(2,2,2-trifluoro-ethoxy)-pyrimidine-5-carbonitrile From the 6-oxo-4-(1,2,4,5-tetrahydro-benzo[d]azepin-3-yl)-2-(tetrahydro-pyran-2-yloxymethyl)-1,6-dihydro-pyrimidine-5-carbonitrile (example 104) and 2,2,2-trifluoroethyl trifluoromethanesulfonate in N,N-dimethylformamide in the presence of potassium carbonate as colorless amorphous solid; MS: [M+H]$^+$=463; see example 106.

EXAMPLE 106

6-Oxo-4-(1,2,4,5-tetrahydro-benzo[d]azepin-3-yl)-2-(tetrahydro-pyran-2-yloxymethyl)-1-(2,2,2-trifluoro-ethyl)-1,6-dihydro-pyrimidine-5-carbonitrile In analogy to the procedure described in example 3 the 6-oxo-4-(1,2,4,5-tetrahydro-benzo[d]azepin-3-yl)-2-(tetrahydro-pyran-2-yloxymethyl)-1,6-dihydro-pyrimidine-5-carbonitrile (example 104) was treated with 2,2,2-trifluoroethyl trifluoromethanesulfonate in N,N-dimethylformamide in the presence of potassium carbonate to yield the 4-(1,2,4,5-tetrahydro-benzo[d]azepin-3-yl)-2-(tetrahydro-pyran-2-yloxymethyl)-6-(2,2,2-trifluoro-ethoxy)-pyrimidine-5-carbonitrile as colorless amorphous solid; MS: [M+H]$^+$=463; and the 6-oxo-4-(1,2,4,5-tetrahydro-benzo[d]azepin-3-yl)-2-(tetrahydro-pyran-2-yloxymethyl)-1-(2,2,2-trifluoro-ethyl)-1,6-dihydro-pyrimidine-5-carbonitrile as colorless amorphous solid; MS: [M+H]$^+$=463.

EXAMPLE 107

2-Hydroxymethyl-4-(1,2,4,5-tetrahydro-benzo[d]azepin-3-yl)-6-(2,2,2-trifluoro-ethoxy)-pyrimidine-5-carbonitrile In analogy to the procedure described in example 70 the 4-(1,2,4,5-tetrahydro-benzo[d]azepin-3-yl)-2-(tetrahydro-pyran-2-yloxymethyl)-6-(2,2,2-trifluoro-ethoxy)-pyrimidine-5-carbonitrile (example 105) was treated with hydrogen chloride in methanol at room temperature to yield the 2-hydroxymethyl-4-(1,2,4,5-tetrahydro-benzo[d]azepin-3-yl)-6-(2,2,2-trifluoro-ethoxy)-pyrimidine-5-carbonitrile as colorless solid; m.p. 106–110° C.; MS: [M]$^+$=378.

EXAMPLE 108

2-Hydroxymethyl-6-oxo-4-(1,2,4,5-tetrahydro-benzo[d]azepin-3-yl)-1-(2,2,2-trifluoro-ethyl)-1,6-dihydro-pyrimidine-5-carbonitrile In analogy to the procedure described in example 70 the 6-oxo-4-(1,2,4,5-tetrahydro-benzo[d]azepin-3-yl)-2-(tetrahydro-pyran-2-yloxymethyl)-1-(2,2,2-trifluoro-ethyl)-1,6-dihydro-pyrimidine-5-carbonitrile (example 106) was treated with hydrogen chloride in methanol at room temperature to yield the 2-hydroxymethyl-6-oxo-4-(1,2,4,5-tetrahydro-benzo[d]azepin-3-yl)-1-(2,2,2-trifluoro-ethyl)-1,6-dihydro-pyrimidine-5-carbonitrile as colorless solid; m.p. 181–185° C.; MS: [M]$^+$=378.

EXAMPLE 109

1-Allyl-2-amino-6-oxo-4-(1,2,4,5-tetrahydro-benzo[d]azepin-3-yl)-1,6-dihydro-pyrimidine-5-carbonitrile From the 2-amino-6-oxo-4-(1,2,4,5-tetrahydro-benzo[d]azepin-3-yl)-1,6-dihydro-pyrimidine-5-carbonitrile (example 13) with allylbromide in N,N-dimethylformamide in the presence of potassium carbonate at room temperature as colorless solid; m.p. >200° C.; MS: [M]$^+$=321; see example 111.

EXAMPLE 110

1-Allyl-2-allylamino-6-oxo-4-(1,2,4,5-tetrahydro-benzo[d]azepin-3-yl)-1,6-dihydro-pyrimidine-5-carbonitrile From the 2-amino-6-oxo-4-(1,2,4,5-tetrahydro-benzo[d]azepin-3-yl)-1,6-dihydro-pyrimidine-5-carbonitrile (example 13) with allylbromide in N,N-dimethylformamide in the presence of potassium carbonate at room temperature as colorless solid; m.p. 181–182.5° C.; MS: [M]$^+$=361; see example 111.

EXAMPLE 111

4-Allyloxy-2-amino-6-(1,2,4,5-tetrahydro-benzo[d]azepin-3-yl)-pyrimidine-5-carbonitrile In analogy to the procedure described in example 3 the 2-amino-6-oxo-4-(1,2,4,5-tetrahydro-benzo[d]azepin-3-yl)-1,6-dihydro-pyrimidine-5-carbonitrile (example 13) was treated with allylbromide in N,N-dimethylformamide in the presence of potassium carbonate at room temperature to yield the 1-allyl-2-amino-6-oxo-4-(1,2,4,5-tetrahydro-benzo[d]azepin-3-yl)-1,6-dihydro-pyrimidine-5-carbonitrile as colorless solid; m.p. >200° C.; MS: [M]$^+$=321; the 1-allyl-2-allylamino-6-oxo-4-(1,2,4,5-tetrahydro-benzo[d]azepin-3-yl)-1,6-dihydro-pyrimidine-5-carbonitrile as colorless solid; m.p. 181–182.5° C.; MS: [M]$^+$=361; and the 4-allyloxy-2-amino-6-(1,2,4,5-tetrahydro-benzo[d]azepin-3-yl)-pyrimidine-5-carbonitrile as colorless amorphous solid; MS: [M+H]$^+$=322.

EXAMPLE 112

1-Allyl-2-ethylamino-6-oxo-4-(1,2,4,5-tetrahydro-benzo[d]azepin-3-yl)-1,6-dihydro-pyrimidine-5-carbonitrile In analogy to the procedure described in example 3 the 1-allyl-2-amino-6-oxo-4-(1,2,4,5-tetrahydro-benzo[d]azepin-3-yl)-1,6-dihydro-pyrimidine-5-carbonitrile (example 109) was treated with ethyliodide in N,N-dimethylformamide in the presence of potassium carbonate at room temperature to yield the 1-allyl-2-ethylamino-6-oxo-4-(1,2,4,5-tetrahydro-benzo[d]azepin-3-yl)-1,6-dihydro-pyrimidine-5-carbonitrile as colorless solid; m.p. 172–177° C.; MS: [M+H]$^+$=350.

EXAMPLE 113

1-Allyl-2-(allyl-ethyl-amino)-6-oxo-4-(1,2,4,5-tetrahydro-benzo[d]azepin-3-yl)-1,6-dihydro-pyrimidine-5-carbonitrile In analogy to the procedure described in example 3 the 1-allyl-2-allylamino-6-oxo-4-(1,2,4,5-tetrahydro-benzo[d]azepin-3-yl)-1,6-dihydro-pyrimidine-5-carbonitrile (example 110) was treated with ethylbromide in N,N-dimethylformamide in the presence of potassium carbonate at room temperature to yield the 1-allyl-2-(allyl-ethyl-amino)-6-oxo-4-(1,2,4,5-tetrahydro-benzo[d]azepin-3-yl)-1,6-dihydro-pyrimidine-5-carbonitrile as colorless solid; m.p. 138.5–140.5° C.; MS: [M+H]$^+$=390.

EXAMPLE 114

1-Cyclopropyl-2-methyl-6-oxo-4-(1,2,4,5-tetrahydro-benzo[d]azepin-3-yl)-1,6-dihydro-pyrimidine-5-carbonitrile In analogy to the procedure described in example 17 the Z and/or E 2-cyano-3-methylsulfanyl-3-(1,2,4,5-tetrahydrobenzo[d]azepin-3-yl)-acrylic acid ethyl ester [example 13 a)] was treated with N-1-cyclopropyl acetamidine hydrochloride (from ethyl acetimidate hydrochloride and cyclopropylamine in ethanol at reflux, used as crude reaction product) and 1,8-diazabicyclo[5.4.0]undec-7-en in N,N-dimethylformamide at 100° C. to yield the 1-cyclopropyl-2-methyl-6-oxo-4-(1,2,4,5-tetrahydro-benzo[d]azepin-3-yl)-1,6-dihydro-pyrimidine-5-carbonitrile as light yellow solid; m.p. 177–179° C.; MS: [M+H]$^+$=321.

EXAMPLE 115

5-Ethyl-6-methyl-2-(1,2,4,5-tetrahydro-benzo[d] azepin-3-yl)-nicotinonitrile

In analogy to the procedure described in example 1 the 2-choro-5-ethyl-6-methyl-nicotinonitrile [J. Med. Chem. (1992), 35(21), 3784–91] was treated with the 2,3,4,5-tetrahydro-1H-benzo[d]azepine hydrochloride [J. Heterocyd. Chem. (1971), 8(5), 779–83] in the presence of potassium carbonate in N,N-dimethylformamide at 120° C. to yield the 5-ethyl-6-methyl-2-(1,2,4,5-tetrahydro-benzo[d] azepin-3-yl)-nicotinonitrile as a light yellow oil; MS: [M+H]$^+$=292.

EXAMPLE 116

5-Oxo-7-(1,2,4,5-tetrahydro-benzo[d]azepin-3-yl)-1, 2,3,5-tetrahydro-imidazo[1,2-a]pyrimidine-6-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with 2-iminoimidazolidine hydrobromide and 1,8-diazabicyclo[5.4.0]undec-7-en in N,N-dimethylformamide at 100° C. to yield the 5-oxo-7-(1,2,4, 5-tetrahydro-benzo[d]azepin-3-yl)-1,2,3,5-tetrahydro-imidazo[1,2-a]pyrimidine-6-carbonitrile as colorless solid; m.p. >200° C.; MS: [M+H]$^+$=308.

EXAMPLE 117

5-Oxo-7-(1,2,4,5-tetrahydro-benzo[d]azepin-3-yl)-1, 5-dihydro-imidazo[1,2-a]pyrimidine-6-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with 2-aminoimidazole sulfate and 1,8-diazabicyclo 5.4.0]undec-7-en in N,N-dimethylformamide at 100° C. to yield the 5-oxo-7-(1,2,4,5-tetrahydro-benzo[d] azepin-3-yl)-1,5-dihydro-imidazo[1,2-a]pyrimidine-6-carbonitrile as brownish solid; m.p. >200° C.; MS: [M+H]$^+$= 306.

EXAMPLE 118

1-Methyl-5-oxo-7-(1,2,4,5-tetrahydro-benzo[d] azepin-3-yl)-1,2,3,5-tetrahydro-imidazo[1,2-a] pyrimidine-6-carbonitrile In analogy to the procedure described in example 3 the 5-oxo-7-(1,2,4,5-tetrahydro-benzo[d]azepin-3-yl)-1,2,3,5-tetrahydro-imidazo[1,2-a]pyrimidine-6-carbonitrile (example 116) was treated with dimethylsulfate in N,N-dimethylformamide in the presence of potassium carbonate at room temperature to yield the 1-methyl-5-oxo-7-(1,2,4, 5-tetrahydro-benzo[d]azepin-3-yl)-1,2,3,5-tetrahydro-imidazo[1,2-a]pyrimidine-6-carbonitrile as colorless solid; m.p. 174–177° C.; MS: [M+H]$^+$=322.

EXAMPLE 119

3-[2-Methyl-5-nitro-6-(2,2,2-trifluoro-ethoxy)-pyrimidin-4-yl]-2,3,4,5-tetrahydro-1H-benzo[d] azepine In analogy to the procedure described in example 3 the 2-methyl-5-nitro-6-(1,2,4,5-tetrahydro-benzo[d]azepin-3-yl)-pyrimidin-4-ol (example 1) was treated with 2,2,2-trifluoroethyl iodide in N,N-dimethylformamide in the presence of potassium carbonate at 80° C. to yield beside the 2-methyl-5-nitro-6-(1,2,4,5-tetrahydro-benzo[d]azepin-3-yl)-3-(2,2,2-trifluoro-ethyl)-3H-pyrimidin-4-one (example 11) the 3-[2-methyl-5-nitro-6-(2,2,2-trifluoro-ethoxy)-pyrimidin-4-yl]-2,3,4,5-tetrahydro-1H-benzo[d]azepine as light yellow oil; MS: [M+H]$^+$=383.

EXAMPLE 120

1-Allyl-6-oxo-4-(1,2,4,5-tetrahydro-benzo[d]azepin-3-yl)-2-(2,2,2-trifluoro-ethylamino)-1,6-dihydro-pyrimidine-5-carbonitrile In analogy to the procedure described in example 3 the 1-allyl-2-amino-6-oxo-4-(1,2,4,5-tetrahydro-benzo[d] azepin-3-yl)-1,6-dihydro-pyrimidine-5-carbonitrile (example 109) was treated with 2,2,2-trifluoroethyl-trifluoromethanesulfonate in N,N-dimethylformamide in the presence of potassium carbonate at room temperature to yield the 1-allyl-6-oxo-4-(1,2,4,5-tetrahydro-benzo[d] azepin-3-yl)-2-(2,2,2-trifluoro-ethylamino)-1,6-dihydro-pyrimidine-5-carbonitrile as colorless solid; m.p. 186–191° C.; MS: [M+H]$^+$=404.

EXAMPLE 121

6-Oxo-4-(1,2,4,5-tetrahydro-benzo[d]azepin-3-yl)-1-(2,2,2-trifluoro-ethyl)-2-(2,2,2-trifluoro-ethylamino)-1,6-dihydro-pyrimidine-5-carbonitrile From the 2-amino-6-oxo-4-(1,2,4,5-tetrahydro-benzo[d] azepin-3-yl)-1,6-dihydro-pyrimidine-5-carbonitrile (example 13) with 2,2,2-trifluoroethyl-trifluoromethanesulfonate in N,N-dimethylformamide in the presence of potassium carbonate at room temperature as colorless solid; m.p. >200° C.; MS: [M]$^+$=446; see example 122.

EXAMPLE 122

2-Amino-4-(1,2,4,5-tetrahydro-benzo[d]azepin-3-yl)-6-(2,2,2-trifluoro-ethoxy)-pyrimidine-5-carbonitrile In analogy to the procedure described in example 3 the 2-amino-6-oxo-4-(1,2,4,5-tetrahydro-benzo[d]azepin-3-yl)-1,6-dihydro-pyrimidine-5-carbonitrile (example 13) was treated with 2,2,2-trifluoroethyl-trifluoromethanesulfonate in N,N-dimethylformamide in the presence of potassium carbonate at room temperature to yield the 2-amino-4-(1,2, 4,5-tetrahydro-benzo[d]azepin-3-yl)-6-(2,2,2-trifluoro-ethoxy)-pyrimidine-5-carbonitrile as colorless solid; m.p. 145.3–146.9° C.; MS: [M+H]$^{30}$ =364; and the 6-oxo-4-(1, 2,4,5-tetrahydro-benzo[d]azepin-3-yl)-1-(2,2,2-trifluoro-ethyl)-2-(2,2,2-trifluoro-ethylamino)-1,6-dihydro-pyrimidine-5-carbonitrile as colorless solid; m.p. >200° C.; MS: [M+H]$^+$=446.

EXAMPLE 123

6-(7-Fluoro-1,2,4,5-tetrahydro-benzo[d]azepin-3-yl)-2-methyl-5-nitro-3H-pyrimidin-4-one In analogy to the procedure described in example 4 the 6-bromo-2-methyl-5-nitro-3H-pyrimidin-4-one (see example 66) was treated with the 7-fluoro-2,3,4,5-tetrahydro-1H-benzo[d]azepine in N,N-dimethylformamide in the presence of N-ethyl-N,N-diisopropylamine at room temperature to yield the 6-(7-fluoro-1,2,4,5-tetrahydro-benzo[d]azepin-3-yl)-2-methyl-5-nitro-3H-pyrimidin-4-one as light yellow solid; m.p. >200° C.; MS: [M+H]$^+$=319.

Preparation of the 7-fluoro-2,3,4,5-tetrahydro-1H-benzo[d]azepine

The 7-fluoro-2,3,4,5-tetrahydro-1H-benzo[d]azepine used above was prepared by the following reaction sequence: i) catalytic reduction of the 1-(7-nitro-1,2,4,5-tetrahydro-benzo[d]azepin-3-yl)-ethanone [J. Heterocycl. Chem. (1971), 8(5), 779–83] with hydrogen in methanol in the presence of palladium on charcoal to yield the 1-(7-amino-1,2,4,5-tetrahydro-benzo[d]azepin-3-yl)-ethanone; ii) treatment of the 1-(7-amino-1,2,4,5-tetrahydro-benzo[d]azepin-3-yl)-ethanone with nitrosonium tetrafluoroborate in dichloromethane and decomposition of the thus formed diazonium tetrafluoroborate in boiling 1,2-dichlorobenzene at 180° C. to give the 1-(7-fluoro-1,2,4,5-tetrahydro-benzo[d]azepin-3-yl)-ethanone; iii) conversion of the 1-(7-fluoro-1,2,4,5-tetrahydro-benzo[d]azepin-3-yl)-ethanone into the 7-fluoro- 2,3,4,5-tetrahydro-1H-benzo[d]azepine by removal of the acetyl function with hydrogen chloride (37% in water) in methanol at reflux.

EXAMPLE 124

1-(2-Hydroxy-ethyl)-2-methyl-6-oxo-4-(1,2,4,5-tetrahydro-benzo[d]azepin-3-yl)-1,6-dihydro-pyrimidine-5-carbonitrile From the 2-methyl-6-oxo-4-(1,2,4,5-tetrahydro-benzo[d]azepin-3-yl)-1,6-dihydro-pyrimidine-5-carbonitrile (example 17) with 2-bromoethanol in acetonitrile in the presence of potassium carbonate at reflux as colorless solid; m.p. 164–167.5° C.; MS: [M]$^+$=325; see example 125.

EXAMPLE 125

4-(2-Hydroxy-ethoxy)-2-methyl-6-(1,2,4,5-tetrahydro-benzo[d]azepin-3-yl)-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with 2-bromoethanol in acetonitrile in the presence of potassium carbonate at reflux to yield the 4-(2-hydroxy-ethoxy)-2-methyl-6-(1,2,4,5-tetrahydro-benzo[d]azepin-3-yl)-pyrimidine-5-carbonitrile as yellow solid; m.p. 86.7–92.3° C.; MS: [M]$^+$=325; and the 1-(2-hydroxy-ethyl)-2-methyl-6-oxo-4-(1,2,4,5-tetrahydro-benzo[d]azepin-3-yl)-1,6-dihydro-pyrimidine-5-carbonitrile as colorless solid; m.p. 164–167.5° C.; MS: [M]$^+$=325.

EXAMPLE 126

4-Oxo-2-(1,2,4,5-tetrahydro-benzo[d]azepin-3-yl)-4,6,7,8-tetrahydro-pyrrolo[1,2-a]pyrimidine-3-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with 2-iminopyrrolidine hydrochloride [J. Med. Chem. (1996), 39, 669–672] and 1,8-diazabicyclo[5.4.0]undec-7-en in N,N-dimethylformamide at 100° C. to yield the 4-oxo-2-(1,2,4,5-tetrahydro-benzo[d]azepin-3-yl)-4,6,7,8-tetrahydro-pyrrolo [1,2-a]pyrimidine-3-carbonitrile as colorless solid; m.p. 184.5–190.5° C.; MS: [M+H]$^+$=307.

EXAMPLE 127

4-Oxo-2-(1,2,4,5-tetrahydro-benzo[d]azepin-3-yl)-4,6,7,8,9,10-hexahydro-pyrimido[1,2-a]azepine-3-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with 2-iminohomopiperidine hydroiodid [J. Med. Chem. (1996), 39, 669–672]and 1,8-diazabicyclo [5.4.0]undec-7-en in N,N-dimethylformamide at 100° C. to yield the 4-oxo-2-(1,2,4,5-tetrahydro-benzo[d]azepin-3-yl)-4,6,7,8,9,10-hexahydro-pyrimido[1,2-a]azepine-3-carbonitrile as colorless amorphous solid; MS: [M+H]$^+$=335.

EXAMPLE 128

4-Oxo-2-(1,2,4,5-tetrahydro-benzo[d]azepin-3-yl)-6,7,8,9-tetrahydro-4H-pyrido[1,2-a]pyrimidine-3-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with 2-iminopiperidine hydrochlorid [J. Med. Chem. (1996), 39, 669–672] and 1,8-diazabicyclo[5.4.0]undec-7-en in N,N-dimethylformamide at 100° C. to yield the 4-oxo-2-(1,2,4,5-tetrahydro-benzo[d]azepin-3-yl)-6,7,8,9-tetrahydro-4H-pyrido[1,2-a]pyrimidine-3-carbonitrile as yellow solid; m.p. 136.5–139.5° C.; MS: [M+H]$^+$=321.

EXAMPLE 129

5-Ethyl-6-hydroxymethyl-2-(1,2,4,5-tetrahydro-benzo[d]azepin-3-yl)-nicotinonitrile From the 5-ethyl-6-methyl-1-oxy-2-(1,2,4,5-tetrahydro-benzo[d]azepin-3-yl)-nicotinonitrile with trifluoroacetic anhydride in dichloromethane at reflux as light brown oil; MS: [M+H]$^+$=308; see example 130.

EXAMPLE 130

Trifluoro-acetic acid 5-cyano-3-ethyl-6-(1,2,4,5-tetrahydro-benzo[d]azepin-3-yl)-pyridin-2-ylmethyl ester A solution of 0.30 g (0.98 mmol) of 5-ethyl-6-methyl-1-oxy-2-(1,2,4,5-tetrahydro-benzo[d]azepin-3-yl)-nicotinonitrile and 3.0 g (14.2 mmol) of trifluoroacetic anhydride in 3.0 ml of dichloromethane was heated at reflux for 20 hours. The reaction mixture was then evaporated and the residue chromatographed on silica gel using a 99:1 v/v mixture of dichloromethane and methanol as eluent. Thus, 0.32 g (0.80 mmol), 82%, trifluoro-acetic acid 5-cyano-3-ethyl-6-(1,2,4,5-tetrahydro-benzo[d]azepin-3-yl)-pyridin-2-ylmethyl ester were obtained as yellow oil; MS: [M+H]$^+$=404; and 0.053 g (0.17 mmol), 18%, 5-ethyl-6-hydroxymethyl-2-(1,2,4,5-tetrahydro-benzo[d]azepin-3-yl)-nicotinonitrile as light brown oil; MS: [M+H]$^+$=308.

Preparation of the 5-ethyl-6-methyl-1-oxy-2-(1,2,4,5-tetrahydro-benzo[d]azepin-3-yl)-nicotinonitrile The 5-ethyl-6-methyl-1-oxy-2-(1,2,4,5-tetrahydro-benzo[d]azepin-3-yl)-nicotinonitrile used above was prepared by the following reaction sequence: i) treatment of the 2-chloro-5-ethyl-6-methyl-nicotinonitrile [J. Med. Chem. (1992), 35(21), 3784–91] with hydrogen peroxide in trifluoroacetic acid at reflux to yield the 2-chloro-5-ethyl-6-methyl-1-oxy-nicotinonitrile; ii) treatment of the 2-chloro-5-ethyl-6-methyl-1-oxy-nicotinonitrile in analogy to the procedure described in example 4 with the 2,3,4,5-tetrahydro-1H-benzo[d]azepine hydrochloride [J. Heterocycl. Chem. (1971), 8(5), 779–83] in N,N-dimethylformamide in the presence of N-ethyl-N,N-diisopropylamine at room temperature to yield the 5-ethyl-6-methyl-1-oxy-2-(1,2,4,5-tetrahydro-benzo[d]azepin-3-yl)-nicotinonitrile as yellow solid; m.p. 162–166° C.; MS: [M]$^+$=307.

EXAMPLE 131

3-(6-Ethoxy-2-methyl-5-nitro-pyrimidin-4-yl)-7-fluoro-2,3,4,5-tetrahydro-1H-benzo[d]azepine From the 6-(7-fluoro-1,2,4,5-tetrahydro-benzo[d]azepin-3-yl)-2-methyl-5-nitro-3H-pyrimidin-4-one (example 123) with iodoethane and potassium carbonate in N,N-dimethylformamide at room temperature as light yellow amorphous solid; MS: [M+H]$^+$=347; see example 132.

EXAMPLE 132

3-Ethyl-6-(7-fluoro-1,2,4,5-tetrahydro-benzo[d]azepin-3-yl)-2-methyl-5-nitro-3H-pyrimidin-4-one In analogy to the procedure described in example 3 the 6-(7-fluoro-1,2,4,5-tetrahydro-benzo[d]azepin-3-yl)-2-methyl-5-nitro-3H-pyrimidin-4-one (example 123) was treated with iodoethane in N,N-dimethylformamide in the presence of potassium carbonate at room temperature to yield the 3-ethyl-6-(7-fluoro-1,2,4,5-tetrahydro-benzo[d]azepin-3-yl)-2-methyl-5-nitro-3H-pyrimidin-4-one as yellow oil; MS: [M+H]$^+$=347; and the 3-(6-ethoxy-2-methyl-5-nitro-pyrimidin-4-yl)-7-fluoro-2,3,4,5-tetrahydro-1H-benzo[d]azepine as light yellow amorphous solid; MS: [M+H]$^+$=347.

EXAMPLE 133

1-Allyl-6-oxo-2-(2-phenoxy-ethylamino)-4-(1,2,4,5-tetrahydro-benzo[d]azepin-3-yl)-1,6-dihydro-pyrimidine-5-carbonitrile A suspension of 0.100 g (0.311 mmol) of the 1-allyl-2-amino-6-oxo-4-(1,2,4,5-tetrahydro-benzo[d]azepin-3-yl)-1,6-dihydro-pyrimidine-5-carbonitrile (example 109), 0.0738 g (0.367 mmol) of 2-phenoxyethyl bromide and 0.0887 g (0.662 mmol) of potassium carbonate in 1.0 ml of N,N-dimethylformamide was stirred at room temperature for 48 hours. The reaction mixture was then poured into 30 ml of ice-water, acidified with 1N hydrogen chloride and extracted 3 times with 50 ml of ethylacetate. The combined ethylacetate phases were dried over magnesium sulfate and evaporated under reduced pressure. The residue was chromatographed on silica gel using a 1:1 v/v mixture of dichloromethane and ethylacetate as eluent and then crystallized from ether. There was thus obtained 0.063 g (0.143 mmol), 46%, 1-allyl-6-oxo-2-(2-phenoxy-ethylamino)-4-(1,2,4,5-tetrahydro-benzo[d]azepin-3-yl)-1,6-dihydro-pyrimidine-5-carbonitrile as colorless solid; m.p. 157–160° C.; MS: [M+H]$^+$=442.

EXAMPLE 134

6-Oxo-2-(2-phenoxy-ethylamino)-4-(1,2,4,5-tetrahydro-benzo[d]azepin-3-yl)-1,6-dihydro-pyrimidine-5-carbonitrile 0.0065 g (0.283 mmol) of lithium borohydride were added to a suspension of 0.050 g (0.113 mmol) 1-allyl-6-oxo-2-(2-phenoxy-ethylamino)-4-(1,2,4,5-tetrahydro-benzo[d]azepin-3-yl)-1,6-dihydro-pyrimidine-5-carbonitrile (example 133), 0.0005 g (0.0023 mmol) of palladium(II) acetate and 0.0012 g (0.0045 mmol) of triphenylphoshin in 2.0 ml of tetrahydrofuran and the reaction mixture was stirred at room temperature for 1 hour. It was then treated with a few drops of acetone, poured into 30 ml of ice-water and extracted 3 times with 50 ml of ethylacetate. The combined ethylacetate phases were dried over magnesium sulfate and evaporated under reduced pressure. The residue formed was then chromatographed on silica gel using a 95:5 v/v mixture of dichloromethane and methanol as eluent and crystallized from ethylacetate/ether. There was thus obtained 0.028 g (0.070 mmol), 62%, 6-oxo-2-(2-phenoxy-ethylamino)-4-(1,2,4,5-tetrahydro-benzo[d]azepin-3-yl)-1,6-dihydro-pyrimidine-5-carbonitrile as beige solid; m.p. >200° C.; MS: [M+H]$^+$=402.

EXAMPLE 135

4-Allyloxy-2-diallylamino-6-(1,2,4,5-tetrahydro-benzo[d]azepin-3-yl)-pyrimidine-5-carbonitrile In analogy to the procedure described in example 3 the 2-amino-6-oxo-4-(1,2,4,5-tetrahydro-benzo[d]azepin-3-yl)-1,6-dihydro-pyrimidine-5-carbonitrile [example 13 b)] was treated with 3-bromo-1-propene in N,N-dimethylformamide in the presence of potassium carbonate to yield the 4-allyloxy-2-diallylamino-6-(1,2,4,5-tetrahydro-benzo[d]azepin-3-yl)-pyrimidine-5-carbonitrile as colorless solid; m.p. 125.9–130.0° C.; MS: [M+H]$^+$=402.

EXAMPLE 136

(S)-1-(2,2-Dimethyl-[1,3]dioxolan-4-ylmethyl)-2-methyl-6-oxo-4-(1,2,4,5-tetrahydro-benzo[d]azepin-3-yl)-1,6-dihydro-pyrimidine-5-carbonitrile From the 2-methyl-6-oxo-4-(1,2,4,5-tetrahydro-benzo[d]azepin-3-yl)-1,6-dihydro-pyrimidine-5-carbonitrile (example 17) with (R)-(−)-2,2-dimethyl-4-(hydroxymethyl)-1,3-dioxolane-p-toluene-sulfonate and potassium carbonate in N,N-dimethylformamide at room temperature as colorless solid; m.p. 166.2–168.3° C.; MS: [M+H]$^+$=395; see example 137.

EXAMPLE 137

(R)-4-(2,2-Dimethyl-[1,3]dioxolan-4-ylmethoxy)-2-methyl-6-(1,2,4,5-tetrahydro-benzo[d]azepin-3-yl)-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with the (R)-(−)-2,2-dimethyl-4-(hydroxymethyl)-1,3-dioxolane-p-toluene-sulfonate in N,N-dimethylformamide in the presence of potassium carbonate to yield the (R)-4-(2,2-dimethyl-[1,3]dioxolan-4-ylmethoxy)-2-methyl-6-(1,2,4,5-tetrahydro-benzo[d]azepin-3-yl)-pyrimidine- 5-carbonitrile as colorless solid; m.p. 109.8–111.5° C.; MS: [M+H]$^+$=395; and the (S)-1-(2,2-dimethyl-[1,3]dioxolan-4-ylmethyl)-2-methyl-6-oxo-4-(1,2,4,5-tetrahydro-benzo[d]azepin-3-yl)-1,6-dihydro-pyrimidine-5-carbonitrile as colorless solid; m.p. 166.2–168.3° C.; MS: [M+H]$^+$=395.

EXAMPLE 138

N-[1-Allyl-5-cyano-6-oxo-4-(1,2,4,5-tetrahydro-benzo[d]azepin-3-yl)-1,6-dihydro-pyrimidin-2-yl]-formamide From the 1-allyl-2-amino-6-oxo-4-(1,2,4,5-tetrahydro-benzo[d]azepin-3-yl)-1,6-dihydro-pyrimidine-5-carbonitrile (example 109) and potassium carbonate in N,N-dimethylformamide at 130° C. as yellow amorphous solid; MS: [M]$^+$=349; see example 139.

EXAMPLE 139

2-Amino-6-oxo-1-[Z]-propenyl-4-(1,2,4,5-tetrahydro-benzo[d]azepin-3-yl)-1,6-dihydro-pyrimidine-5-carbonitrile Heating of the 1-allyl-2-amino-6-oxo-4-(1,2,4,5-tetrahydro-benzo[d]azepin-3-yl)-1,6-dihydro-pyrimidine-5-carbonitrile (example 109) in the presence of potassium carbonate in N,N-dimethylformamide at 130° C. yielded the N-[1-allyl-5-cyano-6-oxo-4-(1,2,4,5-tetrahydro-benzo[d]azepin-3-yl)-1,6-dihydro-pyrimidin-2-yl ]-formamide as yellow amorphous solid; MS: [M]$^+$=349; and the 2-amino-6-oxo-1-[Z]-propenyl-4-(1,2,4,5-tetrahydro-benzo[d]azepin-3-yl)-1,6-dihydro-pyrimidine-5-carbonitrile as colorless solid; m.p. >200° C.; MS: [M+H]$^+$=322.

EXAMPLE 140

1-Allyl-6-oxo-2-(3-phenoxy-propylamino)-4-(1,2,4,5-tetrahydro-benzo[d]azepin-3-yl)-1,6-dihydro-pyrimidine-5-carbonitrile In analogy to the procedure described in example 133 the 1-allyl-2-amino-6-oxo-4-(1,2,4,5-tetrahydro-benzo[d]azepin-3-yl)-1,6-dihydro-pyrimidine-5-carbonitrile (example 109) was treated with the 3-phenoxypropyl bromide in N,N-dimethylformamide in the presence of potassium carbonate at room temperature to yield the 1-allyl-6-oxo-2-(3-phenoxy-propylamino)-4-(1,2,4,5-tetrahydro-benzo[d]azepin-3-yl)-1,6-dihydro-pyrimidine-5-carbonitrile as colorless solid; m.p. 157–159° C.; MS: [M+H]$^+$=456.

EXAMPLE 141

6-Oxo-2-(3-phenoxy-propylamino)-4-(1,2,4,5-tetrahydro-benzo[d]azepin-3-yl)-1,6-dihydro-pyrimidine-5-carbonitrile In analogy to the procedure described in example 134 the 1-allyl-6-oxo-2-(3-phenoxy-propylamino)-4-(1,2,4,5-tetrahydro-benzo[d]azepin-3-yl)-1,6-dihydro-pyrimidine-5-carbonitrile (example 140) was treated with lithium borohydride, palladium(II)acetate and triphenylphosphin in tetrahydrofuran to yield the 6-oxo-2-(3-phenoxy-propylamino)-4-(1,2,4,5-tetrahydro-benzo[d]azepin-3-yl)-1,6-dihydro-pyrimidine-5-carbonitrile as colorless solid; m.p. 175–180° C.; MS: [M+H]$^+$=416.

EXAMPLE 142

4-Allyloxy-2-(3-phenoxy-propylamino)-6-(1,2,4,5-tetrahydro-benzo[d]azepin-3-yl)-pyrimidine-5-carbonitrile In analogy to the procedure described in example 133 the 4-allyloxy-2-amino-6-(1,2,4,5-tetrahydro-benzo[d]azepin-3-yl)-pyrimidine-5-carbonitrile (example 111) was treated with the 3-phenoxypropyl bromide in N,N-dimethylformamide in the presence of potassium carbonate at 130° C. to yield the 4-allyloxy-2-(3-phenoxy-propylamino)-6-(1,2,4,5-tetrahydro-benzo[d]azepin-3-yl)-pyrimidine-5-carbonitrile as colorless amorphous solid; MS: [M+H]$^+$=456.

EXAMPLE 143

4-Allyloxy-6-(1,2,4,5-tetrahydro-benzo[d]azepin-3-yl)-2-(2,2,2-trifluoro-ethylamino)-pyrimidine-5-carbonitrile In analogy to the procedure described in example 133 the 4-allyloxy-2-amino-6-(1,2,4,5-tetrahydro-benzo[d]azepin-3-yl)-pyrimidine-5-carbonitrile (example 111) was treated with the 2,2,2-trifluoroethyl-trifluoromethanesulfonate in N,N-dimethylformamide in the presence of sodium hydride at room temperature to yield the 4-allyloxy-6-(1,2,4,5-tetrahydro-benzo[d]azepin-3-yl)-2-(2,2,2-trifluoro-ethylamino)-pyrimidine-5-carbonitrile as colorless amorphous solid; MS: [M+H]$^+$=404.

EXAMPLE 144

(S)-1-(2,3-Dihydroxy-propyl)-2-methyl-6-oxo-4-(1,2,4,5-tetrahydro-benzo[d]azepin-3-yl)-1,6-dihydro-pyrimidine-5-carbonitrile In analogy to the procedure described in example 70 the (S)-1-(2,2-dimethyl-[1,3]dioxolan-4-ylmethyl)-2-methyl-6-oxo-4-(1,2,4,5-tetrahydro-benzo[d]azepin-3-yl)-1,6-dihydro-pyrimidine-5-carbonitrile (example 136) was treated with 1.5N hydrogen chloride in methanol at room temperature to yield the (S)-1-(2,3-dihydroxy-propyl)-2-methyl-6-oxo-4-(1,2,4,5-tetrahydro-benzo[d]azepin-3-yl)-1,6-dihydro-pyrimidine-5-carbonitrile as colorless amorphous solid; MS: [M+H]$^+$=355.

EXAMPLE 145

(R)-4-(2,3-Dihydroxy-propoxy)-2-methyl-6-(1,2,4,5-tetrahydro-benzo[d]azepin-3-yl)-pyrimidine-5-carbonitrile In analogy to the procedure described in example 70 the (R)-4-(2,2-dimethyl-[1,3]dioxolan-4-ylmethoxy)-2-methyl-6-(1,2,4,5-tetrahydro-benzo[d]azepin-3-yl)-pyrimidine-5-carbonitrile (example 137) was treated with 1.5N hydrogen chloride in methanol at room temperature to yield the (R)-4-(2,3-dihydroxy-propoxy)-2-methyl-6-(1,2,4,5-tetrahydro-benzo[d]azepin-3-yl)-pyrimidine-5-carbonitrile as colorless amorphous solid; MS: [M+H]$^+$=355.

EXAMPLE 146

1-Allyl-2-(cyanomethyl-amino)-6-oxo-4-(1,2,4,5-tetrahydro-benzo[d]azepin-3-yl)-1,6-dihydro-pyrimidine-5-carbonitrile In analogy to the procedure described in example 3 the 1-allyl-2-amino-6-oxo-4-(1,2,4,5-tetrahydro-benzo[d]azepin-3-yl)-1,6-dihydro-pyrimidine-5-carbonitrile (example 109) was treated with the bromoacetonitrile in N,N-dimethylformamide in the presence of sodium hydride at room temperature to yield the 1-allyl-2-(cyanomethyl-amino)-6-oxo-4-(1,2,4,5-tetrahydro-benzo[d]azepin-3-yl)-1,6-dihydro-pyrimidine-5-carbonitrile as colorless solid; m.p. 198–203° C.; MS: [M+H]$^+$=361.

EXAMPLE 147

4-Amino-2-methyl-6-(1,2,4,5-tetrahydro-benzo[d]azepin-3-yl)-pyrimidine-5-carbonitrile a) In analogy to the procedure described in example 13 a) the [bis(methylthio)methylene]propanedinitrile was treated with the 2,3,4,5-tetrahydro-1H-benzo[d]azepine hydrochloride [J. Heterocycl. Chem. (1971), 8(5), 779–83] in dimethylsulfoxide in the presence of potassium carbonate at 80° C. to yield the 2-[methylsulfanyl-(1,2,4,5-tetrahydro-benzo[d]azepin-3-yl)-methylene]-malononitrile as a yellowish solid; m.p. 129–132.5° C.; MS: [M+H]$^+$=270.

b) In analogy to the procedure described in example 13 b) the 2-[methylsulfanyl-(1,2,4,5-tetrahydro-benzo[d]azepin- 3-yl)-methylene]-malononitrile was treated with the acetamidine hydrochloride and 1,8-diazabicyclo[5.4.0]undec-7-ene in N,N-dimethylformamide at 100° C. to yield the 4-amino-2-methyl-6-(1,2,4,5-tetrahydro-benzo[d]azepin-3-yl)-pyrimidine-5-carbonitrile as a light yellow solid; m.p. >200° C.; MS: [M+H]$^+$=280.

EXAMPLE 148

2-Methyl-4-(1,2,4,5-tetrahydro-benzo[d]azepin-3-yl)-6-(2,2,2-trifluoro-ethylamino)-pyrimidine-5-carbonitrile In analogy to the procedure described in example 133 the 4-amino-2-methyl-6-(1,2,4,5-tetrahydro-benzo[d]azepin-3-yl)-pyrimidine-5-carbonitrile (example 147) was treated with the 2,2,2-trifluoroethyl-trifluoromethanesulfonate in N,N-dimethylformamide in the presence of sodium hydride at 60° C. to yield the 2-methyl-4-(1,2,4,5-tetrahydro-benzo[d]azepin-3-yl)-6-(2,2,2-trifluoro-ethylamino)-pyrimidine-5-carbonitrile as colorless amorphous solid; MS: [M+H]$^+$=362.

EXAMPLE 149

4-Chloro-2-methylsulfanyl-6-(1,2,4,5-tetrahydro-benzo[d]azepin-3-yl)-pyrimidine-5-carbonitrile In analogy to the procedure described in example 46 a) the 4,6-dichloro-2-methylsulfanyl-pyrimidine-5-carbonitrile [J. Heterocycl. Chem. (1971), 8, 445–453] was treated with the 2,3,4,5-tetrahydro-1H-benzo[d]azepine hydrochloride [J. Heterocycl. Chem. (1971), 8(5), 779–83] in N,N-dimethylformamide in the presence of potassium carbonate at 50° C. to yield the 4-chloro-2-methylsulfanyl-6-(1,2,4,5-tetrahydro-benzo[d]azepin-3-yl)-pyrimidine-5-carbonitrile as colorless solid; m.p. 144–150° C.; MS: [M+H]$^+$=331.

EXAMPLE 150

3-[2-Ethyl-5-nitro-6-(2,2,2-trifluoro-ethoxy)-pyrimidin-4-yl]-2,3,4,5-tetrahydro-1H-benzo[d]azepine In analogy to the procedure described in example 99 the 3-[2-methyl-5-nitro-6-(2,2,2-trifluoro-ethoxy)-pyrimidin-4-yl]-2,3,4,5-tetrahydro-1H-benzo[d]azepine (example 119) was treated with the lithium-bis-(trimethylsilyl)amid and methyliodide in tetrahydrofuran between −70° C. and room temperature to yield the 3-[2-ethyl-5-nitro-6-(2,2,2-trifluoro-ethoxy)-pyrimidin-4-yl]-2,3,4,5-tetrahydro-1H-benzo[d]azepine as colorless oil; MS: [M+H]$^+$=397.

EXAMPLE 151

1-Allyl-6-oxo-2-[(pyridin-3-ylmethyl)-amino]-4-(1,2,4,5-tetrahydro-benzo[d]azepin-3-yl)-1,6-dihydro-pyrimidine-5-carbonitrile In analogy to the procedure described in example 133 the 1-allyl-2-amino-6-oxo-4-(1,2,4,5-tetrahydro-benzo[d]azepin-3-yl)-1,6-dihydro-pyrimidine-5-carbonitrile (example 109) was treated with the 3-(chloromethyl)pyridine hydrochloride and sodium hydride in N,N-dimethylformamide at room temperature to yield the 1-allyl-6-oxo-2-[(pyridin-3-ylmethyl)-amino]-4-(1,2,4,5-tetrahydro-benzo[d]azepin-3-yl)-1,6-dihydro-pyrimidine-5-carbonitrile as yellowish solid; m.p. >200° C.; MS: [M+H]$^+$=413.

EXAMPLE 152

1-Allyl-2-(2-ethoxy-ethylamino)-6-oxo-4-(1,2,4,5-tetrahydro-benzo[d]azepin-3-yl)-1,6-dihydro-pyrimidine-5-carbonitrile In analogy to the procedure described in example 133 the 1-allyl-2-amino-6-oxo-4-(1,2,4,5-tetrahydro-benzo[d]azepin-3-yl)-1,6-dihydro-pyrimidine-5-carbonitrile (example 109) was treated with the 2-ethoxyethyl methanesulfonate and potassium carbonate in N,N-dimethylformamide at 100° C. to yield the 1-allyl-2-(2-ethoxy-ethylamino)-6-oxo-4-(1,2,4,5-tetrahydro-benzo[d]azepin-3-yl)-1,6-dihydro-pyrimidine-5-carbonitrile as yellowish amorphous solid; MS: [M+H]$^+$=394.

EXAMPLE 153

2-(Cyanomethyl-amino)-6-oxo-4-(1,2,4,5-tetrahydro-benzo[d]azepin-3-yl)-1,6-dihydro-pyrimidine-5-carbonitrile In analogy to the procedure described in example 134 the 1-allyl-2-(cyanomethyl-amino)-6-oxo-4-(1,2,4,5-tetrahydro-benzo[d]azepin-3-yl)-1,6-dihydro-pyrimidine-5-carbonitrile (example 146) was treated with lithium borohydride, palladium(II)acetate and triphenylphoshin in tetrahydrofuran at room temperature to yield the 2-(cyanomethyl-amino)-6-oxo-4-(1,2,4,5-tetrahydro-benzo[d]azepin-3-yl)-1,6-dihydro-pyrimidine-5-carbonitrile as brownish solid; m.p. >200° C.; MS: [M+H]$^+$=321.

EXAMPLE 154

N-[5-cyano-1-ethyl-6-oxo-4-(1,2,4,5-tetrahydro-benzo[d]azepin-3-yl)-1,6-dihydro-pyrimidin-2-yl]-formamide A suspension of 0.104 g (0.336 mmol) of 2-amino-1-ethyl-6-oxo-4-(1,2,4,5-tetrahydro-benzo[d]azepin-3-yl)-1,6-dihydro-pyrimidine-5-carbonitrile (example 30), 0.6 ml of ethylformiate and 0.093g (0.67 mmol) of potassium carbonate in 1.2 ml of N,N-dimethylformamide was stirred at 120° C. for 30 hours. The reaction mixture was then poured into 30 ml of ice/1N hydrogen chloride solution and filtered. The residue was chromatographed on silica gel using a 1:1 v/v mixture of dichloromethane and ethylacetate as eluent and crystallized from ether. There was thus obtained 0.038 g (0.113 mmol), 33.5%, N-[5-cyano-1-ethyl-6-oxo-4-(1,2,4,5-tetrahydro-benzo[d]azepin-3-yl)-1,6-dihydro-pyrimidin-2-yl]-formamide as colorless solid; m.p. >200° C.; MS: [M+H]$^+$=338.

EXAMPLE 155

4-(2-Hydroxy-ethylamino)-2-methylsulfanyl-6-(1,2,4,5-tetrahydro-benzo[d]azepin-3-yl)-pyrimidine-5-carbonitrile In analogy to the procedure described in example 48 the 4-chloro-2-methylsulfanyl-6-(1,2,4,5-tetrahydro-benzo[d]azepin-3-yl)-pyrimidine-5-carbonitrile (example 149) was treated with the ethanolamine in ethanol at 80° C. to yield the 4-(2-hydroxy-ethylamino)-2-methylsulfanyl-6-(1,2,4,5-tetrahydro-benzo[d]azepin-3-yl)-pyrimidine-5-carbonitrile as colorless foam; MS: [M+H]$^+$=356.

EXAMPLE 156

4-(3-Imidazol-1-yl-propylamino)-2-methylsulfanyl-6-(1,2,4,5-tetrahydro-benzo[d]azepin-3-yl)-pyrimidine-5-carbonitrile In analogy to the procedure described in example 48 the 4-chloro-2-methylsulfanyl-6-(1,2,4,5-tetrahydro-benzo[d]azepin-3-yl)-pyrimidine-5-carbonitrile (example 149) was treated with the 1-(3-aminopropyl)-imidazole in dioxane in the presence of potassium carbonate at 90° C. to yield the 4-(3-imidazol-1-yl-propylamino)-2-methylsulfanyl-6-(1,2,4,5-tetrahydro-benzo[d]azepin-3-yl)-pyrimidine-5-carbonitrile as colorless solid; m.p. 131.0–133.5° C.; MS: [M+H]$^+$=420.

EXAMPLE 157

5-Methyilsulfanyl-7-(1,2,4,5-tetrahydro-benzo[d]azepin-3-yl)-2,3-dihydro-imidazo[1,2-c]pyrimidine-8-carbonitrile hydrochloride A solution of 0.160 g (0.41 mmol) of 4-(2-hydroxyethylamino)-2-methylsulfanyl-6-(1,2,4,5-tetrahydro-benzo[d]azepin-3-yl)-pyrimidine-5-carbonitrile (example 155) and 0.5 ml (6.8 mmol) of thionyl chloride in 5.0 ml of chloroform was stirred at 90° C. for 2 hours. The reaction mixture was then evaporated under reduced pressure, suspended in dichloromethane and the not soluble crystals filtered off. There was thus obtained 0.050 g (0.134 mmol), 33%, of the 5-methylsulfanyl-7-(1,2,4,5-tetrahydro-benzo[d]azepin-3-yl)-2,3-dihydro-imidazo[1,2-c]pyrimidine-8-carbonitrile hydrochloride as yellow solid; m.p. >200° C.; MS: [M+H]$^+$=374.

EXAMPLE 158

3-(2-Methyl-5-nitro-6-oxo-1,6-dihydro-pyrimidin-4-yl)-2,3,4,5-tetrahydro-benzo[d]azepin-1-one In analogy to the procedure described in example 4 the 6-bromo-2-methyl-5-nitro-3H-pyrimidin-4-one (see example 66) was treated with the 2,3,4,5-tetrahydro-benzo[d]azepin-1-one hydrochloride (1:1) [J. Chem. Soc., Perkin Trans. 1 (1975), (7), 622–6] in N,N-dimethylformamide in the presence of N-aethyldiisopropylamine at room temperature to yield the 3-(2-methyl-5-nitro-6-oxo-1,6-dihydro-pyrimidin-4-yl)-2,3,4,5-tetrahydro-benzo[d]azepin-1-one as light yellow amorphous solid; MS: [M+H]$^+$=315.

EXAMPLE 159

[rac]-6-(1-Hydroxy-1,2,4,5-tetrahydro-benzo[d]azepin-3-yl)-2-methyl-5-nitro-3H-pyrimidin-4-one In analogy to the procedure described in example 4 the (6-bromo-2-methyl-5-nitro-3H-pyrimidin-4-one (see example 66) was treated with the [rac]-2,3,4,5-tetrahydro-1H-benzo[d]azepin-1-ol [J. Chem. Soc., Perkin Trans. 1 (1975), (7), 622–6] in N,N-dimethylformamide in the presence of N-aethyldiisopropylamine at room temperature to yield the [rac]-6-(1-hydroxy-1,2,4,5-tetrahydro-benzo[d]azepin-3-yl)-2-methyl-5-nitro-3H-pyrimidin-4-one as light yellow solid; m.p. >200° C.; MS: [M–H]$^-$=315.

EXAMPLE 160

2-Methylsulfanyl-4-(3-pyridin-2-yl-propoxy)-6-(1,2,4,5-tetrahydro-benzo[d]azepin-3-yl)-pyrimidine-5-carbonitrile In analogy to the procedure described in example 47 a) the 4-chloro-2-methylsulfanyl-6-(1,2,4,5-tetrahydro-benzo[d]azepin-3-yl)-pyrimidine-5-carbonitrile (example 149) was treated with the 3-(3-pyridyl)-1-propanol in tetrahydrofuran in the presence of sodium hydride at room temperature to yield the 2-methylsulfanyl-4-(3-pyridin-2-yl-propoxy)-6-(1,2,4,5-tetrahydro-benzo[d]azepin-3-yl)-pyrimidine-5-carbonitrile as light brown oil; MS: [M+H]$^+$=432.

EXAMPLE 161

2-Methylsulfanyl-4-[2-(2-oxo-pyrrolidin-1-yl)-ethoxy]-6-(1,2,4,5-tetrahydro-benzo[d]azepin-3-yl)-pyrimidine-5-carbonitrile In analogy to the procedure described in example 47 a) the 4-chloro-2-methylsulfanyl-6-(1,2,4,5-tetrahydro-benzo[d]azepin-3-yl)-pyrimidine-5-carbonitrile (example 149) was treated with the 1-(2-hydroxyethyl)-2-pyrrolidone in tetrahydrofuran in the presence of sodium hydride at room temperature to yield the 2-methylsulfanyl-4-[2-(2-oxo-pyrrolidin-1-yl)-ethoxy]-6-(1,2,4,5-tetrahydro-benzo[d]azepin-3-yl)-pyrimidine-5-carbonitrile as colorless solid; m.p. 126–128.5° C.; MS: [M+H]$^+$=424.

EXAMPLE 162

4-(4-Methyl-pentyloxy)-2-methylsulfanyl-6-(1,2,4,5-tetrahydro-benzo[d]azepin-3-yl)-pyrimidine-5-carbonitrile In analogy to the procedure described in example 47 a) the 4-chloro-2-methylsulfanyl-6-(1,2,4,5-tetrahydro-benzo[d]azepin-3-yl)-pyrimidine-5-carbonitrile (example 149) was treated with the 4-methyl-1-pentanol in tetrahydrofuran in the presence of sodium hydride at room temperature to yield the 4-(4-methyl-pentyloxy)-2-methylsulfanyl-6-(1,2,4,5-tetrahydro-benzo[d]azepin-3-yl)-pyrimidine-5-carbonitrile as colorless oil; MS: [M+H]$^+$=397.

EXAMPLE 163

2-Methylsulfanyl-4-(2-morpholin-4-yl-ethoxy)-6-(1,2,4,5-tetrahydro-benzo[d]azepin-3-yl)-pyrimidine-5-carbonitrile In analogy to the procedure described in example 47 a) the 4-chloro-2-methylsulfanyl-6-(1,2,4,5-tetrahydro-benzo[d]azepin-3-yl)-pyrimidine-5-carbonitrile (example 149) was treated with the 4-(2-hydroxyethyl)-morpholine in tetrahydrofuran in the presence of sodium hydride at room temperature to yield the 2-methylsulfanyl-4-(2-morpholin-4-yl-ethoxy)-6-(1,2,4,5-tetrahydro-benzo[d]azepin-3-yl)-pyrimidine-5-carbonitrile as colorless oil; MS: [M+H]$^+$=426.

EXAMPLE 164

4-Amino-2-methylsulfanyl-6-(1,2,4,5-tetrahydro-benzo[d]azepin-3-yl)-pyrimidine-5-carbonitrile In analogy to the procedure described in example 48 the 4-chloro-2-methylsulfanyl-6-(1,2,4,5-tetrahydro-benzo[d]azepin-3-yl)-pyrimidine-5-carbonitrile (example 149) was treated with aqueous ammonia at room temperature to yield the 4-amino-2-methylsulfanyl-6-(1,2,4,5-tetrahydro-benzo[d]azepin-3-yl)-pyrimidine-5-carbonitrile as colorless solid; m.p. >200° C.; MS: [M+H]$^+$=312.

EXAMPLE 165

4-Allyloxy-2-methylsulfanyl-6-(1,2,4,5-tetrahydro-benzo[d]azepin-3-yl)-pyrimidine-5-carbonitrile In analogy to the procedure described in example 47 a) the 4-chloro-2-methylsulfanyl-6-(1,2,4,5-tetrahydro-benzo[d]azepin-3-yl)-pyrimidine-5-carbonitrile (example 149) was treated with the allylalkohol in tetrahydrofuran in the presence of sodium hydride at room temperature to yield the 4-allyloxy-2-methylsulfanyl-6-(1,2,4,5-tetrahydro-benzo[d]azepin-3-yl)-pyrimidine-5-carbonitrile as colorless solid; m.p. 102.6–104.8° C.; MS: [M+H]$^+$=353.

EXAMPLE 166

2-Methylsulfanyl-4-(1,2,4,5-tetrahydro-benzo[d]azepin-3-yl)-6-(2,2,2-trifluoro-ethoxy)-pyrimidine-5-carbonitrile In analogy to the procedure described in example 47 a) the 4-chloro-2-methylsulfanyl-6-(1,2,4,5-tetrahydro-benzo[d]

azepin-3-yl)-pyrimidine-5-carbonitrile (example 149) was treated with the trifluoroethanol in tetrahydrofuran in the presence of sodium hydride at room temperature to yield the 2-methylsulfanyl-4-(1,2,4,5-tetrahydro-benzo[d]azepin-3-yl)-6-(2,2,2-trifluoro-ethoxy)-pyrimidine-5-carbonitrile as colorless solid; m.p. 107.9–110.5° C.; MS: [M+H]$^+$=395.

EXAMPLE 167

2-Methylsulfanyl-4-(2-morpholin-4-yl-ethylamino)-6-(1,2,4,5-tetrahydro-benzo[d]azepin-3-yl)-pyrimidine-5-carbonitrile In analogy to the procedure described in example 48 the 4-chloro-2-methylsulfanyl-6-(1,2,4,5-tetrahydro-benzo[d]azepin-3-yl)-pyrimidine-5-carbonitrile (example 149) was treated with the aminoethyl-morpholine in dioxane in the presence of potassium carbonate at 90° C. to yield the 2-methylsulfanyl-4-(2-morpholin-4-yl-ethylamino)-6-(1,2,4,5-tetrahydro-benzo[d]azepin-3-yl)-pyrimidine-5-carbonitrile as colorless amorphous solid; MS: [M+H]$^+$=425.

EXAMPLE 168

4-(2-Methoxy-ethoxy)-2-methylsulfanyl-6-(1,2,4,5-tetrahydro-benzo[d]azepin-3-yl)-pyrimidine-5-carbonitrile In analogy to the procedure described in example 47 a) the 4-chloro-2-methylsulfanyl-6-(1,2,4,5-tetrahydro-benzo[d]azepin-3-yl)-pyrimidine-5-carbonitrile (example 149) was treated with the diethylen-glycol-monomethylether in tetrahydrofuran in the presence of sodium hydride at room temperature to yield the 4-(2-methoxy-ethoxy)-2-methylsulfanyl-6-(1,2,4,5-tetrahydro-benzo[d]azepin-3-yl)-pyrimidine-5-carbonitrile as colorless amorphous solid; MS: [M+H]$^+$=371.

EXAMPLE 169

[rac]-3-(6-Ethoxy-2-methyl-5-nitro-pyrimidin-4-yl)-2,3,4,5-tetrahydro-1H-benzo[d]azepin-1-ol From [rac]-6-(1-hydroxy-1,2,4,5-tetrahydro-benzo[d]azepin-3-yl)-2-methyl-5-nitro-3H-pyrimidin-4-one (example 159) and iodoethane, potassium carbonate in N,N-dimethylformamide at room temperature as light yellow oil; MS: [M+H]$^+$=345; see example 170.

EXAMPLE 170

[rac]-3-Ethyl-6-(1-hydroxy-1,2,4,5-tetrahydro-benzo[d]azepin-3-yl)-2-methyl-5-nitro-3H-pyrimidin-4-one In analogy to the procedure described in example 3 the [rac]-6-(1-hydroxy-1,2,4,5-tetrahydro-benzo[d]azepin-3-yl)-2-methyl-5-nitro-3H-pyrimidin-4-one (example 159) was treated with the iodoethane in N,N-dimethylformamide in the presence of potassium carbonate at room temperature to yield the [rac]-3-ethyl-6-(1-hydroxy-1,2,4,5-tetrahydro-benzo[d]azepin-3-yl)-2-methyl-5-nitro-3H-pyrimidin-4-one as yellow amorphous solid; MS: [M+H]$^+$=345; and the [rac]-3-(6-ethoxy-2-methyl-5-nitro-pyrimidin-4-yl)-2,3,4,5-tetrahydro-1H-benzo[d]azepin-1-ol as light yellow oil; MS: [M+H]$^+$=345.

EXAMPLE 171

4-Chloro-6-(1,2,4,5-tetrahydro-benzo[d]azepin-3-yl)-2-(2,2,2-trifluoro-ethoxy)-pyrimidine-5-carbonitrile In analogy to the procedure described in example 47 a) the 4-chloro-2-methanesulfonyl-6-(1,2,4,5-tetrahydro-benzo[d]azepin-3-yl)-pyrimidine-5-carbonitrile was treated with the 2,2,2-trifluoroethanol in tetrahydrofuran in the presence of sodium hydride at room temperature to yield the 4-chloro-6-(1,2,4,5-tetrahydro-benzo[d]azepin-3-yl)-2-(2,2,2-trifluoro-ethoxy)-pyrimidine-5-carbonitrile as colorless solid; m.p. 165–167° C.; MS: [M+H]$^+$=383.

Preparation of the 4-chloro-2-methanesulfonyl-6-(1,2,4,5-tetrahydro-benzo[d]azepin-3-yl)-pyrimidine-5-carbonitrile Oxidation of the 4-chloro-2-methylsulfanyl-6-(1,2,4,5-tetrahydro-benzo[d]azepin-3-yl)-pyrimidine-5-carbonitrile (example 149) with m-chloroperbenzoic acid in dichloromethane at room temperature yielded the 4-chloro-2-methanesulfonyl-6-(1,2,4,5-tetrahydro-benzo[d]azepin-3-yl)-pyrimidine-5-carbonitrile as colorless solid; MS: [M+H]$^+$=363.

EXAMPLE 172

2-(3-Phenoxy-propoxy)-4-(1 2,4,5-tetrahydro-benzo[d]azepin-3-yl)-6-(2,2,2-trifluoro-ethoxy)-pyrimidine-5-carbonitrile In analogy to the procedure described in example 47 a) the 2-methanesulfonyl-4-(1,2,4,5-tetrahydro-benzo[d]azepin-3-yl)-6-(2,2,2-trifluoro-ethoxy)-pyrimidine-5-carbonitrile was treated with the 3-phenoxypropanol in tetrahydrofuran in the presence of sodium hydride at room temperature to yield the 2-(3-phenoxy-propoxy)-4-(1,2,4,5-tetrahydro-benzo[d]azepin-3-yl)-6-(2,2,2-trifluoro-ethoxy)-pyrimidine-5-carbonitrile as colorless oil; MS: [M+H]$^+$=499.

Preparation of the 2-methanesulfonyl-4-(1,2,4,5-tetrahydro-benzo[d]azepin-3-yl)-6-(2,2,2-trifluoro-ethoxy)-pyrimidine-5-carbonitrile Oxidation of the 2-methylsulfanyl-4-(1,2,4,5-tetrahydro-benzo[d]azepin-3-yl)-6-(2,2,2-trifluoro-ethoxy)-pyrimidine-5-carbonitrile (example 166) with m-chloroperbenzoic acid in dichloromethane at room temperature yielded the 2-methanesulfonyl-4-(1,2,4,5-tetrahydro-benzo[d]azepin-3-yl)-6-(2,2,2-trifluoro-ethoxy)-pyrimidine-5-carbonitrile as colorless solid; m.p. 166–169° C.; MS: [M+H]$^+$=427.

EXAMPLE 173

2-(3-Pyridin-2-yl-propoxy)-4-(1,2,4,5-tetrahydro-benzo[d]azepin-3-yl)-6-(2,2,2-trifluoro-ethoxy)-pyrimidine-5-carbonitrile In analogy to the procedure described in example 47 a) the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the 3-(3-pyridyl)-1-propanol in tetrahydrofuran in the presence of sodium hydride at room temperature to yield the 2-(3-pyridin-2-yl-propoxy)-4-(1,2,4,5-tetrahydro-benzo[d]azepin-3-yl)-6-(2,2,2-trifluoro-ethoxy)-pyrimidine-5-carbonitrile as colorless oil; MS: [M+H]$^+$=484.

EXAMPLE 174

2-(3-Morpholin-4-yl-propylamino)-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3- yl)-6-(2,2,2-trifluoro-ethoxy)-pyrimidine-5-carbonitrile (example 172) was treated with the 4-(3-aminopropyl)-morpholine in tetrahydrofuran at 50° C. to yield the 2-(3-morpholin-4-yl-propylamino)-4-(1,2,4,5-tetrahydro-benzo[d]azepin-3-yl)-6-(2,2,2-trifluoro-ethoxy)-pyrimidine-5-carbonitrile as colorless oil; MS: [M+H]$^+$=491.

EXAMPLE 175

5-Methylsulfanyl-7-(1,2,4,5-tetrahydro-benzo[d]azepin-3-yl)-[1,2,4]triazolo[4,3-c]pyrimidine-8-carbonitrile 0.30 g (0.83 mmol) of 4-hydrazino-2-methylsulfanyl-6-(1,2,4,5-tetrahydro-benzo[d]azepin-3-yl)-pyrimidine-5-carbonitrile were suspended in 1.0 ml of triethyl orthoformate and the reaction mixture was stirred at 110° C. during 24 hours. Subsequently, it was evaporated under reduced pressure and the residue obtained was purified by chromatography on silica gel using a 95:5 v/v mixture of dichloromethane and methanol as eluent to yield 0.183 g (0.54 mmol), 66%, of the 5-methylsulfanyl-7-(1,2,4,5-tetrahydro-benzo[d]azepin-3-yl)-[1,2,4]triazolo[4,3-c]pyrimidine-8-carbonitrile as light brown solid; m.p. >200° C.; MS: [M]$^+$=336.

Preparation of the 4-hydrazino-2-methylsulfanyl-6-(1,2,4,5-tetrahydro-benzo[d]azepin-3-yl)-pyrimidine-5-carbonitrile The 4-chloro-2-methylsulfanyl-6-(1,2,4,5-tetrahydro-benzo[d]azepin-3-yl)-pyrimidine-5-carbonitrile (example 149) and hydrazine hydrate were heated in a mixture of dioxane and water at 100° C. to yield the 4-hydrazino-2-methylsulfanyl-6-(1,2,4,5-tetrahydro-benzo[d]azepin-3-yl)-pyrimidine-5-carbonitrile as orange solid; m.p. >200° C.; MS: [M+H]$^+$=327.

EXAMPLE 176

2-Methyl-4-(1,1,2,2-tetrafluoro-ethoxy)-6-(1,2,4,5-tetrahydro-benzo[d]azepin-3-yl)-pyrimidine-5-carbonitrile 3.0 ml of tetrafluoroethylene were condensed at −180° C. into a mixture of 0.20 g (0.71 mmol) of 2-methyl-6-oxo-4-(1,2,4,5-tetrahydro-benzo[d]azepin-3-yl)-1,6-dihydro-pyrimidine-5-carbonitrile (example 17) and 0.037 g (0.86 mmol) of sodium hydride dispersion (55% in mineral oil) in 2.0 ml of N,N-dimethylformamide and the reaction mixture was then heated in an autoclave at 120° C. for 16 hours. Subsequently, it was poured into 50 ml of an ice/1N HCl mixture and extracted three times with 50 ml of dichloromethane. The combined organic phases were washed twice with 50 ml of water, dried over magnesium sulphate, evaporated under reduced pressure and dried in a high vacuum. The thus obtained crude product was purified by chromatography on silica gel using a hexane/ethyl acetate mixture as eluent to yield 0.025 g (0.066 mmol), 9.3%, of 2-methyl-4-(1,1,2,2-tetrafluoro-ethoxy)-6-(1,2,4,5-tetrahydro-benzo[d]azepin-3-yl)-pyrimidine-5-carbonitrile as yellow amorphous solid; MS: [M+H]$^+$=381.

EXAMPLE 177

1-Dimethylamino-2-methyl-6-oxo-4-(1,2,4,5-tetrahydro-benzo[d]azepin-3-yl)-1,6-dihydro-pyrimidine-5-carbonitrile In analogy to the procedure described in example 17 the Z and/or E 2-cyano-3-methylsulfanyl-3-(1,2,4,5-tetrahydro-benzo[d]azepin-3-yl)-acrylic acid ethyl ester [example 13 a)] was treated with the acetamide dimethylhydrazone [J. Heterocycl. Chem. 18, 319 (1981)] and 1,8-diazabicyclo[5.4.0]undec-7-en in N,N-dimethylformamide at 100° C. to yield the 1-dimethylamino-2-methyl-6-oxo-4-(1,2,4,5-tetrahydro-benzo[d]azepin-3-yl)-1,6-dihydro-pyrimidine-5-carbonitrile as colorless solid; m.p. 134.4–136.3° C.; MS: [M]$^+$=324.

EXAMPLE 178

4-Fluoro-2-methyl-6-(1,2,4,5-tetrahydro-benzo[d]azepin-3-yl)-pyrimidine-5-carbonitrile 3.0 ml of tetrafluoroethylene were condensed at −180° C. into a mixture of 0.40 g (1.42 mmol) of 2-methyl-6-oxo-4-(1,2,4,5-tetrahydro-benzo[d]azepin-3-yl)-1,6-dihydro-pyrimidine-5-carbonitrile (example 17) and 0.296 g (2.14 mmol) of potassium carbonate in 3.0 ml of N,N-dimethylformamide and the reaction mixture was then heated in an autoclave at 100° C. for 72 hours. Subsequently, it was poured into 50 ml of an ice/1N HCl mixture and extracted three times with 50 ml of dichloromethane. The combined organic phases were washed twice with 50 ml of water, dried over magnesium sulphate, evaporated under reduced pressure and dried in a high vacuum. The thus obtained crude product was purified by chromatography on silica gel using dichloromethane as eluent to yield 0.097 g (0.034 mmol), 2.4%, of 4-fluoro-2-methyl-6-(1,2,4,5-tetrahydro-benzo[d]azepin-3-yl)-pyrimidine-5-carbonitrile as yellowish amorphous solid; MS: [M]$^+$=282.

EXAMPLE 179

2-Cyclopropyl-4-(1,2,4,5-tetrahydro-benzo[d]azepin-3-yl)-6-(2,2,2-trifluoro-ethoxy)-pyrimidine-5-carbonitrile From the 2-cyclopropyl-6-oxo-4-(1,2,4,5-tetrahydro-benzo[d]azepin-3-yl)-1,6-dihydro-pyrimidine-5-carbonitrile (example 18) and 2,2,2-trifluoroethyl trifluoromethane-sulfonate in N,N-dimethylformamide in the presence of potassium carbonate as colorless solid; m.p. 116.5–118° C.; MS: [M+H]$^+$=389; see example 180.

EXAMPLE 180

2-Cyclopropyl-6-oxo-4-(1,2,4,5-tetrahydro-benzo[d]azepin-3-yl)-1-(2,2,2-trifluoro-ethyl)-1,6-dihydro-pyrimidine-5-carbonitrile In analogy to the procedure described in example 3 the 2-cyclopropyl-6-oxo-4-(1,2,4,5-tetrahydro-benzo[d]azepin-3-yl)-1,6-dihydro-pyrimidine-5-carbonitrile (example 18) was treated with the 2,2,2-trifluoroethyl trifluoromethane-sulfonate in N,N-dimethylformamide in the presence of potassium carbonate to yield the 2-cyclopropyl-6-oxo-4-(1,2,4,5-tetrahydro-benzo[d]azepin-3-yl)-1-(2,2,2-trifluoro-ethyl)-1,6-dihydro-pyrimidine-5-carbonitrile as colorless solid; m.p. 176–179.5° C.; MS: [M+H]$^+$=389; and the 2-cyclopropyl-4-(1,2,4,5-tetrahydro-benzo[d]azepin-3-yl)-6-(2,2,2-trifluoro-ethoxy))-pyrimidine-5-carbonitrile as colorless solid; m.p. 116.5–118° C.; MS: [M+H]$^+$=389.

EXAMPLE 181

2-(2-Morpholin-4-yl-ethylamino)-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3- yl)-6-(2,2,2-trifluoro-ethoxy)-pyrimidine-5-carbonitrile (example 172) was treated with the 2-morpholin-4-yl-ethylamine in tetrahydrofuran at 80° C. to yield the 2-(2-morpholin-4-yl-ethylamino)-4-(1,2,4,5-tetrahydro-benzo[d]azepin-3-yl)-6-(2,2,2-trifluoro-ethoxy)-pyrimidine-5-carbonitrile as colorless amorphous solid; MS: [M+H]$^+$=477.

EXAMPLE 182

2-Oxo-4-(1,2,4,5-tetrahydro-benzo[d]azepin-3-yl)-6-(2,2,2-trifluoro-ethoxy)-1,2-dihydro-pyrimidine-5-carbonitrile 0.050 g (0.12 mmol) of the 2-methanesulfonyl-4-(1,2,4,5-tetrahydro-benzo[d]azepin-3-yl)-6-(2,2,2-trifluoro-ethoxy)-pyrimidine-5-carbonitrile (example 172) were dissolved in 3.0 ml of dioxane, treated with 0.04 ml of 6M aqueous potassium hydroxide solution and the reaction mixture was stirred at 80° C. during 16 hours. Subsequently, it was evaporated under reduced pressure, 50 ml of water were added and the mixture extracted three times with 50 ml of dichloromethane. The combined organic phases were washed twice with 50 ml of water, dried over magnesium sulphate, evaporated under reduced pressure and dried in a high vacuum. The residue obtained was crystallized from dichlomethane to yield 0.030 g (0.082 mmol), 69%, of the 2-oxo-4-(1,2,4,5-tetrahydro-benzo[d]azepin-3-yl)-6-(2,2,2-trifluoro-ethoxy)-1,2-dihydro-pyrimidine-5-carbonitrile as colorless solid; m.p. 196–198° C.; MS: [M]$^+$=365.

EXAMPLE 183

6-Oxo-2-propyl-4-(1,2,4,5-tetrahydro-benzo[d]azepin-3-yl)-1-(2,2,2-trifluoro-ethyl)-1,6-dihydro-pyrimidine-5-carbonitrile From the 6-oxo-2-propyl-4-(1,2,4,5-tetrahydro-benzo[d]azepin-3-yl)-1,6-dihydro-pyrimidine-5-carbonitrile (example 23) and 2,2,2-trifluoroethyl trifluoromethane-sulfonate in N,N-dimethylformamide in the presence of potassium carbonate as colorless solid; m.p. 165–167° C.; MS: [M+H]$^+$=391; see example 184.

EXAMPLE 184

2-Propyl-4-(1,2,4,5-tetrahydro-benzo[d]azepin-3-yl)-6-(2,2,2-trifluoro-ethoxy)-pyrimidine-5-carbonitrile In analogy to the procedure described in example 3 the 6-oxo-2-propyl-4-(1,2,4,5-tetrahydro-benzo[d]azepin-3-yl)-1,6-dihydro-pyrimidine-5-carbonitrile (example 23) was treated with the 2,2,2-trifluoroethyl trifluoromethane-sulfonate in N,N-dimethylformamide in the presence of potassium carbonate at room temperature to yield the 6-oxo-2-propyl-4-(1,2,4,5-tetrahydro-benzo[d]azepin-3-yl)-1-(2,2,2-trifluoro-ethyl)-1,6-dihydro-pyrimidine-5-carbonitrile as colorless solid; m.p. 165–167° C.; MS: [M+H]$^+$=391; and the 2-propyl-4-(1,2,4,5-tetrahydro-benzo[d]azepin-3-yl)-6-(2,2,2-trifluoro-ethoxy)-pyrimidine-5-carbonitrile as colorless solid; m.p. 104–106° C.; MS: [M+H]$^+$=391.

EXAMPLE 185

[rac]-Acetic acid 3-(1-ethyl-2-methyl-5-nitro-6-oxo-1,6-dihydro-pyrimidin-4-yl)-2,3,4,5-tetrahydro-1H-benzo[d]azepin-1-yl ester Treatment of the [rac]-3-ethyl-6-(1-hydroxy-1,2,4,5-tetrahydro-benzo[d]azepin-3-yl)-2-methyl-5-nitro-3H-pyrimidin-4-one (example 170) with acetic anhydride and trietylamine in dichloromethane at room temperature yielded the [rac]-acetic acid 3-(1-ethyl-2-methyl-5-nitro-6-oxo-1,6-dihydro-pyrimidin-4-yl)-2,3,4,5-tetrahydro-1H-benzo[d]azepin-1-yl ester as light yellow foam; MS: [M+H]$^+$=387.

EXAMPLE 186

3-(3-Hydroxy-propyl)-2-methyl-5-nitro-6-(1,2,4,5-tetrahydro-benzo[d]azepin-3-yl)-3H-pyrimidin-4-one From the 2-methyl-5-nitro-6-(1,2,4,5-tetrahydro-benzo[d]azepin-3-yl)-pyrimidin-4-ol (example 1) and 3-chloro-1-propanol, potassium iodide, potassium carbonate in N,N-dimethylformamide at 50° C. as yellow oil; MS: [M+H]$^+$=359; see example 187.

EXAMPLE 187

3-[2-Methyl-5-nitro-6-(1,2,4,5-tetrahydro-benzo[d]azepin-3-yl)-pyrimidin-4-yloxy]-propan-1-ol In analogy to the procedure described in example 3 the 2-methyl-5-nitro-6-(1,2,4,5-tetrahydro-benzo[d]azepin-3-yl)-pyrimidin-4-ol (example 1) was treated with 3-chloro-1-propanol, potassium iodide and potassium carbonate in N,N-dimethylformamide at 50° C. to yield the 3-[2-methyl-5-nitro-6-(1,2,4,5-tetrahydro-benzo[d]azepin-3-yl)-pyrimidin-4-yloxy]-propan-1-ol as yellow oil; MS: [M+H]$^+$=359; and the 3-(3-hydroxy-propyl)-2-methyl-5-nitro-6-(1,2,4,5-tetrahydro-benzo[d]azepin-3-yl)-3H-pyrimidin-4-one as yellow oil; MS: [M+H]$^+$=359.

EXAMPLE 188

2-(2-Morpholin-4-yl-ethoxy)-4-(2-morpholin-4-yl-ethylamino)-6-(1,2,4,5-tetrahydro-benzo[d]azepin-3-yl)-pyrimidine-5-carbonitrile In analogy to the procedure described in example 48 the 4-chloro-2-(2-morpholin-4-yl-ethoxy)-6-(1,2,4,5-tetrahydro-benzo[d]azepin-3-yl)-pyrimidine-5-carbonitrile was treated with the 4-(2-aminoethyl)-morpholine in dioxane at 80° C. during 15 hours to yield the 2-(2-morpholin-4-yl-ethoxy)-4-(2-morpholin-4-yl-ethylamino)-6-(1,2,4,5-tetrahydro-benzo[d]azepin-3-yl)-pyrimidine-5-carbonitrile as a orange amorphous solid; MS: [M+H]$^+$=508.

Preparation of the 4-chloro-2-(2-morpholin-4-yl-ethoxy)-6-(1,2,4,5-tetrahydro-benzo[d]azepin-3-yl)-pyrimidine-5-carbonitrile In analogy to the procedure described in example 47 a) the 4-chloro-2-methanesulfonyl-6-(1,2,4,5-tetrahydro-benzo[d]azepin-3-yl)-pyrimidine-5-carbonitrile (example 171) was treated with 4-(2-hydroxyethyl)-morpholine in tetrahydrofuran in the presence of sodium hydride at 40° C. to yield the 4-chloro-2-(2-morpholin-4-yl-ethoxy)-6-(1,2,4,5-tetrahydro-benzo[d]azepin-3-yl)-pyrimidine-5-carbonitrile as a colorless amorphous solid; MS: [M+H]$^+$=414.

EXAMPLE 189

2-[2-(Pyridin-2-yloxy)-ethylaminol-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3- yl)-6-(2,2,2-trifluoro-ethoxy)-pyrimidine-5-carbonitrile (example 172) was treated with the 2-(pyridin-2-yloxy)-ethylamine in dioxan at 80° C. to yield the 2-[2-(pyridin-2-yloxy)-ethylamino]-4-(1,2,4,5-tetrahydro-benzo[d]azepin-3-yl)-6-(2,2,2-trifluoro-ethoxy)-pyrimidine-5-carbonitrile as amorphous colorless solid; MS: $[M+H]^+$=485.

EXAMPLE 190

2-(2-Hydroxy-ethylamino)-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the ethanolamine in dioxan at 80° C. to yield the 2-(2-hydroxy-ethylamino)-4-(1,2,4,5-tetrahydro-benzo[d]azepin-3-yl)-6-(2,2,2-trifluoro-ethoxy)-pyrimidine-5-carbonitrile as colorless amorphous solid; MS: $[M+H]^+$=408.

EXAMPLE 191

(3-Imidazol-1-yl-propylamino)-4-(1,2,4,5-tetrahydro-benzo[d]azepin-3-yl)-6-(2,2,2-trifluoro-ethoxy)1-pyrimidine-5-carbonitrile In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the 1-(3-aminopropyl)-imidazole in dioxan at 80° C. to yield the (3-imidazol-1-yl-propylamino)-4-(1,2,4,5-tetrahydro-benzo[d]azepin-3-yl)-6-(2,2,2-trifluoro-ethoxy)-pyrimidine-5-carbonitrile as colorless amorphous solid; MS: $[M+H]^+$=472.

EXAMPLE 192

5-Methylsulfanyl-7-(1,2,4,5-tetrahydro-benzo[d]azepin-3-yl)-imidazo[1,2-c]pyrimidine-8-carbonitrile A supension of 0.120 g (0.27 mmol) of the 4-amino-2-methylsulfanyl-6-(1,2,4,5-tetrahydro-benzo[d]azepin-3-yl)-pyrimidine-5-carbonitrile (example 164) in 0.390 ml (2.7 mmol) of chloroacetaldehyde solution (45% in water) was stirred at 80° C. for 2 hours. The reaction mixture was then evaporated under reduced pressure, suspended in an ether and hexane mixture and the not soluble crystals filtered off. The residue obtained was further purified by chromatography on silica gel using a 95:5 v/v mixture of dichloromethane and methanol as eluent to yield 0.065 g (0.194 mmol), 72.3%, of the 5-methylsulfanyl-7-( 1,2,4,5-tetrahydro-benzo[d]azepin-3-yl)-imidazo[1,2-c]pyrimidine-8-carbonitrile as amorphous light brown solid; MS: $[M+H]^+$=336.

EXAMPLE 193

3-[2-Methyl-5-nitro-6-(3-phenyl-propoxy)-pyrimidin-4-yl]-2,3,4,5-tetrahydro-1H-benzo[d]azepine From the 2-methyl-5-nitro-6-(1,2,4,5-tetrahydro-benzo[d]azepin-3-yl)-pyrimidin-4-ol (example 1) with the 3-chloro-1-phenyl-propane in N,N-dimethylformamide in the presence of potassium carbonate at 80° C. as light yellow oil; MS: $[M+H]^+$=419; see example 194.

EXAMPLE 194

2-Methyl-5-nitro-3-(3-phenyl-propyl)-6-(1,2,4,5-tetrahydro-benzo[d]azepin-3-yl)-3H-pyrimidin-4-one In analogy to the procedure described in example 3 the 2-methyl-5-nitro-6-(1,2,4,5-tetrahydro-benzo[d]azepin-3-yl)-pyrimidin-4-ol (example 1) was treated with the 3-chloro-1-phenyl-propane in N,N-dimethylformamide in the presence of potassium carbonate 80° C. to yield the 2-methyl-5-nitro-3-(3-phenyl-propyl)-6-(1,2,4,5-tetrahydro-benzo[d]azepin-3-yl)-3H-pyrimidin-4-one as yellow oil; MS: $[M+H]^+$=419; and the 3-[2-methyl-5-nitro-6-(3-phenyl-propoxy)-pyrimidin-4-yl]-2,3,4,5-tetrahydro-1H-benzo[d]azepine as light yellow oil; MS: $[M+H]^+$=419.

EXAMPLE 195

(2-Pyrrolidin-1-yl-ethylamino)-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the N-(2-aminoethyl)-pyrrolidine in dioxan at 80° C. to yield the (2-pyrrolidin-1-yl-ethylamino)-4-(1,2,4,5-tetrahydro-benzo[d]azepin-3-yl)-6-(2,2,2-trifluoro-ethoxy)-pyrimidine-5-carbonitrile as light yellow amorphous solid; MS: $[M+H]^+$=461.

EXAMPLE 196

2-Methyl-5-nitro-3-(3-pyridin-3-yl-propyl)-6-(1,2,4,5-tetrahydro-benzo[d]azepin-3-yl)-3H-pyrimidin-4-one From the 2-methyl-5-nitro-6-(1,2,4,5-tetrahydro-benzo[d]azepin-3-yl)-pyrimidin-4-ol (example 1) with the toluene-4-sulfonic acid 3-(3-pyridyl)-propyl ester in N,N-dimethylformamide in the presence of potassium carbonate at 120° C. as yellow oil; MS: $[M+H]^+$=420; see example 197.

EXAMPLE 197

3-[2-Methyl-5-nitro-6-(3-pyridin-3-yl-propoxy)-pyrimidin-4-yl]-2,3,4,5-tetrahydro-1H-benzo[d]azepine In analogy to the procedure described in example 3 the 2-methyl-5-nitro-6-(1,2,4,5-tetrahydro-benzo[d]azepin-3-yl)-pyrimidin-4-ol (example 1) was treated with the toluene-4-sulfonic acid 3-(3-pyridyl)-propyl ester in N,N-dimethylformamide in the presence of potassium carbonate at 120° C. to yield the 3-[2-methyl-5-nitro-6-(3-pyridin-3-yl-propoxy)-pyrimidin-4-yl]-2,3,4,5-tetrahydro-1H-benzo[d]azepine as yellow oil; MS: $[M+H]^+$=420; and the 2-methyl-5-nitro-3-(3-pyridin-3-yl-propyl)-6-(1,2,4,5-tetrahydro-benzo[d]azepin-3-yl)-3H-pyrimidin-4-one as yellow oil; MS: $[M+H]^+$=420.

EXAMPLE 198

3-(6-Chloro-2-methyl-5-nitro-pyrimidin-4-yl)-2,3,4,5-tetrahydro-1H-benzo[d]azepine 0.266 g (1.25 mmol) of phosphorus pentachloride were added to a suspension of 0.30 g (1.0 mmol) of the 2-methyl-5-nitro-6-(1,2,4,5-tetrahydro-benzo[d]azepin-3-yl)-pyrimidin-4-ol (example 1) in 0.66 g (5.0 mmol) of N-ethyldiisopropylamine under argon at 0° C. Then, 0.63 g (4.0 mmol) of phosphorus oxychloride were added and the reaction mixture stirred at 100° C. for 3 h. It was then poured into 50 ml of an ice/water mixture and extracted three times with 100 ml of dichloromethane. The combined organic phases were washed twice with 50 ml of water, dried over magnesium sulphate, evaporated under reduced pressure and dried in a high vacuum. The thus obtained crude product was purified by chromatography on silica gel using a 1:1 v/v mixture of hexane and ethyl acetate as eluent to yield 0.161 g (0.505 mmol), 50.5%, of the 3-(6-chloro-2-methyl-5-nitro-pyrimidin-4-yl)-2,3,4,5-tetrahydro-1H-benzo[d]azepine as light brown solid; m.p. 161–165° C.; MS: [M+H]$^+$=319.

EXAMPLE 199

1-Hydroxy-2-methyl-6-oxo-4-(1,2,4,5-tetrahydro-benzo[d]azepin-3-yl)-1,6-dihydro-pyrimidine-5-carbonitrile A suspension of 0.30 g (1.07 mmol) of the 2-methyl-6-oxo-4-(1,2,4,5-tetrahydro-benzo[d]azepin-3-yl)-1,6-dihydro-pyrimidine-5-carbonitrile (example 17) in 10 ml of hexamethyldisilazane and 3.0 ml of trimethylchlorosilane was heated at reflux for 3 hours. The solution formed was then evaporated under reduced pressure. The residue was dissolved in 10 ml of dichloromethane and treated with 0.93 g (2.14 mmol) of the oxodiperoxymolybdenum (pyridine) (HMPA) complex [J. Org. Chem. 43 (1978), 188–196] and the reaction mixture was stirred at room temperature for 20 hours. Then, 0.63 g (2.14 mmol) of ethylenediamine-tetraacetic acid and 8.4 ml of 1N sodium hydroxide solution were added and stirring continued for 30 minutes. The aqueous phase was then adjusted to pH 7 with 1N hydrogen chloride solution, and the reaction mixture extracted three times with 50 ml of dichloromethane. The combined organic phases were washed twice with 50 ml of water, dried over magnesium sulphate, evaporated under reduced pressure and dried in a high vacuum. The thus obtained crude product was crystallized from ether to yield 0.115 g (0.388 mmol), 36.3%, of the 1-hydroxy-2-methyl-6-oxo-4-(1,2,4,5-tetrahydro-benzo[d]azepin-3-yl)-1,6-dihydro-pyrimidine-5-carbonitrile as yellowish solid; m.p. 168.5–172° C.; MS: [M+H]$^+$=297.

EXAMPLE 200

1-Amino-2-methyl-6-oxo-4-(1,2,4,5-tetrahydro-benzo[d]azepin-3-yl)-1,6-dihydro-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with the O-mesitylenesulfonylhydroxylamine [Synthesis 1972, 140] in N,N-dimethylformamide in the presence of potassium carbonate at room temperature to yield the 1-amino-2-methyl-6-oxo-4-(1,2,4,5-tetrahydro-benzo[d]azepin-3-yl)-1,6-dihydro-pyrimidine-5-carbonitrile as colorless solid; m.p. 137–142° C.; MS: [M+H]$^+$=296.

EXAMPLE 201

2-(4-Ethyl-piperazin-1-yl)-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the ethyl-piperazine in dioxan at 80° C. to yield the 2-(4-ethyl-piperazin-1-yl)-4-(1,2,4,5-tetrahydro-benzo[d]azepin-3-yl)-6-(2,2,2-trifluoro-ethoxy)-pyrimidine-5-carbonitrile as light yellow amorphous solid; MS: [M+H]$^+$=461.

EXAMPLE 202

3-(3-Imidazol-1-yl-propyl)-2-methyl-5-nitro-6-(1,2,4,5-tetrahydro-benzo[d]azepin-3-yl)-3H-pyrimidin-4-one A solution of 0.437 g (1.0 mmol) of the methanesulfonic acid 3-[2-methyl-5-nitro-6-oxo-4-(1,2,4,5-tetrahydro-benzo[d]azepin-3-yl)-6H-pyrimidin-1-yl]-propyl ester [prepared from the 3-(3-hydroxy-propyl)-2-methyl-5-nitro-6-(1,2,4,5-tetrahydro-benzo[d]azepin-3-yl)-3H-pyrimidin-4-one (example 186) and methanesulfonyl chloride/triethylamine in dichloromethane, −70° C. to room temperature], 0.103 g (1.5 mmol) of imidiazole and 0.396 g (3.0 mmol) of N-ethyl-diisopropylamine in 10.0 ml N,N-dimethylformamide was stirred at 80° C. for 16 hours. The reaction mixture was then poured into 50 ml of an ice/water mixture and extracted three times with 60 ml of dichloromethane. The combined organic phases were washed twice with 50 ml of water, dried over magnesium sulphate, evaporated under reduced pressure and dried in a high vacuum. The thus obtained crude product was purified by chromatography on silica gel using a 10:0 to 9:1 v/v mixture of dichloromethane and methanol as eluent to yield 0.134 g (0.328 mmol), 33%, 3-(3-imidazol-1-yl-propyl)-2-methyl-5-nitro-6-(1,2,4,5-tetrahydro-benzo[d]azepin-3-yl)-3H-pyrimidin-4-one as light yellow oil; MS: [M−H]$^-$=407.

EXAMPLE 203

2-Methyl-3-(3-morpholin-4-yl-propyl)-5-nitro-6-(1,2,4,5-tetrahydro-benzo[d]azepin-3-yl)-3H-pyrimidin-4-one In analogy to the procedure described in example 202 the methanesulfonic acid 3-[2-methyl-5-nitro-6-oxo-4-(1,2,4,5-tetrahydro-benzo[d]azepin-3-yl)-6H-pyrimidin-1-yl]-propyl ester (example 202) was treated with the morpholine (excess) at room temperature to yield the 2-methyl-3-(3-morpholin-4-yl-propyl)-5-nitro-6-(1,2,4,5-tetrahydro-benzo[d]azepin-3 -yl)-3H-pyrimidin-4-one as light yellow amorphous solid; MS: [M+H]$^+$=428.

EXAMPLE 204

2-Methyl-5-nitro-6-(1,2,4,5-tetrahydro-benzo[d]azepin-3-yl)-3-(3-[1,2,4,]triazol-1-yl-propyl)-3H-pyrimidin-4-one In analogy to the procedure described in example 202 the methanesulfonic acid 3-[2-methyl-5-nitro-6-oxo-4-(1,2,4,5-tetrahydro-benzo[d]azepin-3-yl)-6H-pyrimidin-1-yl]-propyl ester (example 202) was treated with the 1,2,4-triazole and sodium hydride in N,N-dimethylformamide at room temperature to yield the 2-methyl-5-nitro-6-(1,2,4,5-tetrahydro-benzo[d]azepin-3-yl)-3-(3-1,2,4]triazol-1-yl-propyl)-3H-pyrimidin-4-one as light yellow amorphous solid; MS: [M+H]$^+$=410.

EXAMPLE 205

3-[3-(2-(R)-Hydroxymethyl-pyrrolidin-1-yl)-propyl]-2-methyl-5-nitro-6-(1,2,4,5-tetrahydro-benzo[d]azepin-3-yl)-3H-pyrimidin-4-one In analogy to the procedure described in example 202 the methanesulfonic acid 3-[2-methyl-5-nitro-6-oxo-4-(1,2,4,5-tetrahydro-benzo[d]azepin-3-yl)-6H-pyrimidin-1-yl]-propyl ester (example 202) was treated with the (R)-(−)-2-hydroxymethyl-pyrrolidine and N-ethyl-diisopropylamine in tetrahydrofuran at reflux to yield the 3-[3-(2-(R)-hydroxymethyl-pyrrolidin-1-yl)-propyl]-2-methyl-5-nitro-6-(1,2,4,5-tetrahydro-benzo[d]azepin-3-yl)-3H-pyrimidin-4-one as light yellow oil; MS: [M+H]$^+$=442.

EXAMPLE 206

3-[2-Methyl-5-nitro-6-(3-[1,2,4]triazol-1-yl-propoxy)-pyrimidin-4-yl]-2,3,4,5-tetrahydro-1H-benzo[d]azepine In analogy to the procedure described in example 202 the methanesulfonic acid 3-[2-methyl-5-nitro-6-(1,2,4,5-tetrahydro-benzo[d]azepin-3-yl)-pyrimidin-4-yloxy]-propyl ester [prepared from 3-[2-methyl-5-nitro-6-(1,2,4,5-tetrahydro-benzo[d]azepin-3-yl)-pyrimidin-4-yloxy]-propan-1-ol (example 187) and methanesulfonyl chloride/triethylamine in dichloromethane, −70° C. to room temperature] was treated with the 1,2,4-triazole and N-ethyl-diisopropylamine in N,N-dimethylformamide at 50° C. to yield the 3-[2-methyl-5-nitro-6-(3-[1,2,4]triazol-1-yl-propoxy)-pyrimidin-4-yl]-2,3,4,5-tetrahydro-1H-benzo[d]azepine as light yellow oil; MS: [M−H]$^-$=408.

EXAMPLE 207

3-(6-(3-Imidazol-1-yl-propoxy)-2-methyl-5-nitro-pyrimidin-4-yl]-2,3,4,5-tetrahydro-1H-benzo[d]azepine In analogy to the procedure described in example 202 the methanesulfonic acid 3-[2-methyl-5-nitro-6-(1,2,4,5-tetrahydro-benzo[d]azepin-3-yl)-pyrimidin-4-yloxy]-propyl ester (example 206) was treated with the imidazole and N-ethyl-diisopropylamine in N,N-dimethylformamide at 50° C. to yield the 3-[6-(3-imidazol-1-yl-propoxy)-2-methyl-5-nitro-pyrimidin-4-yl]-2,3,4,5-tetrahydro-1H-benzo[d]azepine as light yellow amorphous solid; MS: [M+H]$^+$=409.

EXAMPLE 208

3-[2-Methyl-5-nitro-6-(3-pyridin-2-yl-propoxy)-pyrimidin-4-yl]-2,3,4,5-tetrahydro-1H-benzo[d]azepine In analogy to the procedure described in example 47 a) the 3-(6-chloro-2-methyl-5-nitro-pyrimidin-4-yl)-2,3,4,5-tetrahydro-1H-benzo[d]azepine (example 198) was treated with the 3-pyridin-2-yl-propanol in N,N-dimethylformamide in the presence of sodium hydride at 50° C. to yield the 3-[2-methyl-5-nitro-6-(3-pyridin-2-yl-propoxy)-pyrimidin-4-yl]-2,3,4,5-tetrahydro-1H-benzo[d]azepine as light brown oil; MS: [M+H]$^+$=420.

EXAMPLE 209

3-[2-Methyl-5-nitro-6-(3-pyridin-4-yl-propoxy)-pyrimidin-4-yl]-2,3,4,5-tetrahydro-1H-benzo[d]azepine In analogy to the procedure described in example 47 a) the 3-(6-chloro-2-methyl-5-nitro-pyrimidin-4-yl)-2,3,4,5-tetrahydro-1H-benzo[d]azepine (example 198) was treated with the 3-pyridin-4-yl-propanol in N,N-dimethylformamide in the presence of sodium hydride at room temperature to yield the 3-[2-methyl-5-nitro-6-(3-pyridin-4-yl-propoxy)-pyrimidin-4-yl]-2,3,4,5-tetrahydro-1H-benzo[d]azepine as light brown oil; MS: [M+H]$^+$=420.

EXAMPLE 210

[2-Methyl-5-nitro-6-(1,2,4,5-tetrahydro-benzo[d]azepin-3-yl)-pyrimidin-4-yl]-(3-morpholin-4-yl-propyl)-amine In analogy to the procedure described in example 48 the 3-(6-chloro-2-methyl-5-nitro-pyrimidin-4-yl)-2,3,4,5-tetrahydro-1H-benzo[d]azepine (example 198) was treated with the 4-(3-aminopropyl)-morpholine (excess) at room temperature to yield the [2-methyl-5-nitro-6-(1,2,4,5-tetrahydro-benzo[d]azepin-3-yl)-pyrimidin-4-yl]-(3-morpholin-4-yl-propyl)-amine as yellow oil; MS: [M+H]$^+$=427.

EXAMPLE 211

(3-Imidazol-1-yl-propyl)-[2-methyl-5-nitro-6-(1,2,4,5-tetrahydro-benzo[d]azepin-3-yl)-pyrimidin-4-yl]-amine In analogy to the procedure described in example 48 the 3-(6-chloro-2-methyl-5-nitro-pyrimidin-4-yl)-2,3,4,5-tetrahydro-1H-benzo[d]azepine (example 198) was treated with the 1-(3-aminopropyl)-imidazole (excess) at room temperature to yield the (3-imidazol-1-yl-propyl)-[2-methyl-5-nitro-6-(1,2,4,5-tetrahydro-benzo[d]azepin-3-yl)-pyrimidin-4-yl]-amine as yellow oil; MS: [M+H]$^+$=408.

EXAMPLE 212

4-[2-Methyl-5-nitro-6-(1,2,4,5-tetrahydro-benzo[d]azepin-3-yl)-pyrimidin-4-ylamino]-butan-1-ol In analogy to the procedure described in example 48 the 3-(6-chloro-2-methyl-5-nitro-pyrimidin-4-yl)-2,3,4,5-tetrahydro-1H-benzo[d]azepine (example 198) was treated with the 4-amino-1-butanol (excess) at room temperature to yield the 4-[2-methyl-5-nitro-6-(1,2,4,5-tetrahydro-benzo[d]azepin-3-yl)-pyrimidin-4-ylamino]-butan-1-ol as light yellow oil; MS: [M−H]$^-$=370.

EXAMPLE 213

3-[2-Methyl-5-nitro-6-(1,2,4,5-tetrahydro-benzo[d]azepin-3-yl)-pyrimidin-4-ylamino]-propan-1-ol In analogy to the procedure described in example 48 the 3-(6-chloro-2-methyl-5-nitro-pyrimidin-4-yl)-2,3,4,5-tetrahydro-1H-benzo[d]azepine (example 198) was treated with the 3-amino-1-propanol (excess) at room temperature to yield the 3-[2-methyl-5-nitro-6-(1,2,4,5-tetrahydro-benzo[d]azepin-3-yl)-pyrimidin-4-ylamino]-propan-1-ol as light yellow solid; m.p. 104–108° C.; MS: [M−H]$^-$=356.

EXAMPLE 214

2-Methyl-1-methylamino-6-oxo-4-(1,2,4,5-tetrahydro-benzo[d]azepin-3-yl)-1,6-dihydro-pyrimidine-5-carbonitrile From the 1-amino-2-methyl-6-oxo-4-(1,2,4,5-tetrahydro-benzo[d]azepin-3-yl)-1,6-dihydro-pyrimidine-5-carbonitrile (example 200) and methyl iodide, potassium carbonate in N,N-dimethylformamide as colorless solid; m.p. >200° C.; MS: [M+H]$^+$=310; see example 215.

EXAMPLE 215

[5-Cyano-2-methyl-6-oxo-4-(1,2,4,5-tetrahydro-benzo[d]azepin-3-yl)-6H-pyrimidin-1-yl]-methyl-carbamic acid methyl ester A solution of 0.110 g (0.37 mmol) of the 1-amino-2-methyl-6-oxo-4-(1,2,4,5-tetrahydro-benzo[d]azepin-3-yl)-1,6-dihydro-pyrimidine-5-carbonitrile (example 200), 0.112 ml (4.8 mmol) of methyl iodide and 0.162 g (1.17 mmol) of potassium carbonate in 1.0 ml of N,N-dimethylformamide was stirred at room temperature for 60 hours. The reaction mixture was then poured into 25 ml of an ice/water mixture and extracted three times with 50 ml of ethyl acetate. The combined organic phases were washed twice with 50 ml of water, dried over magnesium sulphate, evaporated under reduced pressure and dried in a high vacuum. The thus obtained crude product was purified by chromatography on silica gel using a 1:1 v/v mixture of hexane and ethyl acetate as eluent to yield 0.034 g (0.094 mmol), 25%, of the [5-cyano-2-methyl-6-oxo-4-(1,2,4,5-tetrahydro-benzo[d] azepin-3-yl)-6H-pyrimidin-1-yl]-methyl-carbamic acid methyl ester as colorless solid; m.p. 120–122.5° C.; MS: [M+H]$^+$=368; and 0.008 g (0.026 mmol), 7%, of the 2-methyl-1-methylamino-6-oxo-4-(1,2,4,5-tetrahydro-benzo[d]azepin-3-yl)-1,6-dihydro-pyrimidine-5-carbonitrile as colorless solid; m.p. >200° C.; MS: [M+H]$^+$=310.

EXAMPLE 216

[5-Cyano-2-methyl-6-oxo-4-(1,2,4,5-tetrahydro-benzo[d]azepin-3-yl)-6H-pyrimidin-1-yl]-ethyl-carbamic acid ethyl ester In analogy to the procedure described in example 215 the 1-amino-2-methyl-6-oxo-4-(1,2,4,5-tetrahydro-benzo[d] azepin-3-yl)-1,6-dihydro-pyrimidine-5-carbonitrile (example 200) was treated with the iodoethane in N,N-dimethylformamide in the presence of potassium carbonate at room temperature to yield the [5-cyano-2-methyl-6-oxo-4-(1,2,4,5-tetrahydro-benzo[d]azepin-3-yl)-6H-pyrimidin-1-yl]-ethyl-carbamic acid ethyl ester as colorless amorphous solid; MS: [M+H]$^+$=396.

EXAMPLE 217

[5-Cyano-2-methyl-6-oxo-4-(1,2,4,5-tetrahydro-benzo[d]azepin-3-yl)-6H-pyrimidin-1-yl]-dicarbamic acid tert-butylester 4.2 mg (0.034 mmol) of 4-dimethylamino pyridine were added to a solution of 0.100 g (0.34 mmol) of the 1-amino-2-methyl-6-oxo-4-(1,2,4,5-tetrahydro-benzo[d]azepin-3-yl)-1,6-dihydro-pyrimidine-5-carbonitrile (example 200) and 0.141 mg (0.65 mmol) of di-tert-butyldicarbonate in 1.5 ml of dichloromethane and the reaction mixture was stirred at room temperature for 16 hours. It was then evaporated under reduced pressure and dried in a high vacuum. The thus obtained crude product was purified by chromatography on silica gel using a 9:1 v/v mixture of dichloromethane and diethyl ether as eluent to yield 0.074 g (0.015 mmol), 44%, of the [5-cyano-2-methyl-6-oxo-4-(1,2,4,5-tetrahydro-benzo[d]azepin-3-yl)-6-H-pyrimidin-1-yl]-dicarbamic acid tert-butylester as colorless solid; m.p. 148–150° C.; MS: [M+H]$^+$=496.

EXAMPLE 218

[5-Cyano-2-methyl-6-oxo-4-(1,2,4,5-tetrahydro-benzo[d]azepin-3-yl)-6H-pyrimidin-1-yl]-carbamic acid tert-butyl ester 670 mg (1.35 mmol) of the [5-cyano-2-methyl-6-oxo-4-(1,2,4,5-tetrahydro-benzo[d]azepin-3-yl)-6H-pyrimidin-1-yl]-dicarbamic acid tert-butylester (example 217) and 3.5 g silica gel were suspended in 10 ml of dichloromethane and slurry stirred for 16 hours. It was then transferred on a silica gel chromatography column and the desired product eluted with a 9:1 v/v mixture of dichloromethane and diethyl ether yielding 0.395 g (1.0 mmol), 74%, of the [5-cyano-2-methyl-6-oxo-4-(1,2,4,5-tetrahydro-benzo[d]azepin-3-yl)-6H-pyrimidin-1-yl]-carbamic acid tert-butyl ester as colorless solid; m.p. 150–152° C.; MS: [M+H]$^+$=396.

EXAMPLE 219

2-(2-Pyridin-3-yl-ethylamino)-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the 2-pyridin-3-yl-ethylamine in dioxan at 80° C. to yield the 2-(2-pyridin-3-yl-ethylamino)-4-(1,2,4,5-tetrahydro-benzo[d]azepin-3-yl)-6-(2,2,2-trifluoro-ethoxy)-pyrimidine-5-carbonitrile as light yellow amorphous solid; MS: [M+H]$^+$=469.

EXAMPLE 220

2-Methyl-6-oxo-4-(1,2,4,5-tetrahydro-benzo[d]azepin-3-yl)-1-(2,2,2-trifluoro-ethoxy)-1,6-dihydro-pyrimidine-5-carbonitrile In analogy to the procedure described in example 3 the 1-hydroxy-2-methyl-6-oxo-4-(1,2,4,5-tetrahydro-benzo[d] azepin-3-yl)-1,6-dihydro-pyrimidine-5-carbonitrile (example 199) was treated with the 2,2,2-trifluoroethyl trifluoromethanesulfonate in N,N-dimethylformamide in the presence of potassium carbonate to yield the 2-methyl-6-oxo-4-(1,2,4,5-tetrahydro-benzo[d]azepin-3-yl)-1-(2,2,2-trifluoro-ethoxy)-1,6-dihydro-pyrimidine-5-carbonitrile as colorless solid; m.p. >200° C.; MS: [M+H]$^+$=379.

EXAMPLE 221

1-{3-[2-Methyl-5-nitro-6-(1,2,4,5-tetrahydro-benzo[d]azepin-3-yl)- pyrimidin-4-ylamino]-propyl}-pyrrolidin-2-one In analogy to the procedure described in example 48 the 3-(6-chloro-2-methyl-5-nitro-pyrimidin-4-yl)-2,3,4,5-tetrahydro-1H-benzo[d]azepine (example 198) was treated with the 1-(3-aminopropyl)-2-pyrrolidinone in tetrahydrofuran at room temperature to yield the 1-{3-[2-methyl-5-nitro-6-(1,2,4,5-tetrahydro-benzo[d]azepin-3-yl)-pyrimidin-4-ylamino]-propyl}-pyrrolidin-2-one as light yellow oil; MS: [M+H]$^+$=425.

EXAMPLE 222

3-[3-(3-(R)-Hydroxy-pyrrolidin-1-yl)-propyl]-2-methyl-5-nitro-6-(1,2,4,5-tetrahydro-benzo[d]azepin-3-yl)-3H-pyrimidin-4-one In analogy to the procedure described in example 202 the methanesulfonic acid 3-[2-methyl-5-nitro-6-oxo-4-(1,2,4,5-tetrahydro-benzo[d]azepin-3-yl)-6H-pyrimidin-1-yl]-propyl ester (example 202) was treated with the (R)-3-hydroxypyrrolidine and N-ethyldiisopropyl amine in tetrahydrofuran between room temperature and reflux to yield the 3-[3-(3-(R)-hydroxy-pyrrolidin-1-yl)-propyl]-2-methyl-5-nitro-6-(1,2,4,5-tetrahydro-benzo[d]azepin-3-yl)-3H-pyrimidin-4-one as light yellow oil; MS: [M+H]$^+$=428.

EXAMPLE 223

N'-[5-Cyano-2-methyl-6-oxo-4-(1,2,4,5-tetrahydro-benzo[d]azepin-3-yl)-6H-pyrimidin-1-yl]-hydrazinecarboxylic acid tert-butyl ester In analogy to the procedure described in example 3 the 2-methyl-6-oxo-4-(1,2,4,5-tetrahydro-benzo[d]azepin-3- yl)-1,6-dihydro-pyrimidine-5-carbonitrile (example 17) was treated with a mixture of the O-mesitylenesulfonylhydroxylamine [Synthesis 1972, 140] and the t-butyl N-mesitylenesulfonyloxycarbamate [Synthesis 1972, 140] in N,N-dimethylformamide in the presence of potassium carbonate at room temperature to yield beside the 1-amino-2-methyl-6-oxo-4-(1,2,4,5-tetrahydro-benzo[d]azepin-3-yl)-1,6-dihydro-pyrimidine-5-carbonitrile (example 200) the N'-[5-cyano-2-methyl-6-oxo-4-(1,2,4,5-tetrahydro-benzo[d]azepin-3-yl)-6H-pyrimidin-1-yl]-hydrazinecarboxylic acid tert-butyl ester as colorless solid; m.p. 170–171.5° C.; MS: [M+H]$^+$=411.

EXAMPLE 224

1-Methoxy-2-methyl-6-oxo-4-(1,2,4,5-tetrahydro-benzo[d]azepin-3-yl)-1,6-dihydro-pyrimidine-5-carbonitrile In analogy to the procedure described in example 3 the 1-hydroxy-2-methyl-6-oxo-4-(1,2,4,5-tetrahydro-benzo[d]azepin-3-yl)-1,6-dihydro-pyrimidine-5-carbonitrile (example 199) was treated with the methyl iodide in N,N-dimethylformamide in the presence of potassium carbonate to yield the 1-methoxy-2-methyl-6-oxo-4-(1,2,4,5-tetrahydro-benzo[d]azepin-3-yl)-1,6-dihydro-pyrimidine-5-carbonitrile as colorless solid; m.p. 144–145° C.; MS: [M]$^+$=310.

EXAMPLE 225

1-Ethoxy-2-methyl-6-oxo-4-(1,2,4,5-tetrahydro-benzo[d]azepin-3-yl)-1,6-dihydro-pyrimidine-5-carbonitrile In analogy to the procedure described in example 3 the 1-hydroxy-2-methyl-6-oxo-4-(1,2,4,5-tetrahydro-benzo[d]azepin-3-yl)-1,6-dihydro-pyrimidine-5-carbonitrile (example 199) was treated with the ethyl iodide in N,N-dimethylformamide in the presence of potassium carbonate at room temperature to yield the 1-ethoxy-2-methyl-6-oxo-4-(1,2,4,5-tetrahydro-benzo[d]azepin-3-yl)-1,6-dihydro-pyrimidine-5-carbonitrile as colorless solid; m.p. 149–152° C.; MS: [M]$^+$=324.

EXAMPLE 226

2-Methyl-6-oxo-1-propoxy-4-(1,2,4,5-tetrahydro-benzo[d]azepin-3-yl)-1,6-dihydro-pyrimidine-5-carbonitrile In analogy to the procedure described in example 3 the 1-hydroxy-2-methyl-6-oxo-4-(1,2,4,5-tetrahydro-benzo[d]azepin-3-yl)-1,6-dihydro-pyrimidine-5-carbonitrile (example 199) was treated with n-propyl iodide in N,N-dimethylformamide in the presence of potassium carbonate at room temperature to yield the 2-methyl-6-oxo-1-propoxy-4-(1,2,4,5-tetrahydro-benzo[d]azepin-3-yl)-1,6-dihydro-pyrimidine-5-carbonitrile as colorless solid; m.p. 132.5–134° C.; MS: [M]$^+$=338.

EXAMPLE 227

4-Methoxy-2-methyl-6-(1,2,4,5-tetrahydro-benzo[d]azepin-3-yl)-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with methyl iodide in N,N-dimethylformamide in the presence of potassium carbonate to yield the beside the 1,2-dimethyl-6-oxo-4-(1,2,4,5-tetrahydro-benzo[d]azepin-3-yl)-1,6-dihydro-pyrimidine-5-carbonitrile (example 26) the 4-methoxy-2-methyl-6-(1,2,4,5-tetrahydro-benzo[d]azepin-3-yl)-pyrimidine-5-carbonitrile as colorless amorphous solid; MS: [M]$^+$=294.

EXAMPLE 228

2-Methyl-4-propoxy-6-(1 2,4,5-tetrahydro-benzo[d]azepin-3-yl)-pyrimidine-5-carbonitrile From the 2-methyl-6-oxo-4-(1,2,4,5-tetrahydro-benzo[d]azepin-3-yl)-1,6-dihydro-pyrimidine-5-carbonitrile (example 17) with n-propyl iodide in N,N-dimethylformamide in the presence of potassium carbonate as colorless amorphous solid; MS: [M+H]$^+$=323; see example 229.

EXAMPLE 229

2-Methyl-6-oxo-1-propyl-4-(1,2,4,5-tetrahydro-benzo[d]azepin-3-yl)-1,6-dihydro-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with n-propyl iodide in N,N-dimethylformamide in the presence of potassium carbonate to yield the 2-methyl-6-oxo-1-propyl-4-(1,2,4,5-tetrahydro-benzo[d]azepin-3-yl)-1,6-dihydro-pyrimidine-5-carbonitrile as colorless amorphous solid; MS: [M+H]$^+$=323; and the 2-methyl-4-propoxy-6-(1,2,4,5-tetrahydro-benzo[d]azepin-3-yl)-pyrimidine-5-carbonitrile as colorless amorphous solid; MS: [M+H]$^+$=323.

EXAMPLE 230

(1,2-Diamino-6-oxo-4-(1,2,4,5-tetrahydro-benzo[d]azepin-3-yl)-1,6-dihydro-pyrimidine-5-carbonitrile In analogy to the procedure described in example 3 the 2-amino-6-oxo-4-(1,2,4,5-tetrahydro-benzo[d]azepin-3-yl)-1,6-dihydro-pyrimidine-5-carbonitrile (example 13) was treated with the O-mesitylenesulfonylhydroxylamine [Synthesis 1972, 140] in N,N-dimethylformamide in the presence of potassium carbonate at room temperature to yield the (1,2-diamino-6-oxo-4-(1,2,4,5-tetrahydro-benzo[d]azepin-3-yl)-1,6-dihydro-pyrimidine-5-carbonitrile as colorless solid; m.p. >200° C.; MS: [M+H]$^+$=297.

EXAMPLE 231

3-{6-[4-(tert-Butyl-dimethyl-silanyloxy)-butoxy]-2-methyl-5-nitro-pyrimidin-4-yl}-2,3,4,5-tetrahydro-1H-benzo[d]azepine From the 2-methyl-5-nitro-6-(1,2,4,5-tetrahydro-benzo[d]azepin-3-yl)-pyrimidin-4-ol (example 1) and the tert.-butyl(4-chlorobutoxy)dimethylsilane in N,N-dimethylformamide in the presence of potassium carbonate at 120° C. as light yellow oil; MS: [M–C$_4$H$_9$]$^+$=429; see example 232.

EXAMPLE 232

3-[4-(tert-Butyl-dimethyl-silanyloxy)-butyl]-2-methyl-5-nitro-6-(1,2,4,5-tetrahydro-benzo[d]azepin-3-yl)-3H-pyrimidin-4-one In analogy to the procedure described in example 3 the 2-methyl-5-nitro-6-(1,2,4,5-tetrahydro-benzo[d]azepin-3- yl)-pyrimidin-4-ol (example 1) was treated with the tert.-butyl(4-chlorobutoxy)dimethylsilane in N,N-dimethylformamide in the presence of potassium carbonate at 120° C. to yield the 3-[4-(tert-butyl-dimethyl-silanyloxy)-butyl]-2-methyl-5-nitro-6-(1,2,4,5-tetrahydro-benzo[d] azepin-3-yl)-3H-pyrimidin-4-one as light yellow oil; MS: [M−C$_4$H$_9$]$^+$=429; and the 3-{6-[4-(tert-butyl-dimethyl-silanyloxy)-butoxy]-2-methyl-5-nitro-pyrimidin-4-yl}-2,3,4,5-tetrahydro-1H-benzo[d]azepine as light yellow oil; MS: [M−C$_4$H$_9$]$^+$=429.

EXAMPLE 233

4-[2-Methyl-5-nitro-6-(1,2,4,5-tetrahydro-benzo[d] azepin-3-yl)-pyrimidin-4-yloxy]-butan-1-ol A solution of 4.01 g (8.23 mmol) of the 3-{6-[4-(tert-butyl-dimethyl-silanyloxy)-butoxy]-2-methyl-5-nitro-pyrimidin-4-yl}-2,3,4,5-tetrahydro-1H-benzo[d]azepine (example 231) in 45 ml of a 2:1 v/v mixture of acetonitrile and dichloromethane was treated with stirring with 5.2 ml of hydrogen fluoride solution (40% in water) and the reaction mixture was stirred at room temperature for 1 hour. It was then poured into 150 ml of an ice/water mixture and extracted three times with 150 ml of dichloromethane. The combined organic phases were washed twice with 50 ml of water, dried over magnesium sulphate, evaporated under reduced pressure and dried in a high vacuum. The thus obtained crude product was purified by chromatography on silica gel using a 9:1 to 1:1 v/v mixture of hexane and ethyl acetate as eluent to yield 2.18 g (5.85 mmol), 71%, of the 4-[2-methyl-5-nitro-6-(1,2,4,5-tetrahydro-benzo[d]azepin-3-yl)-pyrimidin-4-yloxy]-butan-1-ol as yellow oil; MS: [M+H]$^+$=373.

EXAMPLE 234

3-(4-Hydroxy-butyl)-2-methyl-5-nitro-6-(1,2,4,5-tetrahydro-benzo[d]azepin-3-yl)-3H-pyrimidin-4-one In analogy to the procedure described in example 233 the 3-[4-(tert-butyl-dimethyl-silanyloxy)-butyl]-2-methyl-5-nitro-6-(1,2,4,5-tetrahydro-benzo[d]azepin-3-yl)-3H-pyrimidin-4-one (example 232) was treated with a hydrogen fluoride solution (40% in water) in a 2:1 v/v mixture of acetonitrile and dichloromethane at room temperature to yield the 3-(4-hydroxy-butyl)-2-methyl-5-nitro-6-(1,2,4,5-tetrahydro-benzo[d]azepin-3-yl)-3H-pyrimidin-4-one as yellow oil; [M+H]$^+$=373.

EXAMPLE 235

Methanesulfonic acid 4-[2-methyl-5-nitro-6-(1,2,4,5-tetrahydro-benzo[d]azepin-3-yl)-pyrimidin-4-yloxy]-butyl ester Treatment of the 4-[2-methyl-5-nitro-6-(1,2,4,5-tetrahydro-benzo[d]azepin-3-yl)-pyrimidin-4-yloxy]-butan-1-ol (example 233) with methanesulfonyl chloride in dichloromethane (−70° C. to room temperature) gave the methanesulfonic acid 4-[2-methyl-5-nitro-6-(1,2,4,5-tetrahydro-benzo[d]azepin-3-yl)-pyrimidin-4-yloxy]-butyl ester as yellow amorphous solid; [M+H]$^+$=451.

EXAMPLE 236

Methanesulfonic acid 4-[2-methyl-5-nitro-6-oxo-4-(1,2,4,5-tetrahydro-benzo[d]azepin-3-yl)-6H-pyrimidin-1-yl]-butyl ester Treatment of the 3-(4-hydroxy-butyl)-2-methyl-5-nitro-6-(1,2,4,5-tetrahydro-benzo[d]azepin-3-yl)-3H-pyrimidin-4-one (example 234) with methanesulfonyl chloride in dichloromethane (−70° C. to room temperature) gave the methanesulfonic acid 4-[2-methyl-5-nitro-6-oxo-4-(1,2,4,5-tetrahydro-benzo[d]azepin-3-yl)-6H-pyrimidin-1-yl]-butyl ester as yellow amorphous solid; [M+H]$^+$=451.

EXAMPLE 237

3-[3-Nitro-2-(1,2,4,5-tetrahydro-benzo[d]azepin-3-yl)-6,7,8,9-tetrahydro-5-H-cyclohepta[b]pyridin-4-ylaminol -propan-1-ol In analogy to the procedure described in example 4 the trifluoro-methanesulfonic acid 4-(3-hydroxy-propylamino)-3-nitro-6,7,8,9-tetrahydro-5H-cyclohepta[b]pyridin-2-yl ester was treated with the 2,3,4,5-tetrahydro-1H-benzo[d]azepine hydrochloride [J. Heterocycl. Chem. (1971), 8(5), 779–83] in N,N-dimethylformamide in the presence of N-ethyl-N,N-diisopropylamine at room temperature to yield the 3-[3-nitro-2-(1,2,4,5-tetrahydro-benzo[d]azepin-3-yl)-6,7,8,9-tetrahydro-5H -cyclohepta[b]pyridin-4-ylamino]-propan-1-ol yellow oil; MS: [M+H]$^+$=411.

Preparation of the trifluoro-methanesulfonic acid 4-(3-hydroxy-propylamino)-3-nitro-6,7,8,9-tetrahydro-5H-cyclohepta[b]pyridin-2-yl ester The trifluoro-methanesulfonic acid 4-(3-hydroxy-propylamino)-3-nitro-6,7,8,9-tetrahydro-5H-cyclohepta[b]pyridin-2-yl ester used above was prepared by the following reaction sequence: i) treatment of the 3-nitro-6,7,8,9-tetrahydro-5H-cyclohepta[b]pyridine-2,4-diol [U.S. Pat. No. 5,352,784 A (1994)] with trifluoromethanesulfonic anhydride and triethylamine in dichloromethane at 3° C. gave the trifluoro-methanesulfonic acid 3-nitro-2-trifluoromethanesulfonyloxy-6,7,8,9-tetrahydro-5H-cyclohepta[b]pyridin-4-yl ester; ii) treatment of the trifluoro-methanesulfonic acid 3-nitro-2-trifluoromethanesulfonyloxy-6,7,8,9-tetrahydro-5H-cyclohepta[b]pyridin-4-yl ester with 3-amino-1-propanol and triethylamine in dichloromethane at room temperature yielded the trifluoro-methanesulfonic acid 4-(3-hydroxy-propylamino)-3-nitro-6,7,8,9-tetrahydro-5H-cyclohepta[b]pyridin-2-yl ester.

EXAMPLE 238

3-Nitro-2-(1,2,4,5-tetrahydro-benzo[d]azepin-3-yl)-6,7,8,9-tetrahydro-5H-cyclohepta[b]pyridin-4-ol In analogy to the procedure described in example 4 the trifluoro-methanesulfonic acid 4-hydroxy-3-nitro-6,7,8,9-tetrahydro-5H-cyclohepta[b]pyridin-2-yl ester [prepared from the trifluoro-methanesulfonic acid 3-nitro-2-trifluoromethanesulfonyloxy-6,7,8,9-tetrahydro-5H-cyclohepta[b]pyridin-4-yl ester (example 237) and potassium carbonate in a mixture of tetrahydrofuran and water at room temperature] was treated with the 2,3,4,5-tetrahydro-1H-benzo[d]azepine hydrochloride [J. Heterocycl. Chem. (1971), 8(5), 779–83] in N,N-dimethylformamide in the presence of N-ethyl-N,N-diisopropylamine at 50° C. to yield the 3-nitro-2-(1,2,4,5-tetrahydro-benzo[d]azepin-3-yl)-6,7,8,9-tetrahydro-5H-cyclohepta[b]pyridin-4-ol as light yellow solid; m.p. >200° C.; MS: [M+H]$^+$=354.

EXAMPLE 239

[5-Cyano-2-methyl-6-oxo-4-(1,2,4,5-tetrahydro-benzo[d]azepin-3-yl)-6H-pyrimidin-1-yl]-methyl-carbamic acid tert-butyl ester In analogy to the procedure described in example 3 the [5-cyano-2-methyl-6-oxo-4-(1,2,4,5-tetrahydro-benzo[d]

azepin-3-yl)-6H-pyrimidin-1-yl]-carbamic acid tert-butyl ester (example 218) was treated with methyl iodide in N,N-dimethylformamide in the presence of potassium carbonate at room temperature to yield the [5-cyano-2-methyl-6-oxo-4-(1,2,4,5-tetrahydro-benzo[d]azepin-3-yl)-6H-pyrimidin-1-yl]-methyl-carbamic acid tert-butyl ester as colorless solid; m.p. 164–166° C.; MS: [M+H]$^+$=410.

EXAMPLE 240

[5-Cyano-2-methyl-6-oxo-4-(1,2,4,5-tetrahydro-benzo[d]azepin-3-yl)-6H-pyrimidin-1-yl]-ethyl-carbamic acid tert-butyl ester In analogy to the procedure described in example 3 the [5-cyano-2-methyl-6-oxo-4-(1,2,4,5-tetrahydro-benzo[d]azepin-3-yl)-6H-pyrimidin-1-yl]-carbamic acid tert-butyl ester (example 218) was treated with ethyl iodide in N,N-dimethylformamide in the presence of potassium carbonate at room temperature to yield the [5-cyano-2-methyl-6-oxo-4-(1,2,4,5-tetrahydro-benzo[d]azepin-3-yl)-6H-pyrimidin-1-yl]-ethyl-carbamic acid tert-butyl ester as colorless solid; m.p. 86–88° C.; MS: [M+H]$^+$=424.

EXAMPLE 241

5-Cyano-2-methyl-6-oxo-4-(1,2,4,5-tetrahydro-benzo[d]azepin-3-yl)-6H-pyrimidin-1-yl]-(2,2,2-trifluoro-ethyl)-carbamic acid tert-butyl ester In analogy to the procedure described in example 3 the [5-cyano-2-methyl-6-oxo-4-(1,2,4,5-tetrahydro-benzo[d]azepin-3-yl)-6H-pyrimidin-1-yl]-carbamic acid tert-butyl ester (example 218) was treated with the 2,2,2-trifluoroethyl-trifluoromethanesulfonate in N,N-dimethylformamide in the presence of potassium carbonate at room temperature to yield the [5-cyano-2-methyl-6-oxo-4-(1,2,4,5-tetrahydro-benzo[d]azepin-3-yl)-6H-pyrimidin-1-yl]-(2,2,2-trifluoro-ethyl)-carbamic acid tert-butyl ester as colorless solid; m.p. 86–88° C.; MS: [M+H]$^+$=478.

EXAMPLE 242

[5-Cyano-2-methyl-6-oxo-4-(1,2,4,5-tetrahydro-benzo[d]azepin-3-yl)-6H-pyrimidin-1-yl]-isopropyl-carbamic acid tert-butyl ester In analogy to the procedure described in example 3 the [5-cyano-2-methyl-6-oxo-4-(1,2,4,5-tetrahydro-benzo[d]azepin-3-yl)-6H-pyrimidin-1-yl]-carbamic acid tert-butyl ester (example 218) was treated with the 2-iodopropane in N,N-dimethylformamide in the presence of potassium carbonate at room temperature to yield the [5-cyano-2-methyl-6-oxo-4-(1,2,4,5-tetrahydro-benzo[d]azepin-3-yl)-6H-pyrimidin-1-yl]-isopropyl-carbamic acid tert-butyl ester as colorless amorphous solid; MS: [M+H]$^+$=438.

EXAMPLE 243

1-Isopropylamino-2-methyl-6-oxo-4-(1,2,4,5-tetrahydro-benzo[d]azepin-3-yl)-1,6-dihydro-pyrimidine-5-carbonitrile In analogy to the procedure described in example 70 the [5-cyano-2-methyl-6-oxo-4-(1,2,4,5-tetrahydro-benzo[d]azepin-3-yl)-6H-pyrimidin-1-yl]-isopropyl-carbamic acid tert-butyl ester (example 242) was treated with 1.5N hydrogen chloride in methanol at room temperature to yield the 1-isopropylamino-2-methyl-6-oxo-4-(1,2,4,5-tetrahydro-benzo[d]azepin-3-yl)-1,6-dihydro-pyrimidine-5-carbonitrile as colorless solid; m.p. 142–146° C.; MS: [M+H]$^+$=338.

EXAMPLE 244

1-Ethylamino-2-methyl-6-oxo-4-(1,2,4,5-tetrahydro-benzo[d]azepin-3-yl)-1,6-dihydro-pyrimidine-5-carbonitrile In analogy to the procedure described in example 70 the [5-cyano-2-methyl-6-oxo-4-(1,2,4,5-tetrahydro-benzo[d]azepin-3-yl)-6H-pyrimidin-1-yl]-ethyl-carbamic acid tert-butyl ester (example 240) was treated with 1.5N hydrogen chloride in methanol at room temperature to yield the 1-ethylamino-2-methyl-6-oxo-4-(1,2,4,5-tetrahydro-benzo[d]azepin-3-yl)-1,6-dihydro-pyrimidine-5-carbonitrile as colorless solid; m.p. 172–174° C.; MS: [M+H]$^+$=324.

EXAMPLE 245

2-Methyl-6-oxo-4-(1,2,4,5-tetrahydro-benzo[d]azepin-3-yl)-1-(2,2,2-trifluoro-ethylamino)-1,6-dihydro-pyrimidine-5-carbonitrile In analogy to the procedure described in example 70 the [5-cyano-2-methyl-6-oxo-4-(1,2,4,5-tetrahydro-benzo[d]azepin-3-yl)-6H-pyrimidin-1-yl]-(2,2,2-trifluoro-ethyl)-carbamic acid tert-butyl ester (example 241) was treated with 1.5N hydrogen chloride in methanol at room temperature to yield the 2-methyl-6-oxo-4-(1,2,4,5-tetrahydro-benzo[d]azepin-3-yl)-1-(2,2,2-trifluoro-ethylamino)-1,6-dihydro-pyrimidine-5-carbonitrile as colorless solid; m.p. 144–146° C.; MS:[M+H]$^+$=378.

EXAMPLE 246

2-(2-Methoxy-ethoxy)-4-methylsulfanyl-6-(1,2,4,5-tetrahydro-benzo[d]azepin-3-yl)-pyrimidine-5-carbonitrile 0.011 g (0.25 mmol) of sodium hydride dispersion (50% in mineral oil) was added to a solution of 0.019 g (0.25 mmol) of the 2-methoxy-ethanol in 2 ml of tetrahydrofuran and the reaction mixture was stirred for 15 minutes at room temperature. Then, a solution of 0.10 g (0.25 mmol) of the 2-methylsulfanyl-4-(1,2,4,5-tetrahydro-benzo[d]azepin-3-yl)-6-(2,2,2-trifluoro-ethoxy)-pyrimidine-5-carbonitrile (example 166) in 3.0 ml of tetrahydrofuran was added and stirring continued at 40° C. for 16 hours. The reaction mixture was then poured into 150 ml of an ice/water mixture and extracted three times with 150 ml of dichloromethane. The combined organic phases were washed twice with 50 ml of water, dried over magnesium sulphate, evaporated under reduced pressure and dried in a high vacuum. The thus obtained crude product was purified by chromatography on silica gel using a 9:1 v/v mixture of hexane and ethyl acetate as eluent to yield 0.051 g (0.14 mmol), 55%, of the 2-(2-methoxy-ethoxy)-4-methylsulfanyl-6-(1,2,4,5-tetrahydro-benzo[d]azepin-3-yl)-pyrimidine-5-carbonitrile as colorless solid; m.p. 108–111° C.; MS: [M+H]$^+$=371.

EXAMPLE 247

4-Amino-2-methanesulfonyl-6-(1,2,4,5-tetrahydro-benzo[d]azepin-3-yl)-pyrimidine-5-carbonitrile Oxidation of the 4-amino-2-methylsulfanyl-6-(1,2,4,5-tetrahydro-benzo[d]azepin-3-yl)-pyrimidine-5-carbonitrile (example 164) with m-chloroperbenzoic acid in dichloromethane at room temperature yielded the 4-amino-2-methanesulfonyl-6-(1,2,4,5-tetrahydro-benzo[d]azepin-3-yl)-pyrimidine-5-carbonitrile as colorless solid; m.p. 184–185.5° C.; MS: [M+H]$^+$=344.

EXAMPLE 248

4-(1,2,4,5-Tetrahydro-benzo[d]azepin-3-yl)-2,6-bis-(2,2,2-trifluoro-ethox)-pyrimidine-5-carbonitrile In analogy to the procedure described in example 47 a) the 4-chloro-2-methylsulfanyl-6-(1,2,4,5-tetrahydro-benzo[d]azepin-3-yl)-pyrimidine-5-carbonitrile (example 149) was treated with the trifluoroethanol in tetrahydroftiran in the presence of sodium hydride at room temperature to yield beside the 2-methylsulfanyl-4-(1,2,4,5-tetrahydro-benzo[d]azepin-3-yl)-6-(2,2,2-trifluoro-ethoxy)-pyrimidine-5-carbonitrile (example 166) the 4-(1,2,4,5-tetrahydro-benzo[d]azepin-3-yl)-2,6-bis-(2,2,2-trifluoro-ethoxy)-pyrimidine-5-carbonitrile as colorless solid; m.p. 130–133.5° C.; MS: [M+H]$^+$=447.

EXAMPLE 249

2-Amino-4-methylsulfanyl-6-(1,2,4,5-tetrahydro-benzo[d]azepin-3-yl)-pyrimidine-5-carbonitrile In analogy to the procedure described in example 4 the 2-amino-4-bromo-6-methylsulfanyl-pyrimidine-5-carbonitrile [prepared from the 2,2-dicyano-1-methylsulfanyl-vinyl-cyanamide sodium salt [EP 244360 A2 (1987)] with excess hydrogen bromide in acetic acid between 0° C. and room temperature] was treated with the 2,3,4,5-tetrahydro-1H-benzo[d]azepine hydrochloride [J. Heterocycl. Chem. (1971), 8(5), 779–83] in dioxan in the presence of aqueous sodium hydroxide solution at room temperature to yield the 2-amino-4-methylsulfanyl-6-(1,2,4,5-tetrahydro-benzo[d]azepin-3-yl)-pyrimidine-5-carbonitrile as colorless solid; m.p. 164–168° C.; MS: [M]$^+$=311.

EXAMPLE 250

N-[5-Cyano-4-methylsulfanyl-6-(1,2,4,5-tetrahydro-benzo[d]azepin-3-yl)-pyrimidin-2-yl]-2-methoxy-acetamide A solution of 0.10 g (0.32 mmol) of the 2-amino-4-methylsulfanyl-6-(1,2,4,5-tetrahydro-benzo[d]azepin-3-yl)-pyrimidine-5-carbonitrile (example 249) in 5 ml of pyridine was treated with 0.072 g (0.64 mmol) of the methoxyacetylchloride and the reaction mixture was stirred at 60° C. for 16 hours. It was then poured into 150 ml of an ice/water mixture and extracted three times with 150 ml of dichloromethane. The combined organic phases were washed three times with 50 ml of 1N hydrogen chloride solution, twice with 50 ml of water, dried over magnesium sulphate, evaporated under reduced pressure and dried in a high vacuum. The thus obtained crude product was purified by chromatography on silica gel using a 1:1 v/v mixture of hexane and ethyl acetate as eluent to yield 0.070 g (0.18 mmol), 57%, of the N-[5-cyano-4-methylsulfanyl-6-(1,2,4,5-tetrahydro-benzo[d]azepin-3-yl)-pyrimidin-2-yl]-2-methoxy-acetamide as light yellow amorphous solid; MS: [M+H]$^+$=384.

EXAMPLE 251

[rac]-2-(2-Hydroxy-propylamino)-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the [rac]-1-amino-2-hydroxypropane in dioxan at 60° C. to yield the [rac]-2-(2-hydroxy-propylamino)-4-(1,2,4,5-tetrahydro-benzo[d]azepin-3-yl)-6-(2,2,2-trifluoro-ethoxy)-pyrimidine-5-carbonitrile as colorless solid; m.p. 141–147° C.; MS: [M+H]$^+$=422.

EXAMPLE 252

2-[2-(2-Hydroxy-ethoxy)-ethylamino]-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the 2-(2-aminoethoxy)-ethanol in dioxan at 40° C. to yield the 2-[2-(2-hydroxy-ethoxy)-ethylamino]-4-(1,2,4,5-tetrahydro-benzo[d]azepin-3-yl)-6-(2,2,2-trifluoro-ethoxy)-pyrimidine-5-carbonitrile as colorless amorphous solid; MS: [M+H]$^+$=452.

EXAMPLE 253

[rac]-2-[(2,2-Dimethyl-[1,3]dioxolan-4-ylmethyl)-amino]-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the [rac]-2,2-dimethyl-[1,3-dioxolane-4-methanamine in dioxan at 40° C. to yield the [rac]-2-[(2,2-dimethyl-[1,3]dioxolan-4-ylmethyl)-amino]-4-(1,2,4,5-tetrahydro-benzo[d]azepin-3-yl)-6-(2,2,2-trifluoro-ethoxy)-pyrimidine-5-carbonitrile as colorless amorphous solid; MS: [M+H]$^+$=478.

EXAMPLE 254

3-[5-Cyano-4-(1,2,4,5-tetrahydro-benzo[d]azepin-3-yl)-6-(2,2,2-trifluoro-ethoxy)-pyrimidin-2-ylamino]-propionic acid tert-butyl ester In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the beta-alanine-tert-butylester in dioxan at 50° C. to yield the 3-[5-cyano-4-(1,2,4,5-tetrahydro-benzo[d]azepin-3-yl)-6-(2,2,2-trifluoro-ethoxy)-pyrimidin-2-ylamino]-propionic acid tert-butyl ester as colorless amorphous solid; MS: [M+H]$^+$=492.

EXAMPLE 255

[5-Cyano-4-(1,2,4,5-tetrahydro-benzo[d]azepin-3-yl)-6-(2,2,2-trifluoro-ethoxy)-pyrimidin-2-ylamino]-acetic acid methyl ester In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the glycine-methylester hydrochloride and N-ethyl-N,N-diisopropylamin in dioxan at 50° C. to yield the [5-cyano-4-(1,2,4,5-tetrahydro-benzo[d]azepin-3-yl)-6-(2,2,2-trifluoro-ethoxy)-pyrimidin-2-ylamino]-acetic acid methyl esteras colorless solid; m.p. 136–140° C.; MS: [M+H]$^+$=436.

EXAMPLE 256

N-[5-Cyano-4-methylsulfanyl-6-(1,2,4,5-tetrahydro-benzo[d]azepin-3-yl)-pyrimidin-2-yl]-acetamide In analogy to the procedure described in example 250 the 2-amino-4-methylsulfanyl-6-(1,2,4,5-tetrahydro-benzo[d]

azepin-3-yl)-pyrimidine-5-carbonitrile (example 249) was treated with the acetylchloride in pyridine at 60° C. to yield the N-[5-cyano-4-methylsulfanyl-6-( 1,2,4,5-tetrahydro-benzo[d]azepin-3-yl)-pyrimidin-2-yl]-acetamide as colorless amorphous solid; MS: [M+H]$^+$=354.

EXAMPLE 257

N-5-Cyano-4-methylsulfanyl-6-(1,2,4,5-tetrahydro-benzo[d]azepin-3-yl)-pyrimidin-2-yl]-3-methyl-butyramide In analogy to the procedure described in example 250 the 2-amino-4-methylsulfanyl-6-(1,2,4,5-tetrahydro-benzo[d] azepin-3-yl)-pyrimidine-5-carbonitrile (example 249) was treated with the isovaleric acid chloride in pyridine at 60° C. to yield the N-[5-cyano-4-methylsulfanyl-6-(1,2,4,5-tetrahydro-benzo[d]azepin-3-yl)-pyrimidin-2-yl]-3-methyl-butyramide as colorless amorphous solid; MS: [M+H]$^+$=396.

EXAMPLE 258

4-(4-Methoxy-benzyloxy)-3-nitro-2-(1,2,4,5-tetrahydro-benzo[d]azepin-3-yl)-6,7,8,9-tetrahydro-5H-cyclohepta[b]pyridine In analogy to the procedure described in example 4 the trifluoro-methanesulfonic acid 4-(4-methoxy-benzyloxy)-3-nitro-6,7,8,9-tetrahydro-5H-cyclohepta[b]pyridin-2-yl ester (prepared from the trifluoro-methanesulfonic acid 3-nitro-2-trifluoromethanesulfonyloxy-6,7,8,9-tetrahydro-5H-cyclohepta[b]pyridin-4-yl ester (example 237) and 4-methoxy-benzyl alcohol, sodium hydride in tetrahydrofuran at room temperature) was treated with the 2,3,4,5-tetrahydro-1H-benzo[d]azepine hydrochloride [J. Heterocycl. Chem. (1971), 8(5), 779–83] in N,N-dimethylformamide in the presence of N-ethyl-N,N-diisopropylamine at room temperature to yield the 4-(4-methoxy-benzyloxy)-3-nitro-2-(1,2,4,5-tetrahydro-benzo[d] azepin-3-yl)-6,7,8,9-tetrahydro-5H -cyclohepta[b]pyridine as yellow amorphous solid; MS: [M+H]$^+$=474.

EXAMPLE 259

[rac]-2-(2,3-Dihydroxy-propylamino)-4-(1,2,4,5-tetrahydro-benzo[d]azepin-3-yl)-6-(2,2,2-trifluoro-ethoxy)-pyrimidine-5-carbonitrile In analogy to the procedure described in example 70 the [rac]-2-[(2,2-dimethyl-[1,3]dioxolan-4-ylmethyl)-amino]-4-(1,2,4,5-tetrahydro-benzo[d]azepin-3-yl)-6-(2,2,2-trifluoro-ethoxy)-pyrimidine-5-carbonitrile (example 253) was treated with hydrogen chloride in tetrahydrofuran at room temperature to yield the [rac]-2-(2,3-dihydroxy-propylamino)-4-(1,2,4,5-tetrahydro-benzo[d]azepin-3-yl)-6-(2,2,2-trifluoro-ethoxy)-pyrimidine-5-carbonitrile as colorless amorphous solid; MS: [M+H]$^+$=438.

EXAMPLE 260

4-Amino-2-(2-hydroxy-ethylamino)-6-(1,2,4,5-tetrahydro-benzo[d]azepin-3-yl)-pyrimidine-5-carbonitrile In analogy to the procedure described in example 48 the 4-amino-2-methanesulfonyl-6-(1,2,4,5-tetrahydro-benzo[d] azepin-3-yl)-pyrimidine-5-carbonitrile (example 247) was treated with the ethanolamine in dioxan at 80° C. to yield the 4-amino-2-(2-hydroxy-ethylamino)-6-(1,2,4,5-tetrahydro-benzo[d]azepin-3-yl)-pyrimidine-5-carbonitrile as colorless amorphous solid; MS: [M+H]$^+$=325.

EXAMPLE 261

2-(3-Hydroxy-propylamino)-4-(1,2,4,5-tetrahydro-benzo[d]azepin-3-yl)-6-(2,2,2-trifluoro-ethoxy)-pyrimidine-5-carbonitrile In analogy to the procedure described in example 48 the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the 3-aminopropanol in dioxane at 40° C. to yield the 2-(3-hydroxy-propylamino)-4-(1,2,4,5-tetrahydro-benzo[d]azepin-3-yl)-6-(2,2,2-trifluoro-ethoxy)-pyrimidine-5-carbonitrile as colorless amorphous solid; MS: [M+H]$^+$=422.

EXAMPLE 262

2-(2-Methoxy-ethoxy)-4-(1,2,4,5-tetrahydro-benzo[d]azepin-3-yl)-6-(2,2,2-trifluoro-ethoxy)-pyrimidine-5-carbonitrile In analogy to the procedure described in example 47 a) the 2-methanesulfonyl-4-(1,2,4,5-tetrahydro-benzo[d]azepin-3-yl)-6-(2,2,2-trifluoro-ethoxy)-pyrimidine-5-carbonitrile (example 172) was treated with the 2-methoxy-ethanol in tetrahydrofuran in the presence of sodium hydride at 40° C. to yield the 2-(2-methoxy-ethoxy)-4-(1,2,4,5-tetrahydro-benzo[d]azepin-3-yl)-6-(2,2,2-trifluoro-ethoxy)-pyrimidine-5-carbonitrile as colorless amorphous solid; MS: [M+H]$^+$=423.

EXAMPLE 263

1-Isopropoxy-2-methyl-6-oxo-4-(1,2,4,5-tetrahydro-benzo[d]azepin-3-yl)-1,6-dihydro-pyrimidine-5-carbonitrile In analogy to the procedure described in example 3 the 1-hydroxy-2-methyl-6-oxo-4-(1,2,4,5-tetrahydro-benzo[d] azepin-3-yl)-1,6-dihydro-pyrimidine-5-carbonitrile (example 199) was treated with isopropyl iodide in N,N-dimethylformamide in the presence of potassium carbonate at room temperature to yield the 1-isopropoxy-2-methyl-6-oxo-4-(1,2,4,5-tetrahydro-benzo[d]azepin-3-yl)-1,6-dihydro-pyrimidine-5-carbonitrile as colorless solid; m.p. 127–128° C.; MS: [M]$^+$=339.

EXAMPLE 264

3-[2-Methyl-5-nitro-6-(4-[1,2,4]triazol-1-yl-butoxy)-pyrimidin-4-yl]-2,3,4,5-tetrahydro-1H-benzo[d]azepine In analogy to the procedure described in example 202 the methanesulfonic acid 4-[2-methyl-5-nitro-6-(1,2,4,5-tetrahydro-benzo[d]azepin-3-yl)-pyrimidin-4-yloxy]-butyl ester (example 235) was treated with the 1,2,4-triazole and sodium hydride in N,N-dimethylformamide at room temperature to yield the 3-[2-methyl-5-nitro-6-(4-[1,2,4]triazol-1-yl-butoxy)-pyrimidin-4-yl]-2,3,4,5-tetrahydro-1H-benzo [d]azepine as light yellow solid; m.p. 88–91° C.; MS: [M+H]$^+$=424.

EXAMPLE 265

2-Methyl-5-nitro-6-(1,2,4,5-tetrahydro-benzo[d] azepin-3-yl)-3-(4-[1,2,4]triazol-1-yl-butyl)-3H-pyrimidin-4-one In analogy to the procedure described in example 202 the methanesulfonic acid 4-[2-methyl-5-nitro-6-oxo-4-(1,2,4,5- tetrahydro-benzo[d]azepin-3-yl)-6H-pyrimidin-1-yl]-butyl ester (example 236) was treated with the 1,2,4-triazole and sodium hydride in N,N-dimethylformamide at room temperature to yield the 2-methyl-5-nitro-6-(1,2,4,5-tetrahydro-benzo[d]azepin-3-yl)-3-(4-[1,2,4]triazol-1-yl-butyl)-3H-pyrimidin-4-one as light yellow amorphous solid; MS: [M+H]$^+$=424.

EXAMPLE 266

1-(3,3-Difluoro-allyl)-2-methyl-6-oxo-4-(1,2,4,5-tetrahydro-benzo[d]azepin-3-yl)-1,6-dihydro-pyrimidine-5-carbonitrile From the 2-methyl-6-oxo-4-(1,2,4,5-tetrahydro-benzo[d]azepin-3-yl)-1,6-dihydro-pyrimidine-5-carbonitrile (example 17) and 3-bromo-3,3-difluoropropene, potassium carbonate in N,N-dimethylformamide at room temperature as light yellow amorphous solid; m.p. 158–159° C.; MS: [M]$^+$=356; see example 267.

EXAMPLE 267

4-(3,3-Difluoro-allyloxy)-2-methyl-6-(1,2,4,5-tetrahydro-benzo[d]azepin-3-yl)-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with the 3-bromo-3,3-difluoropropene in N,N-dimethylformamide in the presence of potassium carbonate at room temperature to yield the 4-(3,3-difluoro-allyloxy)-2-methyl-6-(1,2,4,5-tetrahydro-benzo[d]azepin-3-yl)-pyrimidine-5-carbonitrile as colorless amorphous solid; MS: [M]$^{30}$=356; and the 1-(3,3-difluoro-allyl)-2-methyl-6-oxo-4-(1,2,4,5-tetrahydro-benzo[d]azepin-3-yl)-1,6-dihydro-pyrimidine-5-carbonitrile as light yellow amorphous solid; m.p. 158–159° C.; MS: [M]$^+$=356.

EXAMPLE 268

4-(1,1-Difluoro-allyloxy)-2-methyl-6-(1,2,4,5-tetrahydro-benzo[d]azepin-3-yl)-pyrimidine-5-carbonitrile From the 2-methyl-6-oxo-4-(1,2,4,5-tetrahydro-benzo[d]azepin-3-yl)-1,6-dihydro-pyrimidine-5-carbonitrile (example 17) and 3-bromo-3,3-difluoropropene, silver carbonate in 1,2-dichlorethane at reflux as light yellow amorphous solid; MS: [M]$^+$=356; see example 269.

EXAMPLE 269

1-(1,1-Difluoro-allyl)-2-methyl-6-oxo-4-(1,2,4,5-tetrahydro-benzo[d]azepin-3-yl)-1,6-dihydro-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with the 3-bromo-3,3-difluoropropene in 1,2-dichlorethane in the presence of silver carbonate at reflux to yield beside the 4-(3,3-difluoro-allyloxy)-2-methyl-6-(1,2,4,5-tetrahydro-benzo[d]azepin-3-yl)-pyrimidine-5-carbonitrile (example 267) the 1-(1,1-difluoro-allyl)-2-methyl-6-oxo-4-(1,2,4,5-tetrahydro-benzo[d]azepin-3-yl)-1,6-dihydro-pyrimidine-5-carbonitrile as colorless amorphous solid; MS: [M]$^+$=356; and the 4-(1,1-difluoro-allyloxy)-2-methyl-6-(1,2,4,5-tetrahydro-benzo[d]azepin-3-yl)-pyrimidine-5-carbonitrile as light yellow amorphous solid; MS: [M]$^+$=356.

EXAMPLE 270

4-Difluoromethoxy-2-methyl-6-(1,2,4,5-tetrahydro-benzo[d]azepin-3-yl)-pyrimidine-5-carbonitrile From the 2-methyl-6-oxo-4-(1,2,4,5-tetrahydro-benzo[d]azepin-3-yl)-1,6-dihydro-pyrimidine-5-carbonitrile (example 17) and 1-chloro-1,1-difluoromethane, potassium carbonate in N,N-dimethylformamide at 145° C. in an autoclave as colorless solid; m.p. 143° C.; MS: [M+H]$^+$=331; see example 271.

EXAMPLE 271

1-Difluoromethyl-2-methyl-6-oxo-4-(1,2,4,5-tetrahydro-benzo[d]azepin-3-yl)-1,6-dihydro-pyrimidine-5-carbonitrile In analogy to the procedure described in example 3 the 2-methyl-6-oxo-4-(1,2,4,5-tetrahydro-benzo[d]azepin-3-yl)-1,6-dihydro-pyrimidine-5-carbonitrile (example 17) was treated with the 1-chloro-1,1-difluoromethane in N,N-dimethylformamide in the presence of potassium carbonate at 145° C. in an autoclave for 30 minutes to yield the 1-difluoromethyl-2-methyl-6-oxo-4-(1,2,4,5-tetrahydro-benzo[d]azepin-3-yl)-1,6-dihydro-pyrimidine-5-carbonitrile as yellowish solid; m.p. 217° C.; MS:[M]$^+$=330; and the 4-difluoromethoxy-2-methyl-6-(1,2,4,5-tetrahydro-benzo[d]azepin-3-yl)-pyrimidine-5-carbonitrile as colorless solid; m.p. 143° C.; MS: [M+H]$^+$=331.

EXAMPLE 272

1-Difluoromethoxy-2-methyl-6-oxo-4-(1,2,4,5-tetrahydro-benzo[d]azepin-3-yl)-1,6-dihydro-pyrimidine-5-carbonitrile In analogy to the procedure described in example 3 the 1-hydroxy-2-methyl-6-oxo-4-(1,2,4,5-tetrahydro-benzo[d]azepin-3-yl)-1,6-dihydro-pyrimidine-5-carbonitrile (example 199) was treated with the 1-chloro-1,1-difluoromethane in N,N-dimethylformamide in the presence of potassium carbonate at 50° C. in an autoclave for 60 hours to yield the 1-difluoromethoxy-2-methyl-6-oxo-4-(1,2,4,5-tetrahydro-benzo[d]azepin-3-yl)-1,6-dihydro-pyrimidine-5-carbonitrile as colorless amorphous solid; MS: [M]$^+$=346.

EXAMPLE 273

1-Ethyl-2-methyl-6-oxo-4-(1,1,2-tritritio-1,2,4,5-tetrahydro-benzo[d]azepin-3-yl)-1,6-dihydro-pyrimidine-5-carbonitrile The 1-ethyl-2-methyl-6-oxo-4-(1,1,2-tritritio-1,2,4,5-tetrahydro-benzo[d]azepin-3-yl)-1,6-dihydro-pyrimidine-5-carbonitrile has been prepared from the ethyl 2-cyano-3,3-bis(methylthio)acrylate and the 1,1,2-tritritio-2,3,4,5-tetrahydro-1H-benzo[d]azepine as described in examples 13 a), 17 and 27/28. The 1,1,2-tritritio-2,3,4,5-tetrahydro-1H-benzo[d]azepine was obtained by the following sequence:

i) reaction of the 1-(1,2,4,5-tetrahydro-benzo[d]azepin-3-yl)-ethanone [J. Heterocycl. Chem. (1971), 8(5), 779–83] with dibenzoylperoxide and N-bromosuccinimide in carbon tetrachloride at reflux yielded the 1-(5-bromo-1,2-dihydro-benzo[d]azepin-3-yl)-ethanone;

ii) hydrogenation of the 1-(5-bromo-1,2-dihydro-benzo[d]azepin-3-yl)-ethanone with tritium using Pd/C in methanol in the presence of triethylamine yielded the 1-(1,1,2-tritritio-1,2,4,5-tetrahydro-benzo[d]azepin-3-yl)-ethanone;

iii) treatment of the 1-(1,1,2-tritritio-1,2,4,5-tetrahydro-benzo[d]azepin-3-yl)-ethanone with conc. aq. hydrochloric acid in methanol gave the 1,1,2-tritritio-2,3,4,5-tetrahydro-1H-benzo[d]azepine.

Example A

Tablets of the following composition are produced in a conventional manner:

| | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

Example B

Tablets of the following composition are produced in a conventional manner:

| | mg/Tablet |
|---|---|
| Active ingredient | 200 |
| Powdered lactose | 100 |
| White corn starch | 64 |
| Polyvinyipyrrolidone | 12 |
| Na carboxymethylstarch | 20 |
| Magnesium stearate | 4 |
| Tablet weight | 400 |

Example C

Capsules of the following composition are produced:

| | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:
1. A compounds of the formula

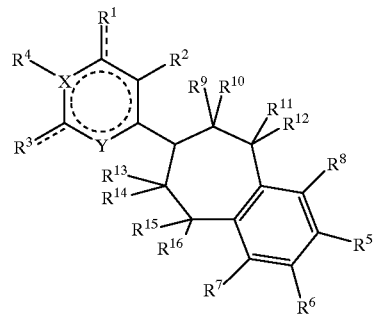

I wherein
$R^1$ signifies hydrogen, hydroxy, lower alkyl, oxygen, halogen, or
—OR, —O($C_3$–$C_6$)cycloalkyl, —O(CHR)$_n$—($C_3$–$C_6$) cycloalkyl, —O(CHR)$_n$CN, —O(CHR)$_n$CF$_3$, —O(CHR)(CHR)$_n$NR$_2$, —O(CHR)(CHR)$_n$OR, —O(CHR)$_n$-lower alkenyl, —OCF$_3$, —OCF$_2$—R, —OCF$_2$-lower alkenyl, —OCHRF, —OCHF-lower alkenyl, —OCF$_2$CRF$_2$, —OCF$_2$Br, —O(CHR)$_n$CF$_2$Br, —O(CHR)$_n$-phenyl, wherein the phenyl group may be optionally substituted independently from each other by one to three lower alkyl, lower alkoxy, halogen, nitro or cyano groups,
—O(CHR)(CHR)$_n$-morpholino, —O(CHR)(CHR)$_n$-pyrrolidino, —O(CHR)(CHR)$_n$-piperidino, —O(CHR)(CHR)$_n$-imidazolo, —O(CHR)(CHR)$_n$-triazolo, —O(CHR)$_n$-pyridino, —O(CHR)(CHR)$_n$—OSi-lower alkyl, —O(CHR)(CHR)$_n$OS(O)$_2$-lower alkyl, —O(CH$_2$)$_n$CH=CF$_2$, —O(CHR)$_n$-2,2-dimethyl-[1.3] dioxolane, —O(CHR)$_n$—CHOR—CH$_2$OR, —O(CHR)$_n$CHOR—(CHR)$_n$—CH$_2$OR or
—SR or —S(CHR)$_n$COOR, or
—NR$_2$, —N(R)(CHR)(CHR)$_n$OR, —N(R)(CHR)$_n$CF$_3$, —N(R)(CHR)(CHR)$_n$-morpholino, —N(R)(CHR)(CHR)$_n$-imidazolo, —N(R)(CHR)(CHR)$_n$-pyrrolidino, —N(R)(CHR)(CHR)$_n$-pyrrolidin-2-one, —N(R)(CHR)(CHR)$_n$-piperidino, —N(R)(CHR)(CHR)$_n$-triazolo, —N(R)(CHR)$_n$-pyridino, or
$R^1$ and $R^4$ are interconnected to the groups —(CH$_2$)$_{3-5}$—, —(CH$_2$)$_2$—N=, —CH=N—N=—, —CH=CH—N=, —NH—CH=CH— or —NR—CH$_2$–CH$_2$— and form together with any N or C atoms to which they are attached an additional ring;
n is 1–6;
R signifies hydrogen, lower alkyl or lower alkenyl, independently from each other, if more than one R is present;
$R^2$ signifies nitro or cyano;
$R^3$ signifies hydrogen, lower alkyl, =O, =S, —SR, —S(O)$_2$-lower alkyl, —(C$_3$–C$_6$)cycloalky or piperazino, optionally substituted by lower alkyl, or
—CONR$_2$, —(CHR)$_n$CONR$_2$, —(CHR)$_n$OR, —(CH$_2$)$_n$—CF$_3$, —CF$_3$, —(CHR)$_n$OC(O)CF$_3$, —(CHR)$_n$COOR, —(CHR)$_n$SC$_6$H$_5$, wherein the phenyl group may be optionally substituted independently from each other by one to three lower alkyl, lower alkoxy, halogen, nitro or cyano groups,
—(CHR)$_n$-1,3-dioxo-1,3-dihydro-isoindol, —(CHR)$_n$-tetrahydro-pyran-2-yloxy or —(CHR)$_n$—S-lower alkyl, or —NR$_2$, —NRCO-lower alkyl, —NRCHO, —N(R)(CHR)$_n$CN, —N(R)(CHR)$_n$CF$_3$, —N(R)(CHR)(CHR)$_n$—OR, —N(R)C(O)(CHR)$_n$O-lower alkyl, —NR(CHR)$_n$-lower alkyl, —NR(CHR)(CHR)$_n$—OR, —N(R)(CHR)(CHR)$_n$—O-phenyl, wherein the phenyl group maybe optionally substituted independently from each other by one to three lower alkyl, lower alkoxy, halogen, nitro or cyano groups, —N(R)(CHR)$_n$-lower alkenyl, —N(R)(CHR)(CHR)$_n$—O—(CHR)$_n$OR, —N(R)(CHR)$_n$C(O)O-lower alkyl, —N(R)(CHR)$_n$C(O)NR-lower alkyl, —N(R)(CH$_2$)$_n$-2,2-dimethyl-[1.3]dioxolane, —N(R)(CHR)(CHR)$_n$ morpholino, —N(R)(CHR)$_n$-pyridino, —N(R)(CHR)(CHR)$_n$-piperidino, —N(R)(CHR)(CHR)$_n$-pyrrolidino, —N(R)(CHR)(CHR)$_n$—O-pyridino, —N(R)(CHR)(CHR)$_n$imidazolo, —N(R)(CHR)$_n$—CR$_2$—(CHR)$_n$—OR, —N(R)(CHR)$_n$—CR$_2$—OR, —N(R)(CHR)$_n$—CHOR—CH$_2$OR, —N(R)(CHR)$_n$—CHOR—(CHR)$_n$—CH$_2$OR, or —OR, —O(CHR)$_n$CF$_3$, —OCF$_3$, —O(CHR)(CHR)$_n$—O-phenyl, wherein the phenyl group may be optionally substituted independently from each other by one to three lower alkyl, lower alkoxy, halogen, nitro or cyano groups, —O(CHR)(CHR)—O-lower alkyl, —O(CHR)$_n$-pyridino or —O(CHR)(CHR)$_n$-morpholino;

or R$^3$ and R$^4$ are interconnected to the groups —(CH$_2$)$_{3-5}$—, —(CH$_2$)$_n$—N═, —CH═N—N═—, —CH═CH—N═, —NH—CH═CH— or —NR—CH$_2$-CH$_2$— and form together with any N or C atoms to which they are attached an additional ring; and R$^4$ signifies hydrogen, lower alkyl, lower alkenyl or nitro, or —OR, —OCF$_3$, —OCF$_2$—R, —OCF$_2$-lower alkenyl, —OCHRF, —OCHP-lower alkenyl, —O(CHR)$_n$CF$_3$, or —(CHR)$_n$CHRF, —(CHR)$_n$CF$_2$R, —(CHR)$_n$CF$_3$, —(C$_3$–C$_6$)cycloalkyl, —(CHR)$_n$(C$_3$–C$_6$)cycloalkyl, —(CHR)$_n$CN, —(CHR)$_n$-phenyl, wherein the phenyl group may be optionally substituted independently from each other by one to three lower alkyl, lower alkoxy, halogen, nitro or cyano groups, —(CHR)(CHR)$_n$OR, —(CHR)$_n$CHORCH$_2$OR, —(CHR)(CHR)$_n$NR$_2$, —(CHR)$_n$COOR, —(CHR)(CHR)$_n$OSi-lower alkyl, —(CHR)(CHR)$_n$—OS(O)$_2$-lower alkyl, —(CH$_2$)$_n$—CH═CF$_2$, —CF$_3$, —CF$_2$—R, —CF$_2$-lower alkenyl, —CHRF, —CHF-lower alkenyl, —(CHR)$_n$-2,2-dimethyl-[1.3]dioxolane, —(CH$_2$)$_n$-2-oxo-azepan-1-yl, —(CHR)(CHR)$_n$-morpholino, —(CHR)$_n$-pyridino, —(CHR)(CHR)$_n$-imidazolo, —(CHR)(CHR)$_n$-triazolo, —(CHR)(CHR)$_n$-pyrrolidino, optionally substituted by —(CH$_2$)$_n$OH, —(CHR)(CHR)$_n$-3-hydroxy-pyrrolidino or —(CHR)(CHR)$_n$-piperidino, or —NR$_2$, —N(R)(CHR)$_n$-pyridino, —N(R)C(O)O-lower alkyl, —N(CH$_2$CF$_3$)C(O)O-lower alkyl, —N[C(O)O-lower alkyl]$_2$, —NR—NR—C(O)O-lower alkyl or —N(R)(CHR)$_n$CF$_3$, —NRCF$_3$, —NRCF$_2$—R, —NRCF$_2$-lower alkenyl, —NRCHRF, —NRCHF-lower alkenyl;

or is absent if X is —N═ or ═N—;

R$^5$, R$^6$ signify hydrogen, lower alkyl, lower alkoxy, amino, nitro, —SO$_2$NH$_2$, or halogen; or R$^5$ and R$^6$ are interconnected to the group —O—CH$_2$—O— and form together with the C atoms to which they are attached an additional 5-membered ring;

R$^7$, R$_8$ signify hydrogen, lower alkyl, lower alkoxy, amino, nitro or halogen;

R$^9$, R$^{10}$ signify hydrogen or lower alkyl;

R$^{11}$, R$^{12}$ signifies hydrogen, lower alkyl, hydroxy, lower alkoxy, lower alkoxycarbonyloxy or lower alkanoyloxy;

R$^{13}$, R$^{14}$ signify hydrogen, tritium or lower alkyl;

R$^{15}$, R$^{16}$ signifies hydrogen, tritium, lower alkyl, hydroxy, lower alkoxy or are together an oxo group; or X signifies —N═, ═N—, —N<, >C═ or ═C<;

Y signifies —N═, ═N—, —NH—, —CH═ or ═CH—; and the dotted line maybe a bond when R$^1$, R$^3$ or R$^4$ represent a bivalent atom, or a pharmaceutically acceptable salt thereof or their racemic or optically active form.

2. A compounds of claim 1 wherein R$^5$, R$^6$, R$^7$, R$^8$, R$^9$, R$^{10}$, R$^{11}$, R$^{12}$, R$^{13}$, R$^{14}$, R$^{15}$ and R$^{16}$ are all hydrogen.

3. A compounds of claim 2 wherein X and Y are both nitrogen.

4. A compounds of claim 1 wherein R$^1$ is ═O, OR, NR$_2$, or lower alkyl.

5. A compounds of claim 1 wherein R$^3$ is hydrogen, lower alkyl, or NR$_2$.

6. A compounds of claim 1 wherein R$^1$ is ═O, hydroxy, —O(CHR)$_n$CF$_3$, or —O(CHR)(CHR)$_n$-triazolo.

7. A compounds of claim 1 wherein R$^3$ and R$^4$ are interconnected to the groups —(CH$_2$)$_{3-5}$— to form together with any N or C atoms to which they are attached an additional ring.

8. A compounds of claim 6 wherein R$^1$ is ═O or hydroxy and R$^2$ is NO$_2$.

9. A compounds of claim 8 which are 3-ethyl-2-methyl-5-nitro-6-(1,2,4,5-tetrahydro-benzo[d]azepin-3-yl)-3H-pyrimidin-4-one, 3-(2-fluoro-ethyl)-2-methyl-5-nitro-6-(1,2,4,5-tetrahydro-benzo[d]azepin-3-yl)-3H-pyrimidin-4-one, 2-methyl-5-nitro-6-(1,2,4,5-tetrahydro-benzo[d]azepin-3-yl)-3-(2,2,2-trifluoro-ethyl)-3H-pyrimidin-4-one or 2-methyl-5-nitro-6-(1,2,4,5-tetrahydro-benzo[d]azepin-3-yl)-pyrimidin-4-ol.

10. A compounds of claim 6 wherein R$^1$ is ═O and R$^2$ is —CN.

11. A compounds of claim 10, which are 2-amino-6-oxo-4-(1,2,4,5-tetrahydro-benzo[d]azepin-3-yl)-1,6-dihydro-pyrimidine-5-carbonitrile, 6-oxo-4-(1,2,4,5-tetrahydro-benzo[d]azepin-3-yl)-1,6-dihydro-pyrimidine-5-carbonitrile, 2-ethylamino-6-oxo-4-(1,2,4,5-tetrahydro-benzo[d]azepin-3-yl)-1,6-dihydro-pyrimidine-5-carbonitrile, 1,2-dimethyl-6-oxo-4-(1,2,4,5-tetrahydro-benzo[d]azepin-3-yl)-1,6-dihydro-pyrimidine-5-carbonitrile, 1-ethyl-2-methyl-6-oxo-4-(1,2,4,5-tetrahydro-benzo[d]azepin-3-yl)-1,6-dihydro-pyrimidine-5-carbonitrile, 2-amino-1-ethyl-6-oxo-4-(1,2,4,5-tetrahydro-benzo[d]azepin-3-yl)-1,6-dihydro-pyrimidine5-carbonitrile, 1-cyclopropylmethyl-2-methyl-6-oxo-4-(1,2,4,5-tetrahydro-benzo[d]azepin-3-yl)-1,6-dihydro-pyrimidine-5-carbonitrile, 1-allyl-2-methyl-6-oxo-4-(1,2,4,5-tetrahydro-benzo[d]azepin-3-yl)-1,6-dihydro-pyrimidine-5-carbonitrile, 1-cyanomethyl-2-methyl-6-oxo-4-(1,2,4,5-tetrahydro-benzo[d]azepin-3-yl)-1,6-dihydro-pyrimidine-5-carbonitrile, 1-(2-dimethylamino-ethyl)-2-methyl-6-oxo-4-(1,2,4,5-tetrahydro-benzo[d]azepin-3-yl)-1,6-dihydro-pyrimidine-5-carbonitrile, 1-isopropyl-6-oxo-4-(1,2,4,5-tetrahydro-benzo[d]azepin-3-yl)-1,6-dihydro-pyrimidine-5-carbonitrile, 1-(2-hydroxy-ethyl)-6-oxo-4-(1,2,4,5-tetrahydro-benzo[d]azepin-3-yl)-1,6 dihydro-pyrimidine-5-carbonitrile, 2-(2-hydroxy-ethyl)-6-oxo-4-(1,2,4,5-tetrahydro-benzo[d]azepin-3-yl)-1,6 dihydro-pyrimidine-5-carbonitrile, 2-methyl-6-oxo-4-(1,2,4,5-tetrahydro-benzo[d]azepin-3-yl)-1-(2,2,2-trifluoro-ethoxy)-1,6-dihydro-pyrimidine-5-carbonitrile, 2-methyl-1-methylamino-6-oxo-4-(1,2,4,5-tetrahydro-benzo[d]azepin-3-yl)-1,6-dihydro-pyrimidine-5-carbonitrile or 1-amino-2-methyl-6-oxo-4-(1,2,4,5-tetrahydro-benzo[d]azepin-3-yl)-1,6-dihydro-pyrimidine-5-carbonitrile.

12. A compounds of claim 6 wherein $R^1$ is 2,2,2-trifluoroethoxy and $R^2$ is —CN.

13. A compounds of claim 12, which are 2-(2-morpholin-4-yl-ethylamino)-4-(1,2,4,5-tetrahydro-benzo[d]azepin-3-yl)-6-(2,2,2-trifluoro-ethoxy)-pyrimidine-5-carbonitrile, 5 2-(3-morpholin-4-yl-propylamino)-4-(1,2,4,5-tetrahydro-benzo[d]azepin-3-yl)-6-(2,2,2-trifluoro-ethoxy)-pyrimidine-5-carbonitrile, 2-(2-hydroxy-ethylamino)-4-(1,2,4,5-tetrahydro-benzo[d]azepin-3-yl)-6-(2,2,2-trifluoro-ethoxy)-pyrimidine-5-carbonitrile or (3-imidazol-1-yl-propylamino)-4-(1,2,4,5-tetrahydro-benzo[d]azepin-3-yl)-6-(2,2,2-trifluoro-ethoxy)-pyrimidine-5-carbonitrile.

14. A compounds of claim 6 wherein $R^1$ is 3-[1,2,4]triazol-1-yl-propoxy and $R^2$ is —NO$_2$ or —CN.

15. A compound of claim 14, which is

3-[2-methyl-5-nitro-6-(3-[1,2,4]triazol-1-yl-propoxy)-pyrimidin-4-yl]-2,3,4,5-tetrahydro-1H-benzo[d]azepine.

16. A compound of claim 7 wherein $R^3$ and $R^4$ are interconnected to the groups —(CH$_2$)$_{3-5}$— to form together with the N or C atoms to which they are attached an additional ring and $R^2$ is —NO$_2$ or —CN.

17. A compound of claim 16 which is 4-oxo-2-(1,2,4,5-tetrahydro-benzo[d]azepin-3-yl)-4,6,7,8,9,10-hexahydro-pyrimido[1,2-a]azepine-3-carbonitrile.

18. A compound of claim 1 wherein one or more of $R^{13}$, $R^{14}$, $R^{15}$, and $R^{16}$ is tritium.

19. A compound of claim 18 which is 1-ethyl-2-methyl-6-oxo-4-(1,1,2-tritritio-1,2,4,5-tetrahydro-benzo[d]azepin-3-yl)-1,6-dihydro-pyrimidine-5-carbonitrile.

20. A pharmaceutical composition comprising a compound of claim 1 or pharmaceutically acceptable salts thereof in their racemic and optically active form and pharmaceutically acceptable excipients.

* * * * *

UNITED STATES PATENT AND TRADEMARK OFFICE
CERTIFICATE OF CORRECTION

PATENT NO. : 6,218,385 B1
DATED : April 17, 2001
INVENTOR(S) : Geo Adam et al.

It is certified that error appears in the above-identified patent and that said Letters Patent is hereby corrected as shown below:

Title page,
Under "Abstract", chemical formula I should read as follows:

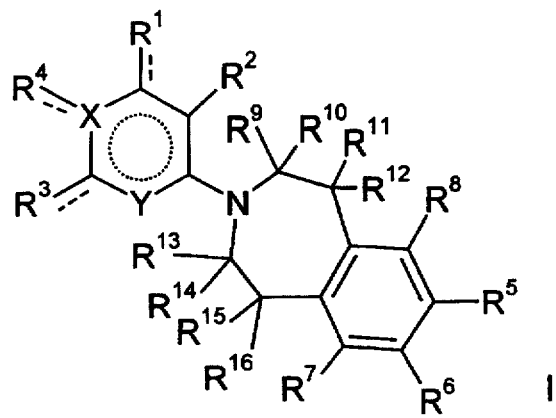

Column 2,
Lines 5-15, chemical formula I should read as follows:

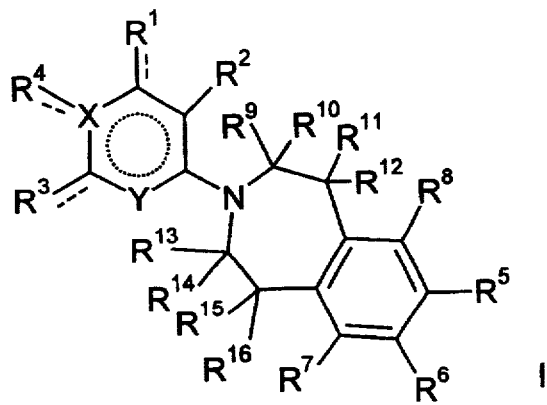

UNITED STATES PATENT AND TRADEMARK OFFICE
CERTIFICATE OF CORRECTION

PATENT NO.   : 6,218,385 B1
DATED        : April 17, 2001
INVENTOR(S)  : Geo Adam et al.

It is certified that error appears in the above-identified patent and that said Letters Patent is hereby corrected as shown below:

Column 10,
Lines 47-60, chemical formula I-6 should read as follows:

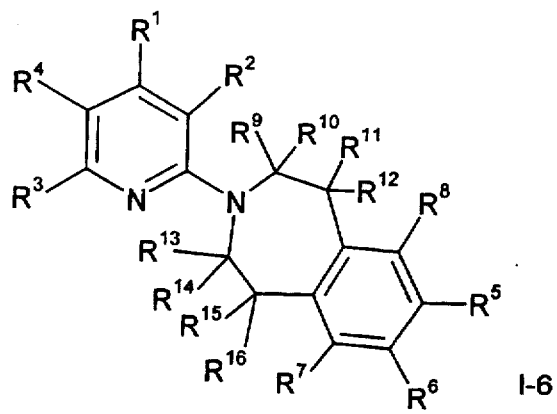

Column 90, claim 1,
Lines 5-15, chemical formula I should read as follows:

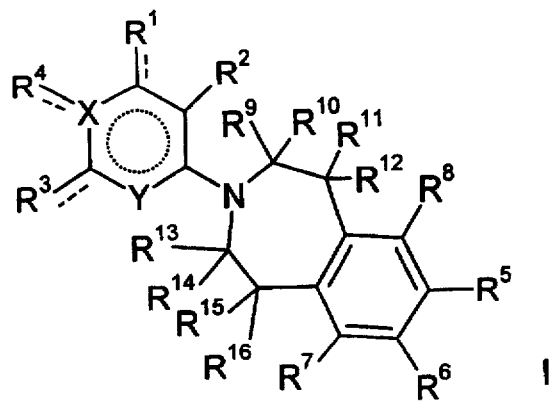

UNITED STATES PATENT AND TRADEMARK OFFICE
CERTIFICATE OF CORRECTION

PATENT NO. : 6,218,385 B1
DATED : April 17, 2001
INVENTOR(S) : Geo Adam et al.

It is certified that error appears in the above-identified patent and that said Letters Patent is hereby corrected as shown below:

<u>Column 91, claim 1,</u>
Line 23, delete "-O(CHR)(CHR)" and insert -- -O(CHR)(CHR)$_n$ --.
Line 35, delete " -OCHP-" and insert -- -OCHF- --.

<u>Claims 1-14,</u>
Line 1, delete "compounds" and insert -- compound --.

Signed and Sealed this

Thirteenth Day of November, 2001

Attest:

*Nicholas P. Godici*

NICHOLAS P. GODICI
*Attesting Officer*   *Acting Director of the United States Patent and Trademark Office*